United States Patent
Mirica et al.

(10) Patent No.: US 11,596,877 B2
(45) Date of Patent: Mar. 7, 2023

(54) POROUS SCAFFOLDS FOR ELECTROCHEMICALLY-CONTROLLED REVERSIBLE CAPTURE AND RELEASE OF ALKENES

(71) Applicant: Trustees of Dartmouth College, Hanover, NH (US)

(72) Inventors: Katherine A. Mirica, Hanover, NH (US); Xiaoping Zhang, West Lebanon, NH (US); Lukasz K. Mendecki, White River Junction, VT (US); Zheng Meng, West Lebanon, NH (US); Michael Ko, West Lebanon, NH (US)

(73) Assignee: Trustees of Dartmouth College, Hanover, NH (US)

( * ) Notice: Subject to any disclaimer, the term of this patent is extended or adjusted under 35 U.S.C. 154(b) by 0 days.

(21) Appl. No.: 16/636,097

(22) PCT Filed: Aug. 9, 2018

(86) PCT No.: PCT/US2018/045966
§ 371 (c)(1),
(2) Date: Feb. 3, 2020

(87) PCT Pub. No.: WO2019/032804
PCT Pub. Date: Feb. 14, 2019

(65) Prior Publication Data
US 2021/0162320 A1 Jun. 3, 2021

Related U.S. Application Data

(60) Provisional application No. 62/543,492, filed on Aug. 10, 2017.

(51) Int. Cl.
*B01D 15/38* (2006.01)
*B01D 53/02* (2006.01)
(Continued)

(52) U.S. Cl.
CPC ........ *B01D 15/3828* (2013.01); *B01D 53/02* (2013.01); *B01J 20/226* (2013.01);
(Continued)

(58) Field of Classification Search
None
See application file for complete search history.

(56) References Cited

U.S. PATENT DOCUMENTS

| | | | |
|---|---|---|---|
| 6,296,755 B1 | 10/2001 | Wang et al. | |
| 6,491,740 B1 | 12/2002 | Wang et al. | |

(Continued)

FOREIGN PATENT DOCUMENTS

| | | |
|---|---|---|
| WO | WO-12122233 A3 | 12/2012 |
| WO | WO-15113143 A1 | 8/2015 |

(Continued)

OTHER PUBLICATIONS

Long et al. Chem. Mater. 2014, 26, 323-338.*

(Continued)

*Primary Examiner* — Clinton A Brooks
(74) *Attorney, Agent, or Firm* — Shackelford, Bowen, McKinley & Norton, LLP

(57) ABSTRACT

In some embodiments, the present disclosure pertains to a method for capturing alkenes that includes: associating the alkenes with metal-organic frameworks, where the metal-organic frameworks includes one or more metals and one or more ligands coordinated with the one or more metals, and where the metal-organic frameworks are conductive; and oxidizing the metal-organic frameworks, where the oxidizing results in a capturing of the alkenes by the metal-organic frameworks. Additional embodiments of the present disclosure pertain to a system for capturing alkenes that includes: metal-organic frameworks, where the metal-organic frameworks include one or more metals and one or more ligands (Continued)

coordinated with the one or more metals, and where the metal-organic frameworks are conductive; and an alkene feed source associated with the metal-organic frameworks, where the alkene feed source is configured to deliver an alkene feed to the system.

15 Claims, 46 Drawing Sheets

(51) Int. Cl.
B01J 20/22 (2006.01)
C07F 1/08 (2006.01)
C07F 15/04 (2006.01)
C07F 15/06 (2006.01)

(52) U.S. Cl.
CPC .............. *C07F 1/08* (2013.01); *C07F 15/04* (2013.01); *C07F 15/06* (2013.01); *B01D 2253/204* (2013.01); *B01D 2257/7022* (2013.01)

(56) References Cited

U.S. PATENT DOCUMENTS

| | | | |
|---|---|---|---|
| 8,709,134 | B2 | 4/2014 | Yaghi et al. |
| 9,675,923 | B2 | 6/2017 | Long et al. |
| 11,092,562 | B2 | 8/2021 | Mirica et al. |
| 2007/0248852 | A1 | 10/2007 | Mueller et al. |
| 2011/0277767 | A1 | 11/2011 | Yaghi et al. |
| 2012/0215015 | A1 | 8/2012 | Yaghi et al. |
| 2012/0297982 | A1* | 11/2012 | Dinca ............. B01D 71/02 96/4 |
| 2013/0053585 | A1 | 2/2013 | Long et al. |
| 2018/0306740 | A1 | 10/2018 | Mirica et al. |
| 2020/0361976 | A1 | 11/2020 | Mirica |
| 2021/0164930 | A1 | 6/2021 | Mirica et al. |
| 2021/0230191 | A1 | 7/2021 | Mirica et al. |
| 2021/0262970 | A1 | 8/2021 | Mirica et al. |
| 2021/0310971 | A1 | 10/2021 | Mirica et al. |

FOREIGN PATENT DOCUMENTS

| | | |
|---|---|---|
| WO | WO-15171791 A1 | 11/2015 |
| WO | WO/2019/033104 A1 | 2/2019 |
| WO | WO-19032804 A1 | 2/2019 |
| WO | WO/2019/236799 | 12/2019 |
| WO | WO/2020/037310 | 2/2020 |
| WO | WO/2020/055474 | 4/2020 |

OTHER PUBLICATIONS

Yaghi et al. Chem. Mater. 2012, 24, 3511.*
Chopra et al. Postharvest Biology and Technology 130 (2017) 48-55.*
International Search Report and Written Report for PCT/US18/45966, dated Oct. 11, 2018.
International Preliminary Report on Patentability for PCT/US18/45966, dated Feb. 20, 2020.
Mei, L et al.; Adsorption performance of MIL-100(Fe) for separation of olefin-paraffin mixtures; Journal of the Taiwan Institute of Chemical Engineers 70 (2017) 74-78.
Maksimchuk, NV et al.; Metal-organic frameworks of the MIL-101 family of heterogeneous single-site catalysts; Proc. R. Soc. A., 468, 2017-2034; doi.org/10.1098/rspa.2012.0072.
Liao et. al. Efficient purification of ethene by an ethane-trapping metal-organic framework. *Nature Communications*. 2015(6); Article No. 8697 doi:10.1038/ncomms9697.
Li et al. Efficient separation of ethylene from acetylene/ethylene mixtures by a flexible-robust metal-organic framework. *J. Mater. Chem. A*, 2017(5); 18984-18988.
Bodke, A. S. Science 1999, 285, 712.
Suzuki, T.; Noble, R. D.; Koval, C. A. *Inorg. Chem.* 1997, 36, 136.
Wang, K.; Stiefel, E. I. Science 2001, 291, 106.
Sholl, D. S.; Lively, R. P. Nature 2016, 532, 435.
Herm, Z. R.; Bloch, E. D.; Long, J. R. Chem. Mater. 2014, 26, 323.
Schrauzer, G. N.; Mayweg, V. P. J. Am. Chem. Soc. 1965, 87, 1483.
Wing, R. M.; Tustin, G. C.; Okamura, W. H. J. Am. Chem. Soc. 1970, 92, 1935.
Baker, J. R.; Hermann, A.; Wing, R. M. J. Am. Chem. Soc. 1971, 93, 6486.
Dang, L.; Shibl, M. F.; Yang, X.; Alak, A.; Harrison, D. J.; Fekl, U.; Brothers, E. N.; Hall, M. B. J. Am. Chem. Soc. 2012, 134, 4481.
Raju, R. K.; Sredojevic, D. N.; Moncho, S.; Brothers, E. N. Inorg. Chem. 2016, 55, 10182.
Dang, L.; Shibl, M. F.; Yang, X.; Harrison, D. J.; Alak, A.; Lough, A. J.; Fekl, U.; Brothers, E. N.; Hall, M. B. Inorg. Chem. 2013, 52, 3711.
Harrison, D. J.; Lough, A. J.; Nguyen, N.; Fekl, U. Angew. Chem. Int. Ed. 2007, 46, 7644.
Boyer, J. L.; Cundari, T. R.; DeYonker, N. J.; Rauchfuss, T. B.; Wilson, S. R. Inorg. Chem. 2009, 48, 638.
Kunkely, H.; Vogler, A. Inorganica Chim. Acta 2001, 319, 183.
Dang, L.; Yang, X.;Zhou, J.; Brothers, E. N.; Hall, M. B. J. Phys. Chem. A 2012, 116, 476.
Grapperhaus, C. A.; Ouch, K.; Mashuta, M. S. J. Am. Chem. Soc. 2009, 131, 64.
Tang, Q.; Zhou, Z. J. Phys. Chem. C 2013, 117, 14125.
Moncho, S.; Brothers, E. N.; Hall, M. B. J. Mol. Model. 2015, 21, 107.
Dong, R.; Pfeffermann, M.; Liang, H.; Zheng, Z.; Zhu, X.; Zhang, J.; Feng, X. Angew. Chem. Int. Ed. 2015, 54, 12058.
Clough, A. J.; Yoo, J. W.; Mecklenburg, M. H.; Marinescu, S. C. J. Am. Chem. Soc. 2015, 137, 118.
Downes, C. A.; Marinescu, S. C. J. Am. Chem. Soc. 2015, 137, 13740.
Downes, C. A.; Marinescu, S. C. Dalton Trans 2016, 45, 19311.
Kobayashi, Y.; Jacobs, B.; Allendorf, M. D.; Long, J. R. Chem. Mater. 2010, 22, 4120.
Kambe, T.; Sakamoto, R.; Kusamoto, T.; Pal, T.; Fukui, N.; Hoshiko, K.; Shimojima, T.; Wang, Z.; 1. Hirahara, T.; Ishizaka, K.; Hasegawa, S.; Liu, F.; Nishihara, H. J. Am. Chem. Soc. 2014, 136, 14357.
Cui, J.; Xu, Z. Chem Commun 2014, 50, 3986.
Huang, X.; Sheng, P.; Tu, Z.; Zhang, F.; Wang, J.; Geng, H.; Zou, Y.; Di, C.; Yi, Y.; Sun, Y.; Xu, W.; Zhu, D. Nat. Commun. 2015, 6, 7408.
Clough, A. J.; Skelton, J. M.; Downes, C. A.; de la Rosa, A. A.; Yoo, J. W.; Walsh, A.; Melot, B. C.; Marinescu, S. C. J. Am. Chem. Soc. 2017, 139, 10863.
Pal, T.; Kambe, T.; Kusamoto, T.; Foo, M. L.; Matsuoka, R.; Sakamoto, R.; Nishihara, H. ChemPlusChem 2015, 80, 1255.
Zhao, M.; Wang, A.; Zhang, X. Nanoscale 2013, 5, 10404.
Smith, M. K.; Jensen, K. E.; Pivak, P. A.; Mirica, K. A. Chem. Mater. 2016, 28, 5264.
Hmadeh, M.; Lu, Z.; Liu, Z.; Gándara, F.; Furukawa, H.; Wan, S.; Augustyn, V.; Chang, R.; Liao, L.; Zhou, F.; Perre, E.; Ozolins, V.; Suenaga, K.; Duan, X.; Dunn, B.; Yamamto, Y.; Terasaki, O.; Yaghi, O. M. Chem. Mater. 2012, 24, 3511.
Sun, L.; Campbell, M. G.; Dinc?, M. Angew. Chem. Int. Ed. 2016, 55, 3566.
Campbell, M. G.; Sheberla, D.; Liu, S. F.; Swager, T. M.; Dinc?, M. Angew. Chem. Int. Ed. 2015, 54, 4349.
Sato, M.; Nagata, T.; Tanemura, A.; Fujihara, T.; Kumakura, S.; Unoura, K. Chem.—Eur. J. 2004, 10, 2166.
Loera-Serna, S.; Oliver-Tolentino, M. A.; de Lourdes López-Núñez, M.; Santana-Cruz, A.; Guzmán-Vargas, A.; Cabrera-Sierra, R.; Beltrán, H. L; Flores, J. J. Alloys Compd. 2012, 540, 113.
Peng, Z.; Yi, X.; Liu, Z.; Shang, J.; Wang, D. ACS Appl. Mater. Interfaces 2016, 8, 14578.
Davis, J. E.; McKetta, J. J. J. Chem. Eng. Data 1960, 5, 374.
Fogg, A. G. Anal. Proc. Anal. Commun. 1994, 31, 313.
Wang, J.; Mahmoud, J. S. J. Electroanal. Chem. Interfacial Electrochem. 1986, 208, 383.

(56) References Cited

OTHER PUBLICATIONS

Renon, H.; Lenoir, J. Y.; Renault, P. J. Chem. Eng. Data 1971, 16, 340.
Bloch, E. D.; Queen, W. L.; Krishna, R.; Zadrozny, J. M.; Brown, C. M.; Long, J. R. Science 2012, 335, 1606.
Cui, X.; Chen, K.; Xing, H.; Yang, Q.; Krishna, R.; Bao, Z.; Wu, H.; Zhou, W.; Dong, X.; Han, Y.; Li, B.; Ren, Q.; Zaworotko, M. J.; Chen, B. Science 2016, 353, 141.
Li, B.; Zhang, Y.; Krishna, R.; Yao, K.; Han, Y.; Wu, Z.; Ma, D.; Shi, Z.; Pham, T.; Space, B.; Liu, J.; Thallapally, P. K.; Liu, J.; Chrzanowski, M.; Ma, S. J. Am. Chem. Soc. 2014, 136, 8654.
Bao, Z.; Chang, G.; Xing, H.; Krishna, R.; Ren, Q.; Chen, B. Energy Env. Sci 2016, 9, 3612.
Liao, Y.; Zhang, L.; Weston, M. H.; Morris, W.; Hupp, J. T.; Farha, O. K. Chem Commun 2017, 53, 9376.

\* cited by examiner

FIG. 20A
FIG. 20B
FIG. 20C
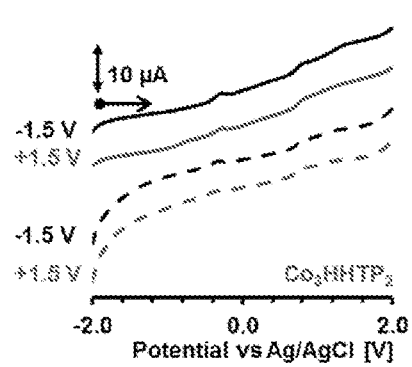
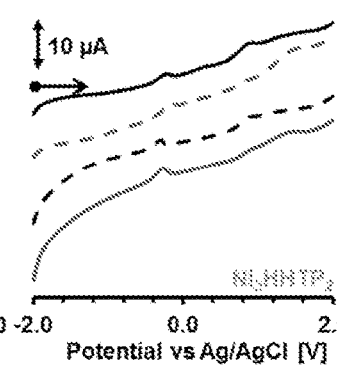
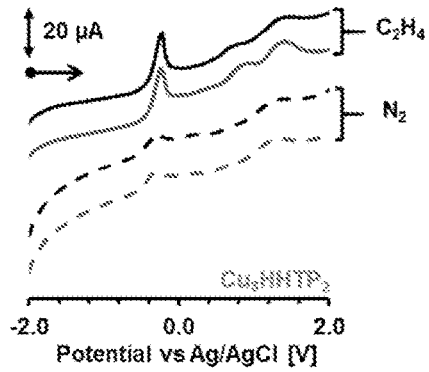

POROUS SCAFFOLDS FOR ELECTROCHEMICALLY-CONTROLLED REVERSIBLE CAPTURE AND RELEASE OF ALKENES

CROSS-REFERENCE TO RELATED APPLICATIONS

This application claims priority to U.S. Provisional Patent Application No. 62/543,492, filed on Aug. 10, 2017. The entirety of the aforementioned application is incorporated herein by reference.

BACKGROUND

Extraction of alkenes from various environments and sources (e.g., petroleum) is an energy-demanding process that involves many complex processes (e.g., steam cracking and cryogenic distillation). Alternative methods of alkene extraction that utilize transition metal complexes can improve energy-efficiency, but suffer from poisoning and the reduction in efficiency triggered by additional alkene feed components (e.g., $H_2$, $C_2H_2$, CO, and $H_2S$). Moreover, growing environmental concerns require improved methods for separating alkenes from various environmental sources (e.g., petrochemical feedstocks). The present disclosure addresses the aforementioned needs.

SUMMARY

In some embodiments, the present disclosure pertains to methods for capturing alkenes. In some embodiments, the methods include: associating the alkenes with metal-organic frameworks, where the metal-organic frameworks include one or more metals and one or more ligands coordinated with the one or more metals, and where the metal-organic frameworks are conductive; and oxidizing the metal-organic frameworks, where the oxidizing results in a capturing of the alkenes by the metal-organic frameworks.

In some embodiments, the associating step includes flowing the alkenes through the metal-organic frameworks. In some embodiments, the associating step includes incubating the alkenes with the metal-organic frameworks. In some embodiments, the associating step includes flowing the alkenes through the solution containing metal-organic frameworks.

In some embodiments, the one or more ligands of metal-organic frameworks can include, without limitation, hexatopic ligands, polydentate functional groups, aromatic ligands, triphenylene-based ligands, triphenylene derivatives, hexahydroxytriphenylene-based organic linkers, hexaiminotriphenlyene-based organic linkers, 2,3,6,7,10,11-hexathiotriphenylene (HTTP), 2,3,6,7,10,11-hexahydroxytriphenylene (HHTP), tridentate ligands, thiol-containing ligands, tridentate thiol-containing ligand, bis(dithiolene), and combinations thereof. In some embodiments, the one or more ligands include thiol-containing ligands.

In some embodiments, the one or more metals of metal-organic frameworks can include, without limitation, divalent metals, transition metals, nickel, copper, zinc, manganese, cobalt, chromium, iron, magnesium, tin, palladium, and combinations thereof. In some embodiments, the metal-organic frameworks can include, without limitation, $Co_3HHTP_2$, $Ni_3HHTP_2$, $Cu_3HHTP_2$, $Co_3HTTP_2$, $Ni_3HTTP_2$, $Cu_3HTTP_2$, and combinations thereof. In some embodiments, the metal-organic frameworks have a two-dimensional structure.

In some embodiments, the metal-organic frameworks are associated with a conductive surface. In some embodiments, the conductive surface is a conductive slide coated with the metal-organic frameworks. In some embodiments, the conductive surface is a conductive pellet including the metal-organic frameworks. In some embodiments, the conductive pellet includes a plurality of powdered metal-organic frameworks.

In some embodiments, the metal-organic frameworks include stacked layers to form a layered structure. In some embodiments, the layered structure can include, without limitation, a slipped parallel configuration or a staggered configuration. In some embodiments, the layered structure has an interlayer distance ranging from about 0.1 nm to about 2 nm.

In some embodiments, the alkenes to be captured can include, without limitation, ethylene, propylene, butylene, and combinations thereof. In some embodiments, the alkenes are in a gaseous state, a liquid state, or combinations thereof. In some embodiments, the alkenes are derived from a heterogeneous alkene feed. In some embodiments, the heterogeneous alkene feed can further include, without limitation, $C_2H_2$, CO, $H_2S$, $H_2$, or mixtures thereof.

In some embodiments, the oxidizing of metal-organic frameworks also results in filtration and pre-concentration of the alkenes by the metal-organic frameworks. In some embodiments, the oxidizing step occurs by a method that can include, without limitation, thermal-induced oxidation, chemical-induced oxidation, light-induced oxidation, voltage-induced oxidation, and combinations thereof. In some embodiments, the oxidizing occurs by voltage-induced oxidation. In some embodiments, the voltage-induced oxidation includes applying positive potential to the metal-organic frameworks.

In some embodiments, the capturing of the alkenes includes solid-state capturing of the alkenes. In some embodiments, the capturing of the alkenes includes solution-phase capturing of the alkenes. In some embodiments, the capturing of the alkenes occurs selectively. In some embodiments, the capturing of the alkenes occurs at a solid-gas interface, where the alkenes are in a gaseous state, and where the metal-organic frameworks are in a solid-state. In some embodiments, the capturing of alkenes occurs at a solid-solution interface, where the alkenes are in a liquid state, and where the metal-organic frameworks are in a solid-state.

In some embodiments, the oxidizing of metal-organic frameworks and the subsequent capture of alkenes can have additional effects. For instance, in some embodiments, the capture of alkenes can also result in the pre-concentration of the alkenes by the metal-organic frameworks, the catalytic transformation of the alkenes by the metal-organic frameworks, the sensing of the alkenes by the metal-organic frameworks, or combinations of such effects.

In some embodiments, the method for capturing alkenes can further include a step of releasing the alkenes from the metal-organic frameworks, where the releasing includes reducing the oxidized metal-organic frameworks. In some embodiments, the reducing occurs by a method that can include, without limitation, thermal-induced reduction, chemical-induced reduction, light-induced reduction, voltage-induced reduction, and combinations thereof. In some embodiments, the reducing occurs by voltage-induced reduction. In some embodiments, the voltage-induced reduction includes applying negative potential to the metal-organic frameworks.

In some embodiments, the method for capturing alkenes can further include a step of reusing the metal-organic frameworks after the releasing step for capture of additional alkenes. In some embodiments, the metal-organic frameworks may be utilized multiple times for capturing alkenes.

Additional embodiments of the present disclosure pertain to systems for capturing alkenes. In some embodiments, the systems include: metal-organic frameworks, where the metal-organic frameworks include one or more metals and one or more ligands coordinated with the one or more metals, and where the metal-organic frameworks are conductive; and an alkene feed source associated with the metal-organic frameworks, where the alkene feed source is configured to deliver an alkene feed to the system.

DESCRIPTION OF THE DRAWINGS

FIG. 11 shows electrochemical characterization of $M_3HTTP_2$ PCPs. Arrows indicate directions of scans. The double headed arrows indicate the magnitude of current.

FIG. 20 shows linear sweep voltammograms of $Co_3HHTP_2$ (FIG. 20A), $Ni_3HHTP_2$ (FIG. 20B), and $Cu_3HHTP_2$ (FIG. 20C) MOFs under ethylene atmosphere. All MOFs were either pre-oxidized (red) or pre-reduced (black) for 120 sec. Scan rate: 50 mV/s, 0.1 mM $TBAPF_6$ in $CH_3CN$. 3 mm diameter glassy carbon working electrode, platinum wire (mm diameter), and Ag/AgCl electrodes were used as the working, counter, and reference electrodes, respectively. Arrows indicate scan direction.

FIG. 22 shows experimental design and demonstration for solid-state electrochemical capture and release of ethylene.

DETAILED DESCRIPTION

It is to be understood that both the foregoing general description and the following detailed description are illustrative and explanatory, and are not restrictive of the subject matter, as claimed. In this application, the use of the singular includes the plural, the word "a" or "an" means "at least one", and the use of "or" means "and/or", unless specifically stated otherwise. Furthermore, the use of the term "including", as well as other forms, such as "includes" and "included", is not limiting. Also, terms such as "element" or "component" encompass both elements or components comprising one unit and elements or components that include more than one unit unless specifically stated otherwise.

The section headings used herein are for organizational purposes and are not to be construed as limiting the subject matter described. All documents, or portions of documents, cited in this application, including, but not limited to, patents, patent applications, articles, books, and treatises, are hereby expressly incorporated herein by reference in their entirety for any purpose. In the event that one or more of the incorporated literature and similar materials defines a term in a manner that contradicts the definition of that term in this application, this application controls.

Worldwide demand for ethylene, the lightest alkene obtained from petrochemical feedstocks, exceeds that of any other organic chemical. Extraction of ethylene from petroleum, however, is an energy-demanding process that involves steam cracking and cryogenic distillation. Alternatives that utilize transition metal complexes can improve energy efficiency, but suffer from poisoning—and the reduction in efficiency—triggered by $H_2$, $C_2H_2$, CO, and $H_2S$. Moreover, growing environmental concerns require improved methods for separating alkenes from petrochemical feedstocks.

Furthermore, implementation of solution-based electrochemical alternatives for separating alkenes are subject to complications due to several factors, including effect of solvent, choice of electrolyte, solubility of gas, and requirement for three electrode configurations. Thus, electrochemical capture of alkenes, and in particular ethylene, is a complex process, especially when the capture occurs in solution.

Strategies have been proposed for purifying alkenes from a multicomponent gas stream using an electrochemically-controlled cycloaddition reaction with metal bis(dithiolene) complexes. The implementation of this strategy in purification, however, has remained elusive, and has been limited to computational studies and demonstrations in solution using molecular complexes.

In sum, a need exists for more effective systems and methods for the electrochemical capture and release of alkenes. Various embodiments of the present disclosure address the aforementioned need.

Figure 1A:
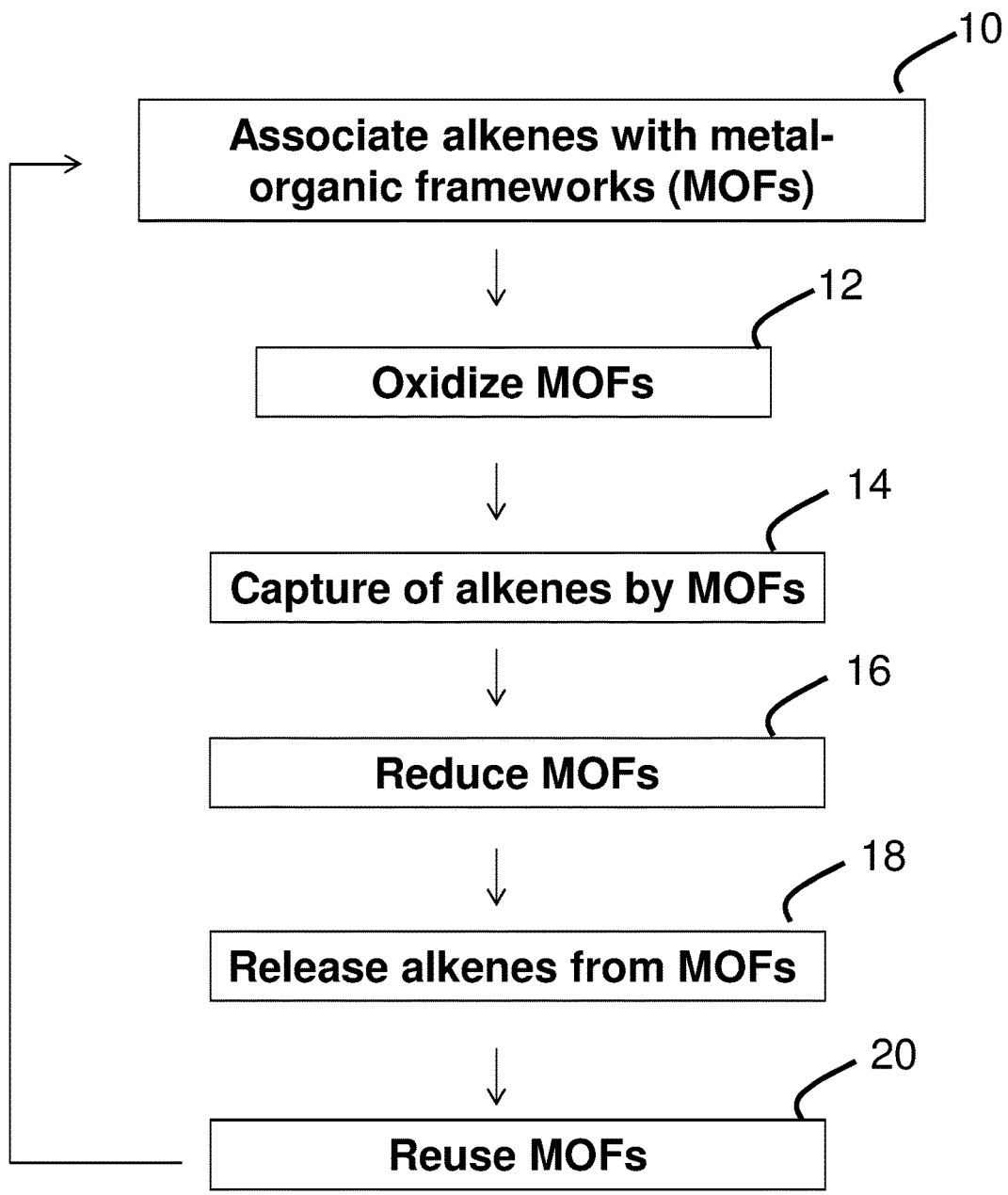
FIG. 1A illustrates a method for the capture and release of alkenes using metal-organic frameworks.

In some embodiments, the present disclosure pertains to methods for capturing alkenes using metal-organic frameworks. In some embodiments illustrated in FIG. 1A, the methods of the present disclosure includes the steps of associating alkenes with metal-organic frameworks (step 10), oxidizing the metal-organic frameworks (step 12), and capturing the alkenes by the metal-organic frameworks (step 14). In some embodiments, the methods of the present disclosure can also include the steps of reducing the metal-organic frameworks (step 16) and thereby releasing the alkenes from the reduced metal-organic frameworks (step 18). In some embodiments, the methods of the present disclosure also include a step of reusing the metal-organic frameworks for further capture of alkenes (step 20).

In some embodiments, steps 16-20, each, or in combination, can be omitted. In some embodiments, the methods of the present disclosure can begin at step 16, for example, if the metal-organic frameworks have been previously oxidized, have captured the alkenes, or have been stored in an environment conditioned to store the metal-organic frameworks until it is desired to release the alkenes.

Additional embodiments of the present disclosure pertain to systems for capturing alkenes. In some embodiments, the systems of the present disclosure can also be utilized to release captured alkenes. In some embodiments, the systems of the present disclosure include metal-organic frameworks and an alkene feed source associated with the metal-organic frameworks.

Figure 1B:
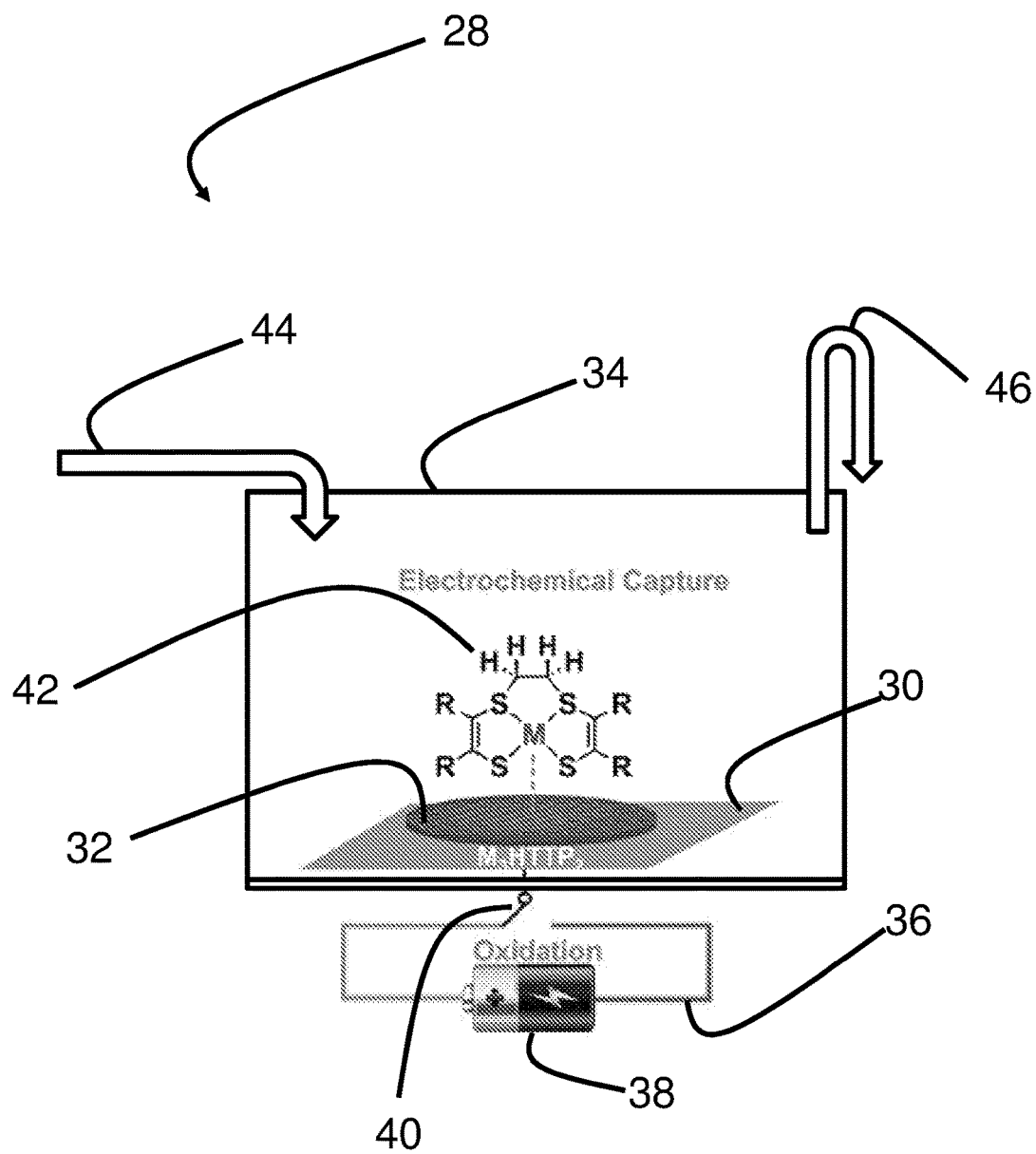
FIGS. 1B and 1C illustrate a system for the capture and release of alkenes using metal-organic frameworks, where oxidized metal-organic frameworks (FIG. 1B) capture alkenes, and where reduced metal-organic frameworks (FIG. 1C) release alkenes.
Figure 1C:
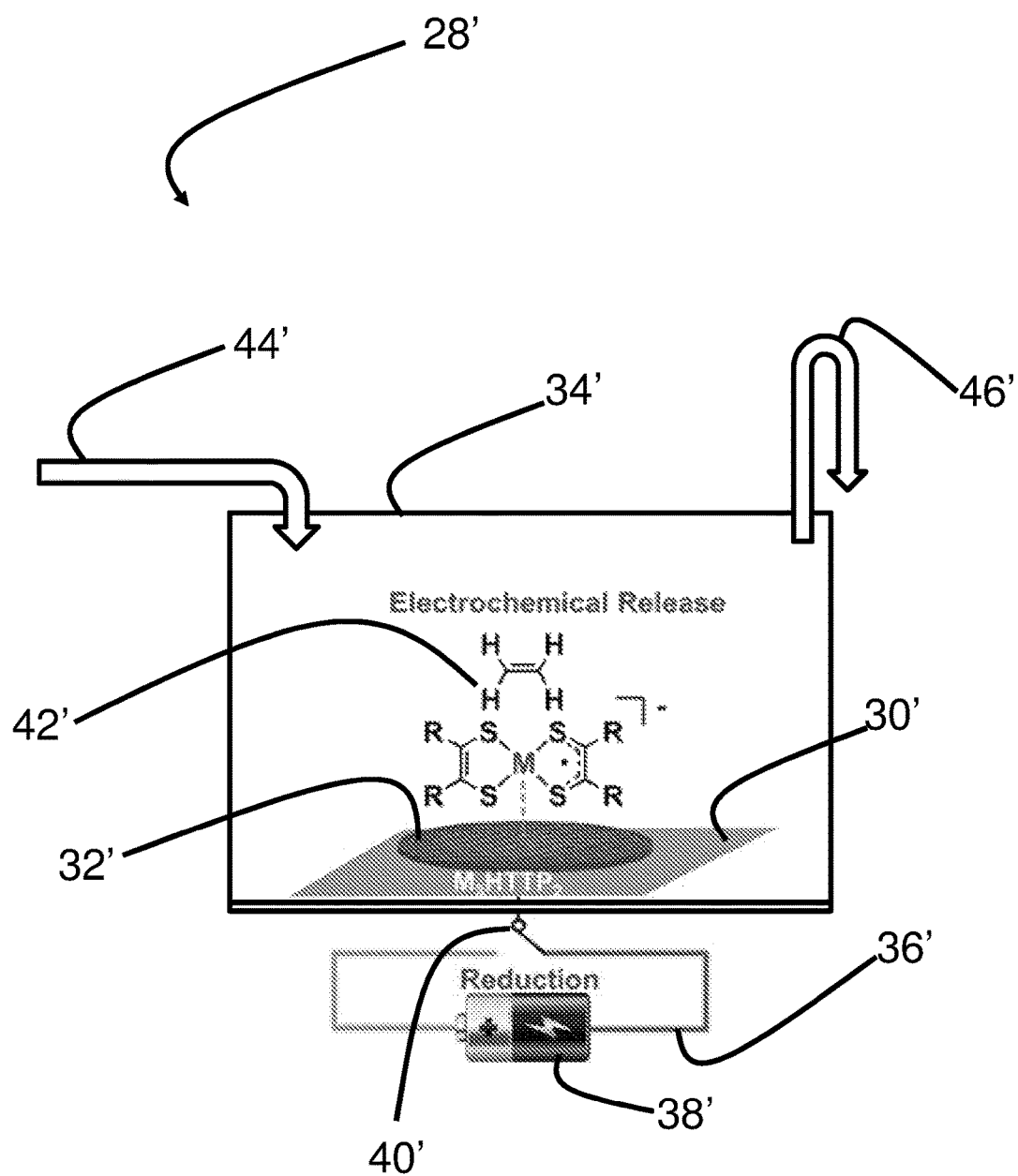

In more specific embodiments illustrated in FIGS. 1B and 1C, the systems of the present disclosure can include system 28. In this embodiment, system 28 can include metal-organic frameworks 32, alkene feed source 44, chamber 34, conductive surface 30 (e.g., in the form of a conductive slide), outlet 46, and wire 36 coupled to a potential source 38 that is operable to alternate potential from a positive potential to a negative potential (or to no potential) via a switch 40. In this embodiment, metal-organic frameworks 32 are in the form of a coating on a surface of conductive surface 30.

In some embodiments, an alkene 42 (e.g., illustrated as ethylene) can be associated with the metal-organic frameworks 32 by entering into the chamber 34 through alkene feed source 44. In some embodiments, the alkene feed source 44 can supply a gaseous feed, including a heterogeneous mixture of gases. Thereafter, and as illustrated in FIG. 1B, the switch 40 can be positioned to allow for positive potential to be supplied to the metal-organic frameworks 32 via the wire 36. Next, the positive potential results in the oxidation of the metal-organic frameworks 32 and the capture of alkene 42 by the metal-organic frameworks.

As illustrated in FIG. 1C, metal-organic frameworks 32' can be reduced after the capture of alkenes such that alkene 42' is released and fed through outlet 46' of the chamber 34'. For instance, switch 40' can be positioned to allow for negative potential to be supplied to the metal-organic frameworks 32' via the wire 36'. Thereafter, the metal-organic frameworks 32' are reduced. This results in the release of alkene 42'. Released alkene 42' can then be fed through outlet 46' of chamber 34'. The metal-organic frameworks 32' can then be reused after the release of alkene 42' for further capture of alkenes.

As set forth in more detail herein, the methods and systems of the present disclosure can have numerous embodiments. For instance, the methods of and systems of the present disclosure can utilize various types of metal-organic frameworks in various arrangements to capture and release various types of alkenes from various sources.

Metal-Organic Frameworks

The systems and methods of the present disclosure can utilize various types of metal-organic frameworks. In general, metal-organic frameworks include one or more metals and one or more ligands coordinated with the one or more metals. In some embodiments, the metal-organic frameworks of the present disclosure are conductive. Moreover, the metal-organic frameworks of the present disclosure may be associated with various types of conductive surfaces for the capture and release of alkenes. In addition, the metal-organic frameworks of the present disclosure may have various advantageous properties and characteristics.

Ligands

The metal-organic frameworks of the present disclosure can include various types of ligands. For instance, in some embodiments, the one or more ligands of the metal-organic frameworks can include, without limitation, hexatopic ligands, polydentate functional groups, aromatic ligands, triphenylene-based ligands, triphenylene derivatives, hexahydroxytriphenylene-based organic linkers, hexaiminotriphenylene-based organic linkers, 2,3,6,7,10,11-hexathiotriphenylene (HTTP), 2,3,6,7,10,11-hexahydroxytriphenylene (HHTP), tridentate ligands, thiol-containing ligands, tridentate thiol-containing ligand, bis(dithiolene), and combinations thereof.

In particular embodiments, the one or more ligands of the metal-organic frameworks are HTTP, HHTP, or combinations thereof. In some embodiments, the one or more ligands of the metal-organic frameworks are various thiol-containing ligands. In some embodiments, the one or more ligands of the metal-organic frameworks can include organic functional groups, inorganic functional groups, organic linkers, inorganic linkers, polymers, and combinations thereof. In some embodiments, electrochemical performance in a presence of the alkenes is dependent, at least in part, on sulfur-containing moieties of the one or more ligands.

Metals

The metal-organic frameworks of the present disclosure can include various types of metals. For instance, in some embodiments, the one or more metals can include, without limitation, divalent metals, transition metals, nickel, copper, zinc, manganese, cobalt, chromium, iron, magnesium, tin, palladium, and combinations thereof.

The metal-organic frameworks of the present disclosure may be in various forms. For instance, in some embodiments, more than one type of metal may be used at once within the same metal-organic frameworks. In some embodiments, the one or more metals of the metal-organic frameworks may be in the form of at least one of metal ions, metal clusters, metallic nodes, metal catecholates, metal salts, and combinations thereof.

In particular embodiments, the metal node of the metal-organic frameworks can be cobalt (II), nickel (II), or copper (II). In particular embodiments, the cobalt (II), nickel (II), or copper (II) can be supplied in the form of cobalt (II) acetate, nickel (II) acetate, or copper (II) trifluoroacetylacetonate, respectively.

In particular embodiments of the present disclosure, the metal-organic frameworks can include, without limitation, $Co_3HHTP_2$, $Ni_3HHTP_2$, $Cu_3HHTP_2$, $Co_3HTTP_2$, $Ni_3HTTP_2$, $Cu_3HTTP_2$, or combinations thereof. In some embodiments, the metal-organic frameworks of the present disclosure can have a protective coating.

Characteristics and Properties

The metal-organic frameworks of the present disclosure can include various structures. For instance, in some embodiments, the metal-organic frameworks of the present disclosure have a porous structure. In some embodiments, the metal-organic frameworks of the present disclosure include pore dimensions of approximately 2.0 nm. In some embodiments, the metal-organic frameworks of the present disclosure include a plurality of micropores.

In some embodiments, the metal-organic frameworks of the present disclosure have a two-dimensional structure. In some embodiments, the metal-organic frameworks of the present disclosure are in a stacked layer structure. In some embodiments, the stacked layer structure can be a slipped parallel configuration, a staggered configuration, or combinations thereof.

In some embodiments, the layered structures of the metal-organic frameworks of the present disclosure can have various interlayer distances. For instance, in some embodiments, the layered structures of the metal-organic frameworks of the present disclosure can have interlayer distances ranging from about 0.1 nm to about 100 nm. In some embodiments, the layered structures of the metal-organic frameworks of the present disclosure can have interlayer distances ranging from about 0.1 nm to about 2 nm. In some embodiments, the layered structures of the metal-organic frameworks of the present disclosure can have interlayer distances ranging from about 0.1 nm to about 1 nm. In some embodiments, the layered structures of the metal-organic frameworks of the present disclosure can have interlayer distances ranging from about 0.1 nm to about 0.5 nm. In some embodiments, the layered structures of the metal-organic frameworks of the present disclosure can have interlayer distances of approximately 0.40 nm.

The metal-organic frameworks of the present disclosure can also include various surface porosities. For instance, in some embodiments, the metal-organic frameworks of the present disclosure can have surface porosities that range from about 100 $m^2/g$ to about 500 $m^2/g$. In some embodiments, the metal-organic frameworks of the present disclosure can have surface porosities that range from about 100 $m^2/g$ to about 300 $m^2/g$. In some embodiments, the metal-organic frameworks of the present disclosure can have surface porosities that range from about 150 $m^2/g$ to about 266 $m^2/g$. In some embodiments, the metal-organic frameworks of the present disclosure can have surface porosities that range from about 166 $m^2/g$ to about 266 $m^2/g$.

In some embodiments, the metal-organic frameworks of the present disclosure are conductive. For instance, in some embodiments, the metal-organic frameworks of the present disclosure have bulk conductivities ranging from about $2.4 \times 10^{-9}$ S/cm to about $3.6 \times 10^4$ S/cm.

In some embodiments, the metal-organic frameworks of the present disclosure are capable of capturing alkenes in the presence of other interfering materials, such as reactive or poisonous gases. For instance, in some embodiments, the metal-organic frameworks of the present disclosure are capable of capturing alkenes in the presence of CO, $H_2S$, and combinations thereof.

In some embodiments, the metal-organic frameworks of the present disclosure are capable of solution-phase capture of alkenes in the presence of electrolytes (e.g., embodiments where alkenes are in a liquid state). In some embodiments, the metal-organic frameworks of the present disclosure are capable of direct solid-state capture of alkenes in the absence of electrolytes (e.g., embodiments where alkenes are in a gaseous state).

In some embodiments, the metal-organic frameworks of the present disclosure can be pre-oxidized or pre-reduced. In some embodiments, the metal-organic frameworks of the present disclosure exhibit strong paramagnetic behavior. In some embodiments, metal-center radicals are present in the metal-organic frameworks. In some embodiments, ligand-based radicals are present in the metal-organic frameworks.

In some embodiments, the metal-organic frameworks of the present disclosure employ relatively low overpotentials. In some embodiments, the overpotentials can be in the range of approximately −2.0 V to +2.0 V.

In some embodiments, the metal-organic frameworks of the present disclosure can utilize a class of modular porous materials. In some embodiments, the class of modular porous materials can be optimized for performance through strategic design.

In some embodiments, the metal-organic frameworks of the present disclosure can be compatible with low pressures and ambient temperatures. Moreover, in some embodiments, the metal-organic frameworks of the present disclosure can be compatible with different electrochemically controlled device configurations, such as standard 3-electrode electrochemical systems, solid-state pseudocapacitors, single-terminal electrodes, resistors, or combinations of the same and like.

In some embodiments, the metal-organic frameworks of the present disclosure provide for reversible electrochemically-driven capture and release of alkenes. In some embodiments, the molecular design of the metal-organic frameworks presented herein features the integration of motifs (e.g., metal bis(dithiolene) motifs) into a d-π conjugated, conductive, electrochemically active, and porous solid-state framework. In some embodiments, the design harnesses the established reactivity of various motifs (e.g., metal bis (dithiolene) complexes) with alkenes in liquids, and extends these principles directly to the solid-gas interface.

In some embodiments, the electrochemical characterization of the metal-organic frameworks allows for the metal-organic frameworks to undergo ligand-centered redox processes in water and in organic solvents. In some embodiments, alkene capture can be achieved in solution and directly in the solid-state using a variety of ligand complexes (e.g., metal bis(dithiolene)) complexes that incorporate Co, Ni, and Cu. In some embodiments, the metal-organic frameworks allow for reactivity of alkenes with various ligands (e.g., metal bis(dithiolene)s ligand) through the formation of S-based ligands, rather than through the formation of a π-complex with a metal center.

Association with Conductive Surfaces

In various embodiments, the metal-organic frameworks of the present disclosure can be associated with conductive surfaces. Conductive surfaces generally refer to surfaces that support the flow of electricity through the surface. In some embodiments, the flow of electricity through conductive surfaces can facilitate the oxidation and reduction of metal-organic frameworks for the purposes of alkene capture and release, respectively.

The metal-organic frameworks of the present disclosure can be associated with various types of conductive surfaces. For instance, in some embodiments, the conductive surfaces can include, without limitation, solid-state devices, electrode surfaces, conductive slides, conductive pellets, and combinations thereof.

The metal-organic frameworks of the present disclosure can be associated with conductive surfaces in various manners. For instance, in some embodiments, the metal-organic frameworks may be coated onto a conductive surface, such as in the form of a thin layer. In some embodiments, the metal-organic frameworks may be compressed onto a conductive surface, such as in the form of a pellet.

In more specific embodiments, the conductive surface can be a conductive slide coated with metal-organic frameworks. In some embodiments, a conductive slide can be prepared by sequentially evaporating a thin layer of chromium (e.g., approximately 10 nm) and gold (e.g., approximately 100 nm) onto a frosted glass slide. Thereafter, multiple aliquots of metal-organic frameworks may be drop-casted onto the conductive slide until proper loading (e.g., 5 mg) is achieved. In more specific embodiments, the metal-organic frameworks coated on the conductive slide can include, without limitation, $Co_3HHTP_2$, $Ni_3HHTP_2$, $Cu_3HHTP_2$, $Co_3HTTP_2$, $Ni_3HTTP_2$, $Cu_3HTTP_2$, or combinations thereof.

In some embodiments, the conductive surface can be a conductive pellet. In some embodiments, the conductive pellet may be in compressed form. In some embodiments, the conductive pellet may be associated with one or more types of metal-organic frameworks that are in powdered form. In some embodiments, the conductive pellets can be prepared by adding powdered forms of metal-organic frameworks into a pellet die having a diameter of, for example, approximately 6 mm and applying constant pressure (e.g., approximately 6.9 MPa for 5 minutes). In particular embodiments, the powdered metal-organic frameworks can include, without limitation, $Co_3HHTP_2$, $Ni_3HHTP_2$, $Cu_3HHTP_2$, $Co_3HTTP_2$, $Ni_3HTTP_2$, $Cu_3HTTP_2$, or combinations thereof.

In some embodiments, the conductive surfaces can be utilized in a container such that the conductive surfaces are positioned under an alkene atmosphere. In some embodiments, the conductive surfaces of the present disclosure can have a protective coating. In some embodiments, the conductive surfaces (e.g., conductive slides or conductive pellets) can be pre-oxidized or pre-reduced.

Methods for Capture of Alkenes by Metal-Organic Frameworks

The methods of the present disclosure can reversibly capture and release various alkenes in various manners. Such methods can include various steps of associating alkenes with metal-organic frameworks, oxidizing the metal-organic frameworks to result in the capturing of the alkenes by the metal-organic frameworks, releasing the alkenes from the metal-organic frameworks by reducing the oxidized metal-organic frameworks, and reusing the metal-organic frameworks after the releasing step for the capture of additional alkenes.

Association of Alkenes with Metal-Organic Frameworks

Various methods may be utilized to associate alkenes with metal-organic frameworks. For instance, in some embodiments, the association occurs by flowing the alkenes through the metal-organic frameworks. In some embodiments, the associating step includes flowing the alkenes through a solution containing metal-organic frameworks. In some embodiments, the association occurs by saturating the metal-organic frameworks in a solution of alkenes. In some embodiments, the association occurs by incubating the alkenes with the metal-organic frameworks.

In some embodiments, the association of alkenes with metal-organic frameworks occurs in an active manner, where an active step is taken to associate alkenes with the metal-organic frameworks. For instance, in some embodiments, the association occurs by actively flowing the alkenes through an alkene feed source to expose the alkenes to the metal-organic frameworks.

In some embodiments, the association of alkenes with metal-organic frameworks occurs in a passive manner that does not include an active step. For instance, in some embodiments, the association occurs through the passive incubation of the alkenes with the metal-organic frameworks.

Alkenes

The methods of the present disclosure can be utilized to capture various types of alkenes from various sources and in various states. For instance, in some embodiments, the alkenes are derived from petrochemical feedstocks. In some embodiments, the alkenes are derived from multicomponent gas streams. In some embodiments, the multicomponent gas streams can include, without limitation, $C_2H_2$, CO, $H_2S$, $H_2$, or mixtures thereof.

In some embodiments, the alkenes are in a gaseous state, a liquid state, or combinations thereof. In some embodiments, the alkenes are in a liquid state. In some embodiments, the alkenes are in a gaseous state. In some embodiments, the metal-organic frameworks reside under an atmosphere of gaseous alkenes or liquid alkenes.

In some embodiments, the alkenes can include, without limitation, ethylene, propylene, butylene, and combinations thereof. In some embodiments, the alkenes include ethylene, such as ethylene from petrochemical feedstocks.

Oxidizing the Metal-Organic Frameworks and Capturing Alkenes

The metal-organic frameworks of the present disclosure can be oxidized in various manners and at various times to result in the capture of alkenes. For instance, in some embodiments, the metal-organic frameworks of the present disclosure are oxidized before, during, and/or after the association of the alkenes with the metal-organic frameworks.

In some embodiments, the metal-organic frameworks of the present disclosure are oxidized before the association of the alkenes with the metal-organic frameworks. In some embodiments, the metal-organic frameworks of the present disclosure are oxidized before and during the association of the alkenes with the metal-organic frameworks.

Various methods may be utilized to oxidize metal-organic frameworks. For instance, in some embodiments, the oxidizing step can occur by thermal-induced oxidation, chemical-induced oxidation, light-induced oxidation, voltage-induced oxidation, and combinations thereof. In some embodiments, the metal-organic frameworks can undergo ligand-centered redox processes in solution during the oxidization process.

In some embodiments, the oxidizing occurs by voltage-induced oxidation. In some embodiments, the voltage-induced oxidation includes applying positive potential to the metal-organic frameworks. In some embodiments, the positive potential is in the range of approximately 0 V to +2.0 V.

Alkenes may be captured by oxidized metal-organic frameworks in various states. For instance, in some embodiments, the capturing of the alkenes includes solid-state capturing of the alkenes. In some embodiments, the capturing of the alkenes includes solution-phase capturing of the alkenes. In some embodiments, the capturing of the alkenes occurs at a solid-gas interface, where the alkenes are in a gaseous state, and where the metal-organic frameworks are in a solid-state. In some embodiments, the capturing of alkenes occurs at a solid-solution interface, where the alkenes are in a liquid state, and where the metal-organic frameworks are in a solid-state.

In additional embodiments, alkene capture can occur at the solid-gas phase by applying a positive potential in the range of approximately 0 V to +2.0 V to metal-organic frameworks (e.g., metal-organic frameworks associated with conductive surfaces) in the presence of gaseous alkenes to result in the capture of the alkenes. In some embodiments where the metal-organic frameworks are part of a conductive surface (e.g., on conductive slides or conductive pellets), alkene capture can occur at the solid-gas phase, and the capturing may be dependent, at least in part, on an exposed surface area of the conductive surface.

In some embodiments, the metal-organic frameworks of the present disclosure can capture alkenes in a selective manner. For instance, in some embodiments, the metal-organic frameworks of the present disclosure can capture alkenes (e.g., ethylene) in the presence of various other compounds such as, for example, CO, $H_2S$, $H_2$, $C_2H_2$ or mixtures thereof.

Capture of alkenes by metal-organic frameworks can be dependent on numerous factors. For instance, in some embodiments, the capture of the alkenes is dependent, at least in part, on a metal-ligand complex (e.g., metal bis (dithiolene) complex) of the metal-organic frameworks. In some embodiments, the capture of alkenes is dependent, at least in part, on sulfur-containing moieties of the one or more ligands of the metal-organic frameworks. In some embodiments, the capture of alkenes may be dependent on the metal center of the metal-ligand portion (e.g., metal bis(dithiolene) portion) of the metal-organic framework.

In some embodiments, the capture of alkenes may be dependent upon the organic portion of the ligand of a metal-organic framework (e.g., benzene, triphenylene, trinaphthalene, or other ligands). For instance, in some embodiments, the organic portion of a ligand may tune the reactivity of the metal-organic framework.

In some embodiments, the oxidizing of metal-organic frameworks and the subsequent capture of alkenes can also have additional effects. For instance, in some embodiments, the capturing of the alkenes can also result in pre-concentration (e.g., filtration) of the alkenes by the metal-organic frameworks, the catalytic transformation of the alkenes by the metal-organic frameworks, the sensing of the alkenes by the metal-organic frameworks, or combinations of such effects.

In some embodiments, the capturing of the alkenes also results in pre-concentration of the alkenes by the metal-organic frameworks. As such, in some embodiments, the metal-organic frameworks of the present disclosure may be used as pre-concentrators (e.g., voltage-actuated pre-concentrators) to concentrate alkenes at the metal-organic framework interface.

In some embodiments, the capturing of the alkenes also results in the catalytic transformation of the alkenes by the metal-organic frameworks. As such, in some embodiments, the metal-organic frameworks of the present disclosure may also serve as a catalyst such that the capture of the alkenes with the metal-organic frameworks activates the alkenes towards chemical transformations.

In some embodiments, the capturing of the alkenes also results in the sensing of the alkenes by the metal-organic frameworks. For instance, in some embodiments, metal-organic frameworks with metal bis(dithiolene) units may be used for the sensing of captured alkenes. As such, in some embodiments, the metal-organic frameworks of the present disclosure may also be utilized as sensors.

Reducing the Metal-Organic Frameworks and Releasing Alkenes

In some embodiments, the methods of the present disclosure can also include a step of reducing the metal-organic frameworks to thereby release the captured alkenes from the metal-organic frameworks. In some embodiments, the reduction step occurs after the oxidation and capture of the alkenes by the metal-organic frameworks.

Metal-organic frameworks may be reduced in various manners. For instance, in some embodiments, the reduction step can occur by thermal-induced reduction, chemical-induced reduction, light-induced reduction, voltage-induced reduction, and combinations thereof. In some embodiments, the metal-organic frameworks can undergo ligand-centered redox processes in solution during the reduction process.

In some embodiments, the reducing can occur by voltage-induced reduction. In some embodiments, the voltage-induced reduction includes applying negative potential to the metal-organic frameworks. In some embodiments, the negative potential is in the range of approximately 0 V to −2.0 V.

In more specific embodiments, the alkenes can be released after capture at the solid-gas phase by applying a negative potential in the range of approximately 0 V to −2.0 V to a metal-organic framework (e.g., metal-organic frameworks associated with conductive surfaces) to result in the release of the alkenes from the metal-organic frameworks.

Alkenes may be reduced in various states. For instance, in some embodiments, the reduction of the alkenes includes solid-state reduction of the alkenes. In some embodiments, the reduction of the alkenes includes solution-phase reduction of the alkenes. In some embodiments, the reduction of the alkenes occurs at a solid-gas interface, where the alkenes are in a gaseous state, and where the metal-organic frameworks are in a solid-state. In some embodiments, the reduction of the alkenes occurs at a solid-solution interface, where the alkenes are in a liquid state, and where the metal-organic frameworks are in a solid-state.

Release of alkenes from metal-organic frameworks can also be dependent on numerous factors. For instance, in some embodiments, the release of the alkenes is dependent, at least in part, on a metal-ligand complex (e.g., a metal bis(dithiolene) complex) of the metal-organic frameworks. In some embodiments, the release of alkenes is dependent, at least in part, on sulfur-containing moieties of the one or more ligands of the metal-organic frameworks In some embodiments, the release of alkenes may be dependent on the metal center of the metal-ligand portion (e.g., metal bis(dithiolene) portion) of the metal-organic framework. In some embodiments, the release of alkenes may be dependent upon the organic portion of the ligand of a metal-organic framework (e.g., benzene, triphenylene, trinaphthalene, or other ligands that may tune the reactivity of the metal-organic framework). For instance, in some embodiments, the organic portion of a ligand may tune the reactivity of the metal-organic framework Additional Capture of Alkenes The release of alkenes from the metal-organic frameworks can make the metal-organic frameworks available for the additional capture of alkenes. As such, in some embodiments, the alkene capture methods of the present disclosure can also include an additional step of reusing the metal-organic frameworks after the releasing step for the capture of additional alkenes. In some embodiments, the metal-organic frameworks of the present disclosure can be utilized multiple times (e.g., 10-100 times) for the repeated capture and release of alkenes.

Systems for Capture of Alkenes by Metal-Organic Frameworks

Additional embodiments of the present disclosure pertain to systems for capturing alkenes. The systems of the present disclosure generally include metal-organic frameworks with one or more metals and one or more ligands coordinated with the one or more metals; and an alkene feed source that is associated with the metal-organic frameworks and configured to deliver an alkene feed to the system.

Metal-organic frameworks suitable for use in the systems of the present disclosure were described previously. For instance, in some embodiments, the metal-organic frameworks are conductive.

Moreover, in some embodiments, the metal-organic frameworks in the systems of the present disclosure may be associated with a conductive surface. Suitable conductive surfaces were also described previously. For instance, in some embodiments, the conductive surface is a conductive slide coated with the metal-organic frameworks. In some embodiments, the conductive surface is a conductive pellet that contains metal-organic frameworks in powder form In some embodiments, the systems of the present disclosure include a solution-phase system. In some embodiments, the systems of the present disclosure include a solid-state system. Additional embodiments of the systems of the present disclosure are illustrated in FIGS. 1B and 1C described herein.

The systems of the present disclosure may also be utilized for purposes other than the capture of alkenes. For instance, in some embodiments, the systems of the present disclosure may also be utilized as pre-concentrators of the alkenes captured by the metal-organic frameworks. In some embodiments, the systems of the present disclosure may also be utilized as catalysts, where the captured alkenes are chemically transformed by metal-organic frameworks. In some embodiments, the systems of the present disclosure may also be utilized as sensors of alkenes, where the metal-organic frameworks chemically sense the captured alkenes.

Applications and Advantages

The systems and methods of the present disclosure describe the first experimental demonstration of using metal-organic frameworks for the reversible capture and release of alkenes. As such, the present disclosure can have various advantages. For instance, in some embodiments, the systems and methods of the present disclosure have at least the following advantages: i) they are compatible both with the solution-phase capture in the presence of electrolytes and with the direct solid-state capture in the absence of electrolytes; ii) they are resistant to poisoning by reactive gases, such as CO and $H_2S$; iii) they enable pre-concentration of alkenes within a metal-organic framework; iv) they employ relatively low overpotentials in the range of −2.0 V to +2.0 V; v) they utilize a class of modular porous materials that can be further optimized for performance through strategic design; vi) they are compatible with low pressure and ambient temperature; and vii) they are compatible with a number of different electrochemically-controlled device configurations, such as standard 3-electrode electrochemical systems, solid-state pseudocapacitors, single-terminal electrodes, or resistors.

Moreover, the systems and methods of the present disclosure provide at least three fundamental advances in the area of functional materials design for electrochemically-controlled chemical transformations. First, the systems and methods of the present disclosure provide a systematic electrochemical characterization of metal-organic frameworks to show that these conductive materials undergo ligand-centered redox processes in water and in organic solvent. Second, the systems and methods of the present demonstrate that alkene capture (e.g., ethylene capture) can be achieved in solution and directly in the solid-state using a variety of metal bis(dithiolene) complexes that incorporate Co, Ni, and Cu, thus expanding the scope of materials employed in experimental and theoretical studies towards this purpose. Third, the systems and methods of the present disclosure confirm the mechanistic hypotheses previously-proposed for reactivity of alkenes with metal bis(dithiolene)s through the S-based ligands, rather than through the formation of a π-complex with a metal center.

As such, the systems and methods of the present disclosure can be utilized in various manners and for various purposes. For instance, in some embodiments, the metal-organic frameworks presented herein can be utilized for the reversible capture and/or release of alkenes in various environments. Such environments can include a solution-phase in the presence of electrolytes. Such environments can also include a solid-state in the absence of electrolytes.

Additional Embodiments

Reference will now be made to more specific embodiments of the present disclosure and experimental results that provide support for such embodiments. However, Applicants note that the disclosure below is for illustrative purposes only and is not intended to limit the scope of the claimed subject matter in any way.

Example 1

Porous Scaffolds for Electrochemically-Controlled Reversible Capture and Release of Ethylene This Example describes a use of porous coordination polymers (PCP) with integrated metal bis(dithiolene) units to achieve electrochemically-controlled capture and release of ethylene in the solid state. Applying positive potential (+2.0 V) to these PCPs promotes ethylene capture, and subsequent dose of negative potential (−2.0 V) induces the release. These materials are resistant to poisoning by small reactive gases (CO and $H_2S$) that may interact with embedded metallic sites.

Figure 2A:
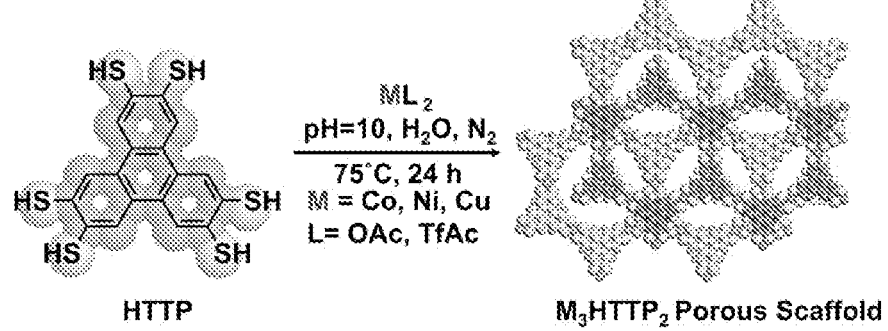
FIG. 2A shows the synthesis of metal-organic frameworks (also referred to as porous coordination polymers or PCPs).
Figure 2B:
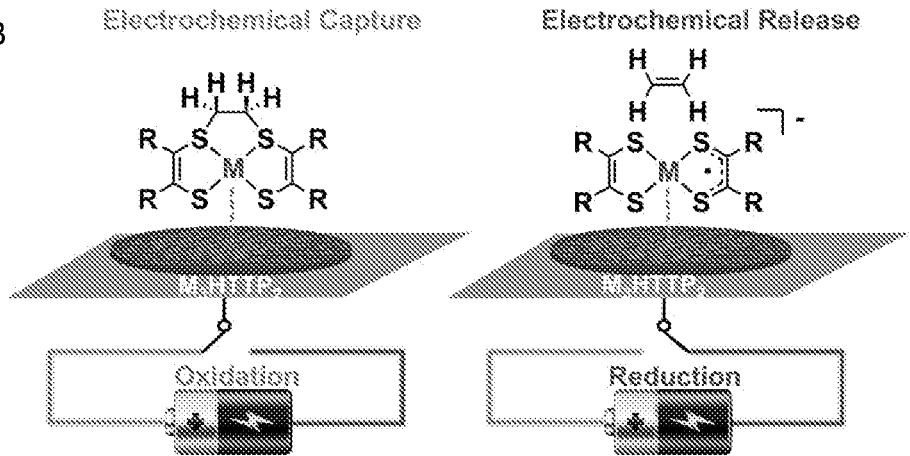
FIG. 2B shows an illustration of proposed voltage-actuated capture and release of ethylene with PCPs.
Figure 3A:
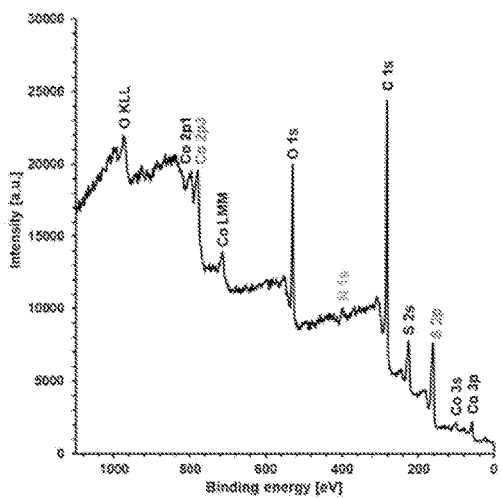
FIG. 3A shows an energy survey scan. Also shown are high-resolution spectra in the S 2p (FIG. 3B), Co 2p3 (FIG. 3C), and N 1s (FIG. 3D) regions. The doublet peaks observed in the S 2p spectrum with an intensity ratio of 1:2 result from the spin-orbit coupling, and are characteristic of the S 2p3/2 and 2p1/2 orbitals.
Figure 3B:
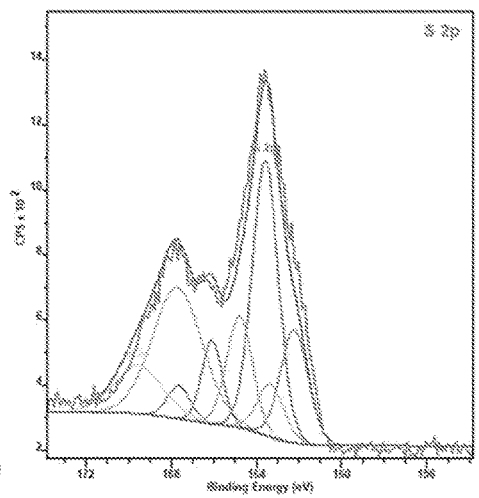
FIG. 3 shows X-Ray Photoelectron Spectroscopy (XPS) spectra obtained for the $Co_3HTTP_2$ PCPs.
Figure 3C:
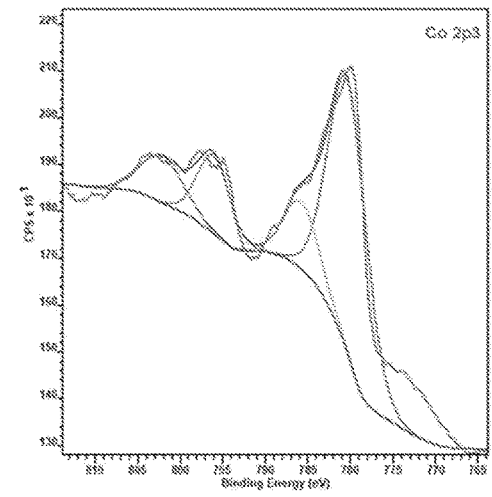
Figure 3D:
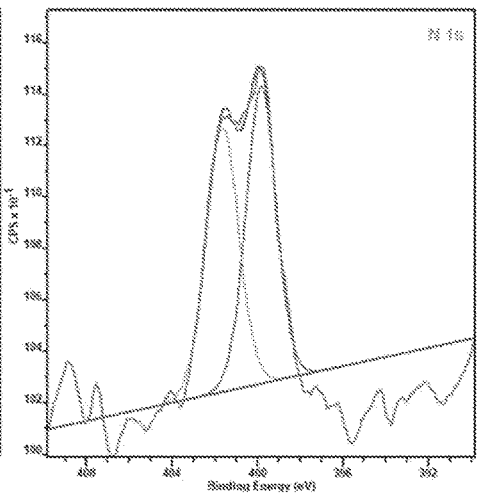
Figure 4A:
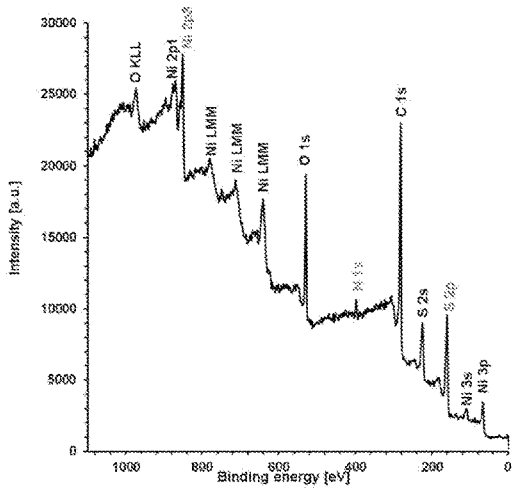
FIG. 4A shows an energy survey scan. Also shown are high-resolution spectra in the S 2p (FIG. 4B), Ni 2p3 (FIG. 4C), and N 1s (FIG. 4D) regions. The doublet peaks observed in the S 2p spectrum with an intensity ratio of 1:2 result from the spin-orbit coupling, and are characteristic of the S 2p3/2 and 2p1/2 orbitals.
Figure 4B:
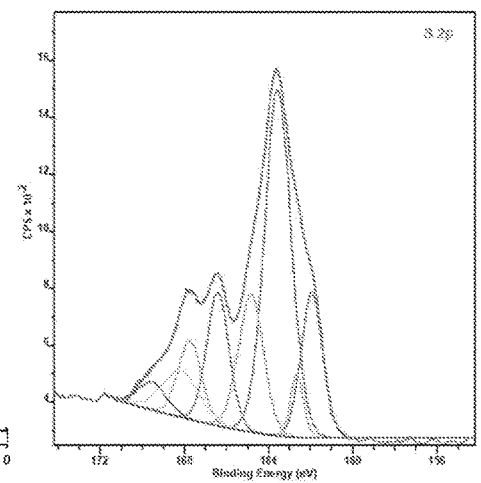
FIG. 4 shows XPS spectra obtained for the $Ni_3HTTP_2$ PCPs.
Figure 4C:
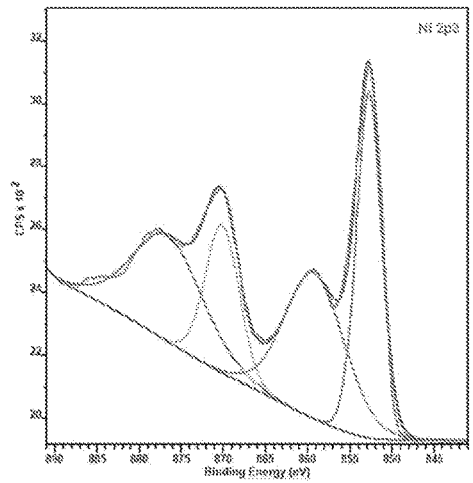
Figure 4D:
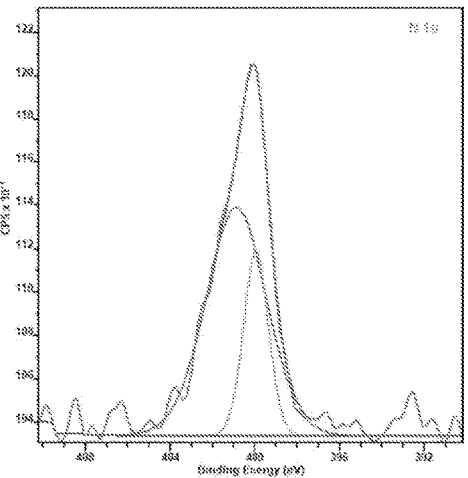
Figure 5A:
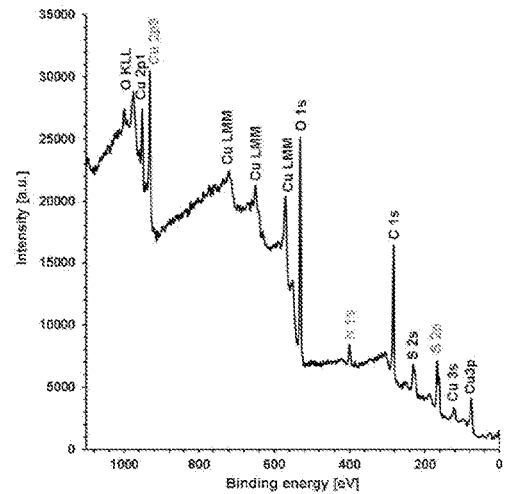
FIG. 5A shows an energy survey scan. Also shown are high-resolution spectra in the S 2p (FIG. 5B), Cu 2p3 (FIG. 5C), and N 1s (FIG. 5D) regions. The doublet peaks observed in the S 2p spectrum with an intensity ratio of 1:2 result from the spin-orbit coupling, and are characteristic of the S 2p3/2 and 2p1/2 orbitals.
Figure 5B:
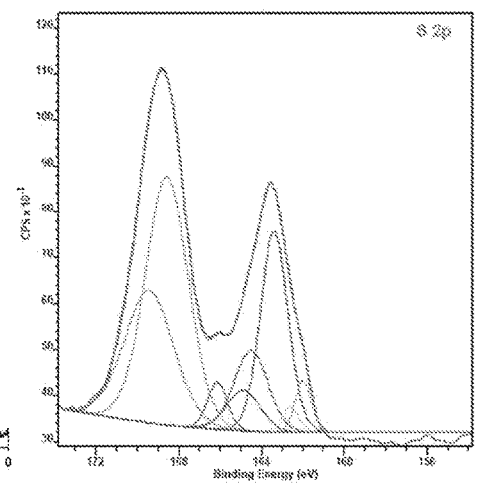
FIG. 5 shows XPS spectra obtained for the $Cu_3HTTP_2$ PCPs.
Figure 5C:
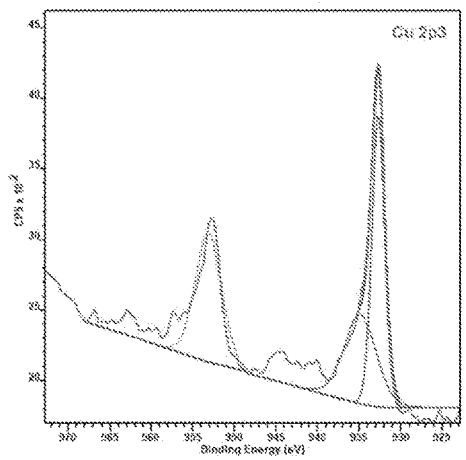
Figure 5D:
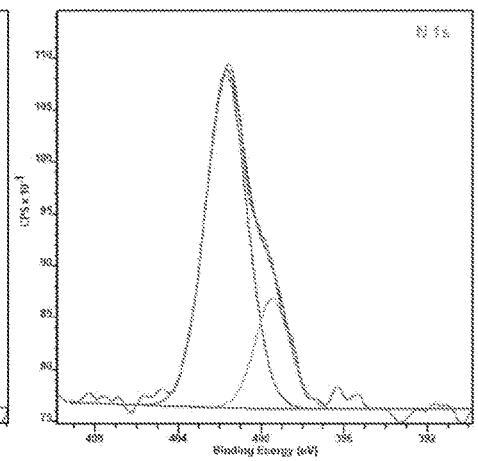

This Example describes an experimental demonstration of using porous coordination polymers (PCPs) for reversible electrochemically-driven capture of ethylene. The molecular design features the integration of the metal bis(dithiolene) units into d-π conjugated, conductive, electrochemically active PCPs (FIG. 2). While this class of materials has been shown to exhibit promising electrocatalytic, electronic, and magnetic properties, its function in reversible electrochemical molecular capture has not been shown. Applicants used reticular synthesis through the reaction between 2,3,6,7,10,11-hexathiotriphenylene (HTTP) linkers and divalent metal ions ($M^2$) supplied in the form of cobalt (II) acetate, nickel (II) acetate, or copper (II) trifluoroacetylacetonate, under basic conditions (pH 10) to generate $M_3HTTP_2$ PCPs (FIG. 2A). To probe the role of the chalcogen atom (S vs O), and the role of the metal in voltage-actuated capture, 2,3,6,7,10,11-hexahydroxytriphenylene (HHTP)-based analogs, $M_3HHTP_2$ metal-organic frameworks (MOFs), were also tested, as discussed in further detail below.

Inductively-coupled plasma mass spectrometry (ICP-MS) quantified the metal content in the bulk to be consistent with the molecular formula of $M_3HTTP_2$ (Table 1-Table 3, detailed below in Example 1.13). X-Ray Photoelectron Spectroscopy (XPS) demonstrated mixed valency in $Co_3HTTP_2$ ($Co^{2+}/Co^{3+}$) and in $Cu_3HTTP_2$ ($Cu^{1+}/Cu^{2+}$), with only $Ni^{2+}$ present in $Ni_3HTTP_2$ (FIG. 3-FIG. 5). XPS also revealed the presence of $NH_4^+$ counter-ions, consistent with the anionic form of $[M_3HTTP_2]^-$ subunits, and the presence of O-containing defects in the form of sulfates and sulfites (FIG. 3-FIG. 5). These findings are consistent with previous reports of similar materials. Combustion analysis quantified the amount of S, C, and N in the bulk (Table 1-Table 3, detailed below in Example 1.13). S, C, M (Co, Ni, Cu), and O were also observed by Energy-Dispersive X-Ray spectroscopy (EDS, FIG. 6C).

Figure 6A:
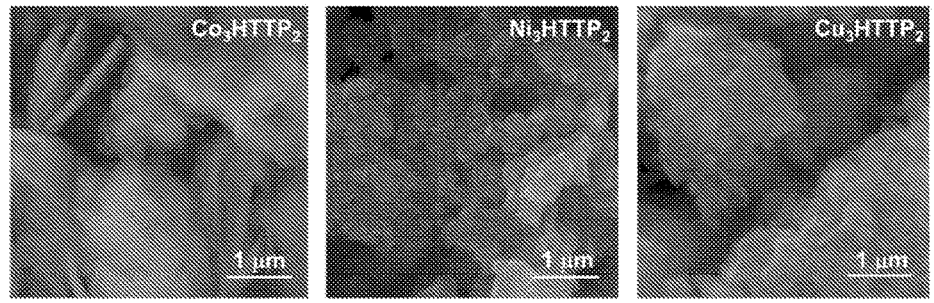
FIG. 6A shows scanning electron micrographs showing nanoscale morphology of HTTP-based PCPs.
Figure 6B:
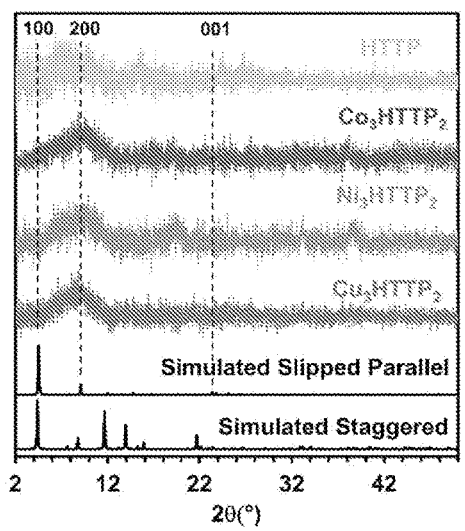
FIG. 6B shows experimental (colored) and simulated (black) powder X-Ray Diffraction patterns.
Figure 6C:
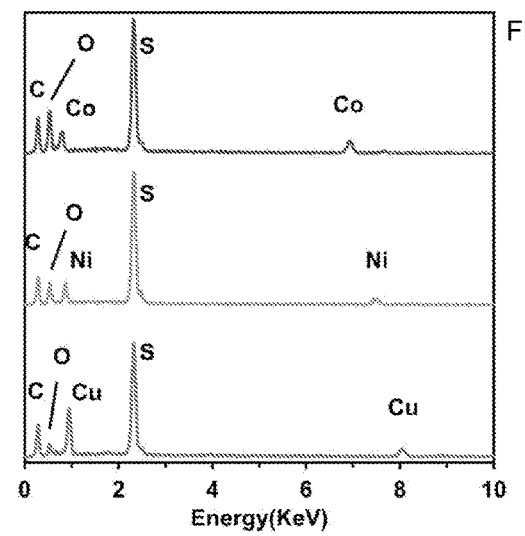
FIG. 6C shows Energy-Dispersive X-Ray Spectroscopy of $M_3HHTP_2$ MOFs showing the elemental composition of solid-state materials.
Figure 6D:
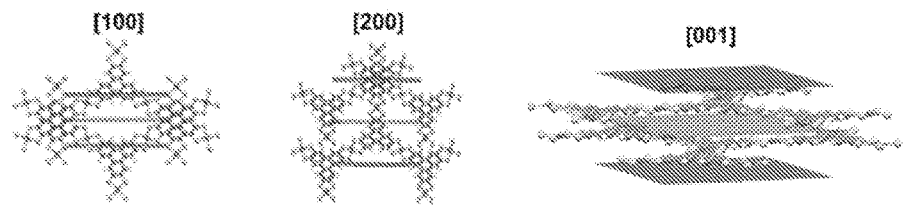
FIG. 6D shows planes [100], [200], and [001] in crystal lattices. Also shown are $Cu_3HTTP_2$ in different packing modes, including slipped parallel (FIG. 6E) and staggered (FIG. 6F) modes.
Figures 6E, 6F:
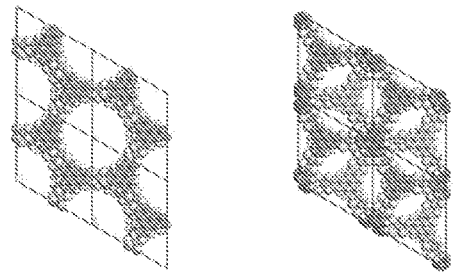
Figure 7:
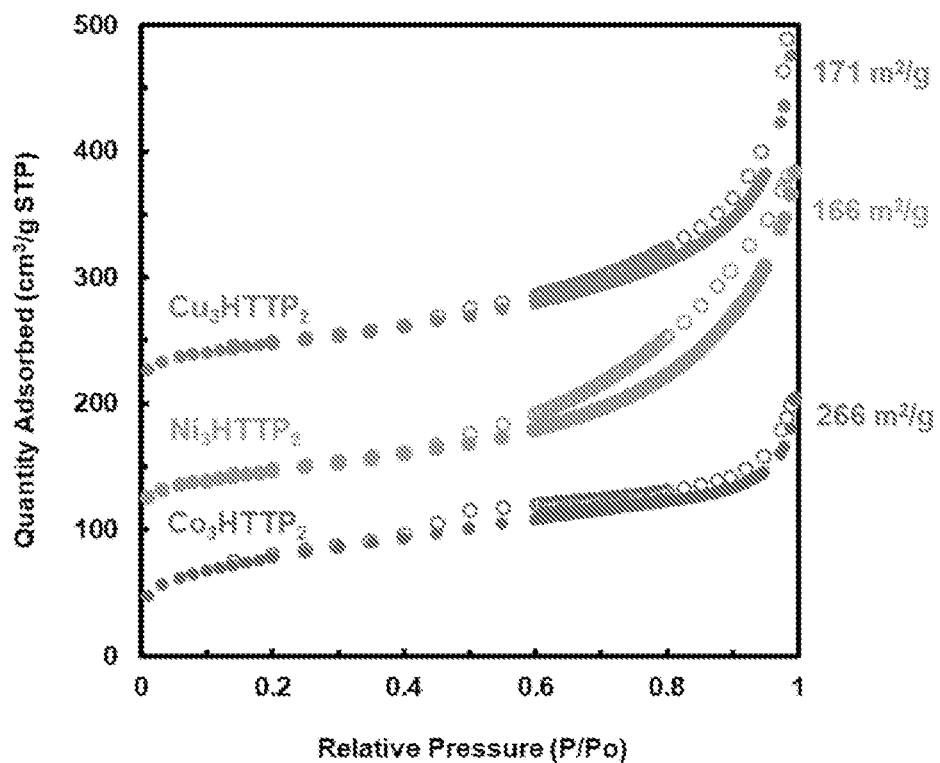
FIG. 7 shows nitrogen adsorption isotherms at 77 K for $Ni_3HTTP_2$, $Cu_3HTTP_2$, and $Co_3HTTP_2$. All samples were degassed at 120° C. under vacuum for 24 hours prior to the surface area analysis.
Figure 8A:
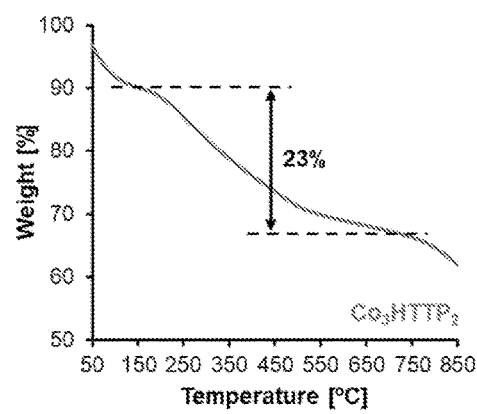
FIG. 8 shows thermal gravimetric analysis (TGA) curves for $Co_3HTTP_2$ (FIG. 8A), $Ni_3HTTP_2$ (FIG. 8B), $Cu_3HTTP_2$ (FIG. 8C), and HTTP ligand (FIG. 8D). $M_3HTTP_2$ MOFs are represented by a solid line.
Figure 8B:
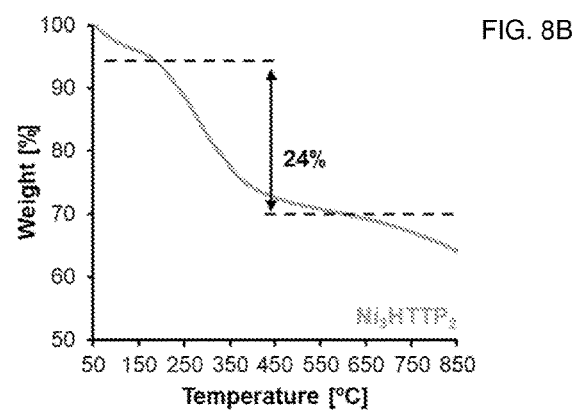
Figure 8C:
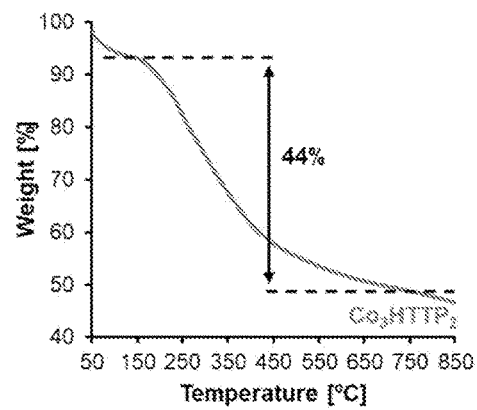
Figure 8D:
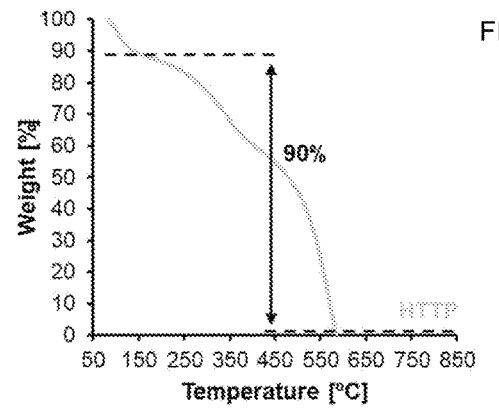
Figure 9A:
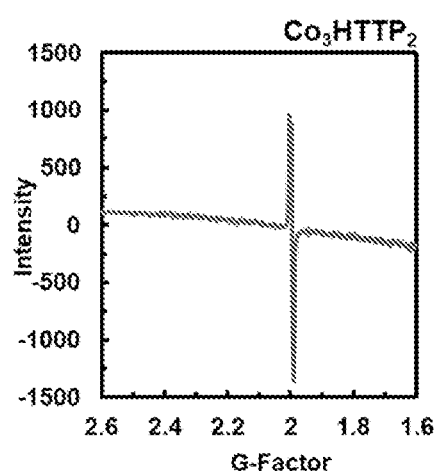
FIG. 9 shows electron paramagnetic resonance (EPR) spectra of $Co_3HTTP_2$ (FIG. 9A), $Ni_3HTTP_2$ (FIG. 9B), $Cu_3HTTP_2$ PCPs (FIG. 9C), and HTTP ligand (FIG. 9D) at 77 K. Strong paramagnetic behavior was observed for all studied $M_3HTTP_2$ PCPs with the metal-centered radical present in $Cu_3HHTP_2$ PCP (G-factor: 2.04) and ligand based radicals observed for both $Co_3HHTP_2$ and $Ni_3HHTP_2$ materials (G-factors: 2.01). Small EPR signal recorded for the HTTP (G-factor: 2.04) ligand may indicate the presence of trace levels of metallic impurities from the synthesis.
Figure 9B:
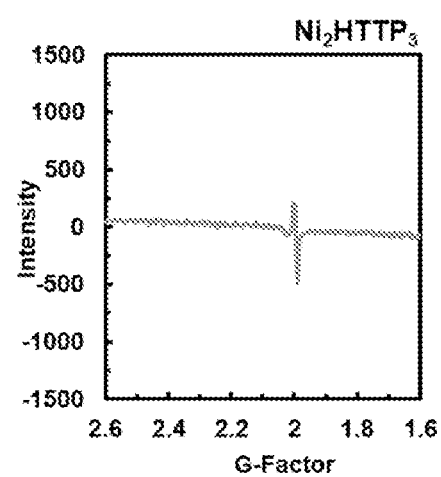
Figure 9C:
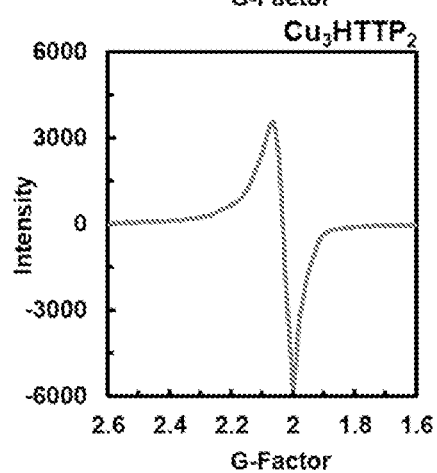
Figure 9D:
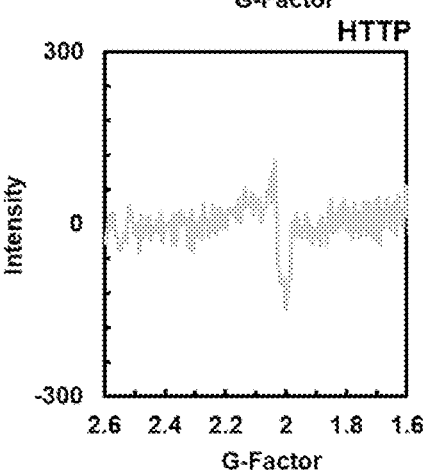

Scanning Electron Microscopy (SEM) revealed non-uniform nanoscale morphologies of PCPs (FIG. 6A). Powder X-Ray diffraction (pXRD) showed limited crystallinity, with broad peak at 2θ=9.0°, consistent with the pore dimensions of 2.0 nm. This peak was absent in the pXRD analysis of the HTTP-based molecular precursor (FIG. 6B). The Ni— and Cu— PCP analogs also showed a [001] peak at 2θ=21.5°, consistent with layered structure with an interlayer distance of 0.40 nm. The surface porosity from Brunauer-Emmett-Teller (BET) analysis ($N_2$, 77 K) was 171 $m^2/g$, 166 $m^2/g$, and 266 $m^2/g$ for $Cu_3HTTP_2$, $Ni_3HTTP_2$, and $Co_3HTTP_2$, respectively (FIG. 7).

Figure 10:
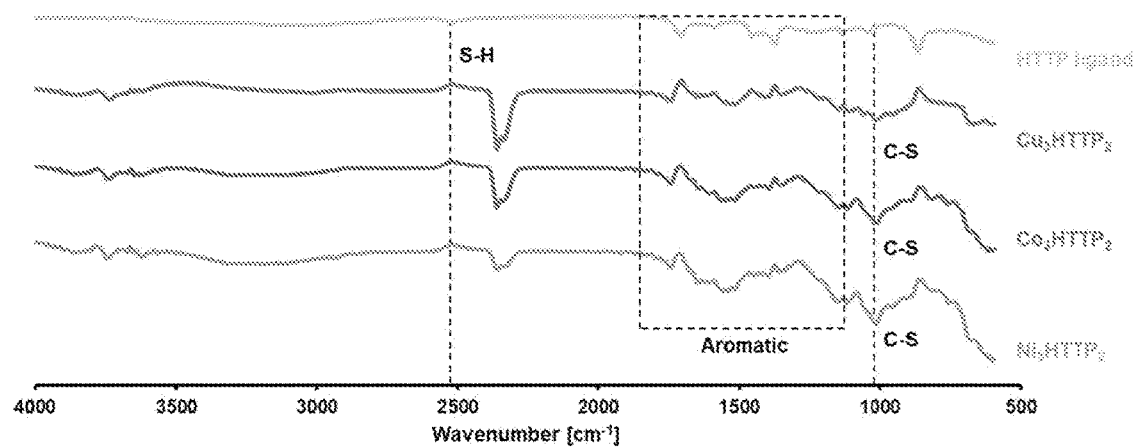
FIG. 10 shows attenuated total reflectance (ATR) spectra of powdered HTTP ligand (orange), $Cu_3HTTP_2$ (red), $Co_3HTTP_2$ (blue), and $Ni_3HTTP_2$ (green).

Thermal gravimetric analysis (TGA) revealed increased thermal stability of PCPs compared to the HTTP precursor (FIG. 8). Electron Paramagnetic Resonance (EPR) spectroscopy showed ligand-centered radicals in $Ni_3HTTP_2$ and $Co_3HTTP_2$, and a metal centered radical in $Cu_3HTTP_2$; limited paramagnetism was observed for the HTTP ligand (FIG. 9). Attenuated total reflectance infrared spectroscopy (ATR-IR) confirmed the disappearance of the S—H stretching vibration at 2510 $cm^{-1}$ upon metal coordination (FIG. 10). Bulk conductivity of $2.4 \times 10^{-9}$, $3.6 \times 10^{-4}$, and $2.4 \times 10^{-8}$ S/cm for $Co_3HTTP_2$, $Ni_3HTTP_2$, and $Cu_3HTTP_2$, respectively, suggested reasonable ability for charge transport.

Figure 11A:
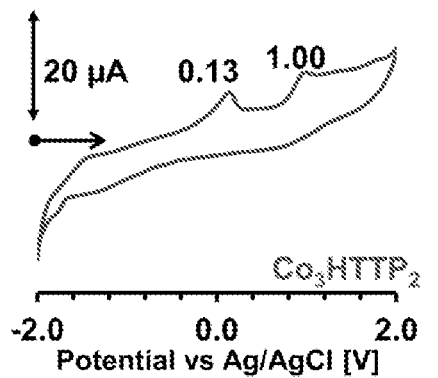
FIG. 11A shows cyclic voltammograms (CVs) for $Co_3HTTP_2$ in blue, $Ni_3HTTP_2$ in green, and $Cu_3HTTP_2$ in red; scan rate: 10 mV/s.
Figure 11A:
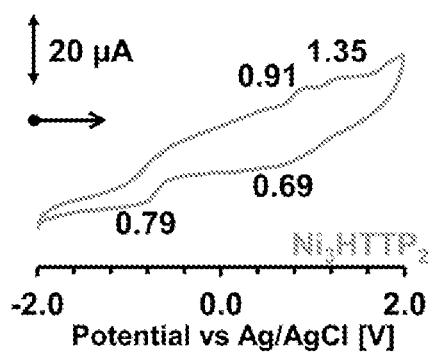
Figure 11A:
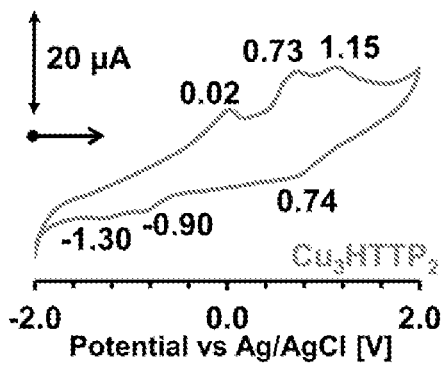
Figure 12:
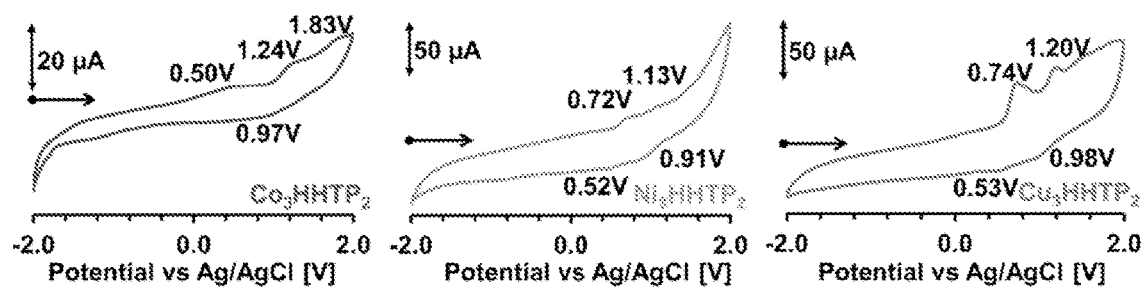
FIG. 12 shows cyclic voltammograms of $M_3HHTP_2$ MOFs in organic solution. Scan rate: 10 mV/s, 0.1 mM $TBAPF_6$ in $CH_3CN$, 3 mm glassy carbon working electrode, under nitrogen atmosphere. Scan directions are indicated by arrows.

Cyclic voltammetry (CV) studies in a non-aqueous environment (−2.0 V to +2.0 V in MeCN) established the electroactive nature the materials in this study (FIG. 11A and FIG. 12). Applicants identified the presence of three distinct spectral features: i) two redox bands at oxidative potentials larger than +0.70 V; ii) one redox transition at potentials lower than +0.20 V on the anodic scan; and iii) lack of well-defined redox bands during the cathodic scans.

Figure 13:
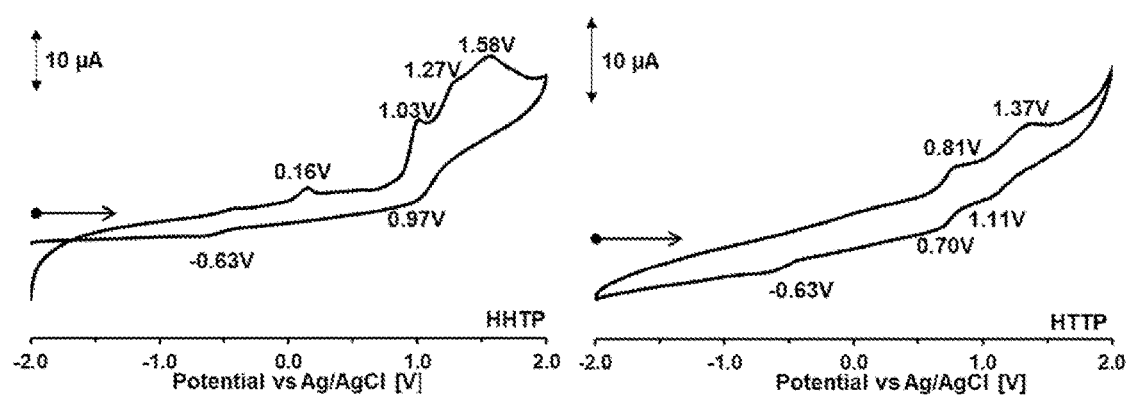
FIG. 13 shows cyclic voltammograms of HHTP (left) and HTTP (right) ligands. Scan rate: 100 mV/s, 0.1 mM $TBAPF_6$ in $CH_3CN$, 3 mm glassy carbon working electrode, under nitrogen atmosphere. The arrow indicates scan direction.
Figure 14:
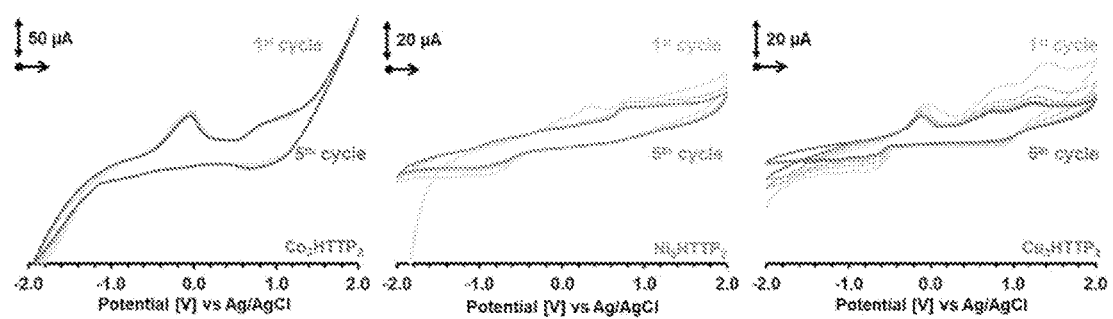
FIG. 14 shows cyclic voltammograms of $M_3HTTP_2$ PCPs in MeCN. Light to dark coloration indicates the progression of the voltammetric experiment (scans 1 to 5). The observed changes in peak intensity upon cycling may be attributed to the electrochemical equilibration of drop-cast PCP. Scan rate: 10 mV/s, 0.1 mM $TBAPF_6$ in $CH_3CN$, 3 mm glassy carbon working electrode, under nitrogen atmosphere. Scan directions are indicated by horizontal arrows.

Redox transitions found at higher oxidative potentials (>+0.70 V) closely matched the redox bands observed for the organic precursors used to produce $M_3HTTP_2$ or $M_3HHTP_2$ PCPs (FIG. 11A and FIG. 12-FIG. 13). The distinct negative shift compared to the free ligand in the oxidation potential of the PCPs may indicate that the electron transfer is largely stabilized in the PCPs. The presence of redox transitions found at lower oxidative potentials (<+0.20 V) in FIG. 11A could originate from: i) redox activity of the metal centers within the PCPs; ii) co-existence of multiple redox processes due to defects (e.g., exposed leading edges, such as open metal and ligand sites in the framework); and iii) redox active impurities permanently embedded within the framework. The lack of well-defined peaks on the cathodic scan may indicate irreversibility of the electrochemical system, or that the electron transfer process is followed directly by a chemical reaction in which non-redox active species are formed. $M_3HTTP_2$ PCPs were stable to at least five CV cycles (FIG. 14).

Figure 11B:
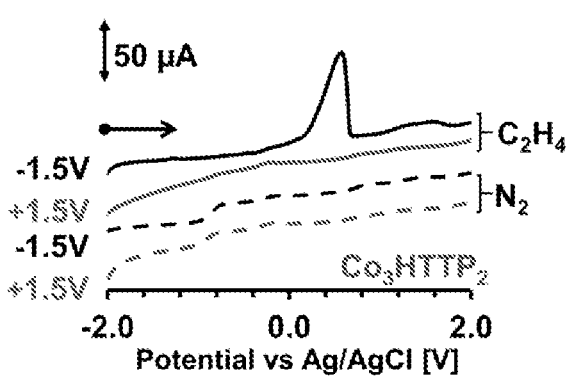
FIG. 11B shows linear sweep voltammograms (scan rate 50 mV/s) in the presence of dissolved $N_2$ (dashed lines) and $C_2H_4$ (solid lines). PCPs are either pre-oxidized (red) or pre-reduced (black). All measurements were performed in 0.1 mM $TBAPF_6$ in MeCN under $N_2$ (5 scans). 3 mm diameter glassy carbon electrode, platinum wire, and Ag/AgCl electrodes were used as the working, counter, and reference electrodes, respectively.
Figure 11B:
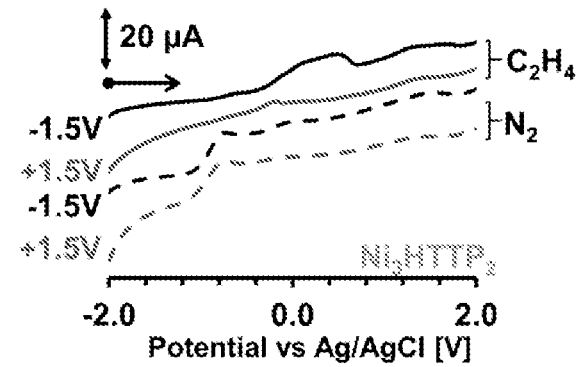
Figure 11B:
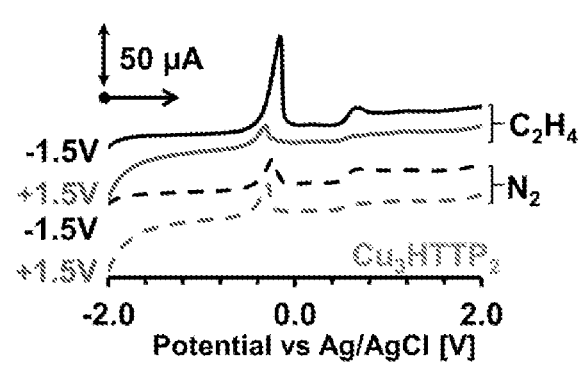
Figure 15A:
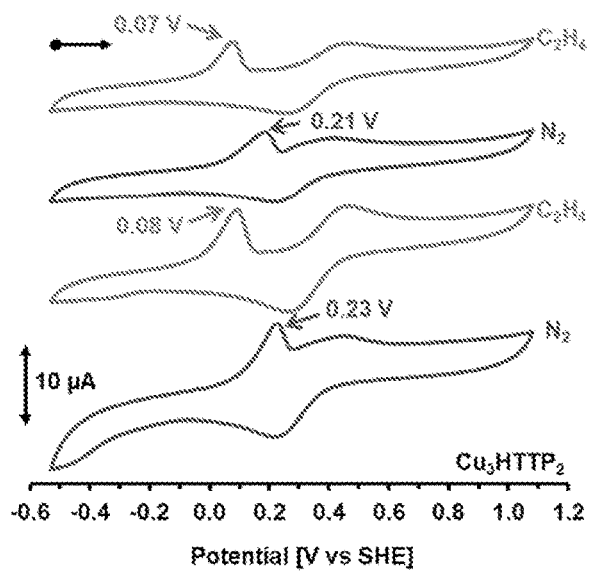
FIG. 15 shows CVs of $Cu_3HTTP_2$ PCPs in aqueous solution while switching in between: ethylene and nitrogen (FIG. 15A) and argon and nitrogen (FIG. 15B). Scan rate: 100 mV/s, 0.1 M KCl in water. 3 mm glassy carbon working electrode, platinum wire and Ag/AgCl electrodes were used as the working, counter and reference electrodes, respectively. Nafion was used for attaching $Cu_3HTTP_2$ to the working electrode. Arrows indicate scan direction.
Figure 15B:
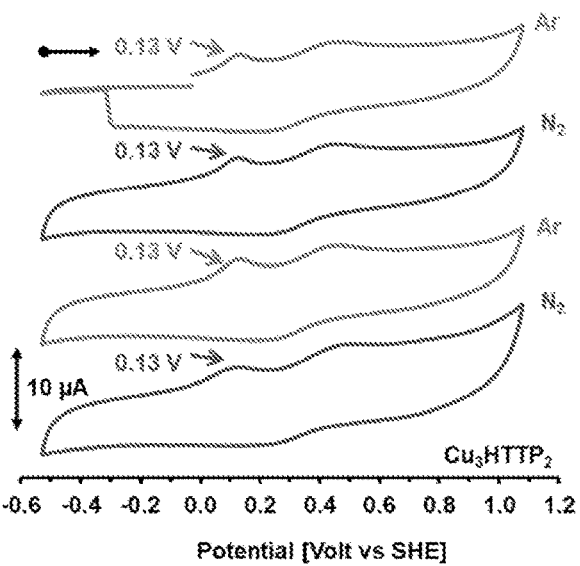
Figure 16:
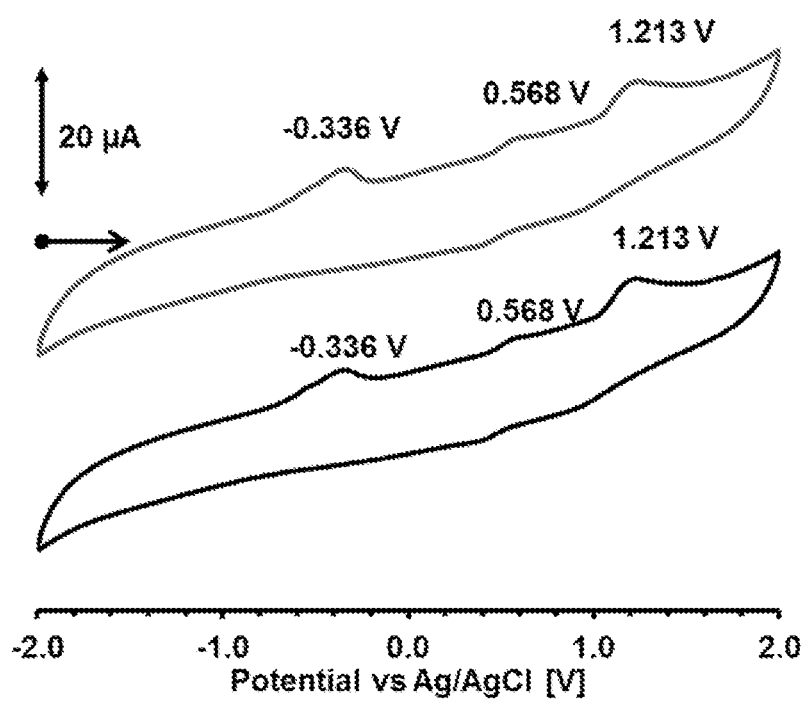
FIG. 16 shows CVs of $Cu_3HTTP_2$ PCPs in 0.1 M $TBAPF_6$ in MeCN in the absence (black) and presence (red) of ethylene. Scan rate: 50 mV/s, 0.1 mM $TBAPF_6$ in $CH_3CN$. 3 mm glassy carbon working electrode, platinum wire and Ag/AgCl electrodes were used as the working, counter and reference electrodes, respectively. Arrows indicate scan direction.
Figure 17A:
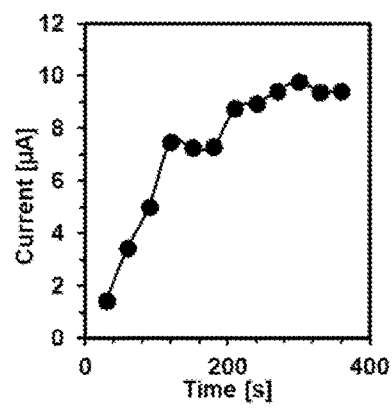
FIG. 17 shows the effect of the accumulation time (−1.5 V) on the peak current of $Ni_3HTTP_2$ (FIG. 17A), $Cu_3HTTP_2$ (FIG. 17B) and $Co_3HTTP_2$ (FIG. 17C) in the presence of ethylene. Scan rate: 100 mV/s, 0.1 mM $TBAPF_6$ in $CH_3CN$. 3 mm glassy carbon working electrode, platinum wire and Ag/AgCl electrodes were used as the working, counter and reference electrodes, respectively.
Figure 17B:
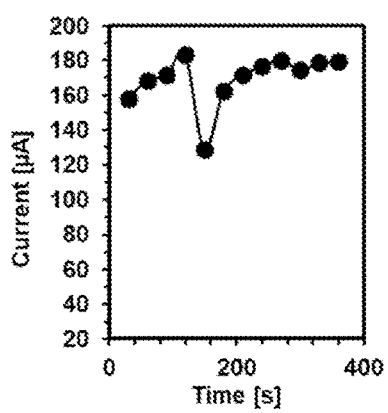
Figure 17C:
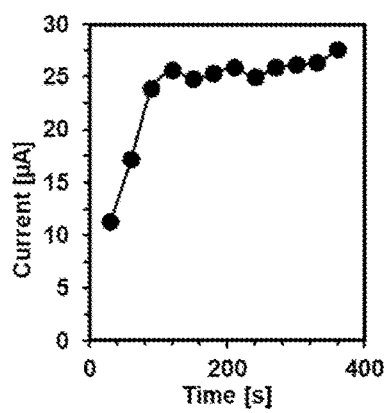
Figure 18A:
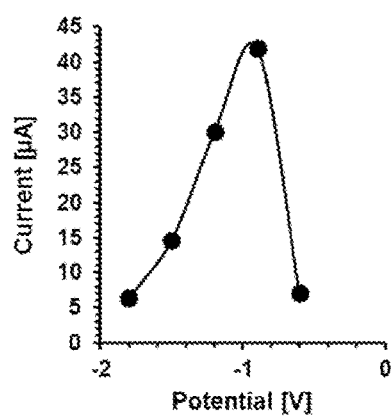
FIG. 18 shows the effect of the accumulation potential on the peak current of $Ni_3HTTP_2$ (FIG. 18A), $Cu_3HTTP_2$ (FIG. 18B) and $Co_3HTTP_2$ (FIG. 18C) in the presence of ethylene. Scan rate: 100 mV/s, 0.1 mM $TBAPF_6$ in $CH_3CN$. 3 mm glassy carbon working electrode, platinum wire (0.1 mm diameter) and Ag/AgCl electrodes were used as the working, counter and reference electrodes, respectively.
Figure 18B:
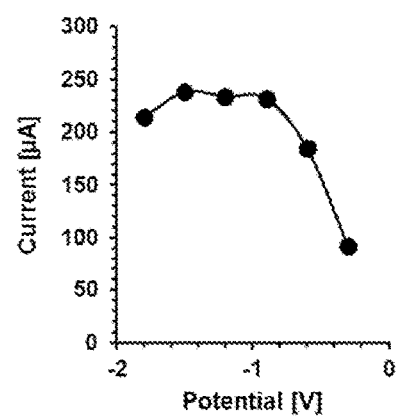
Figure 18C:
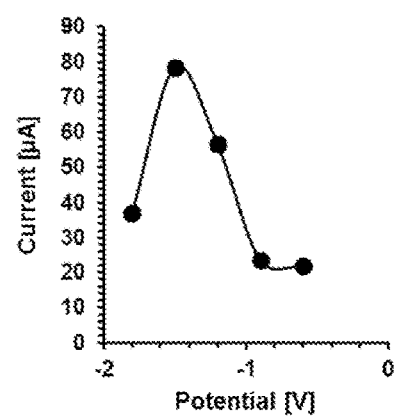
Figure 19A:
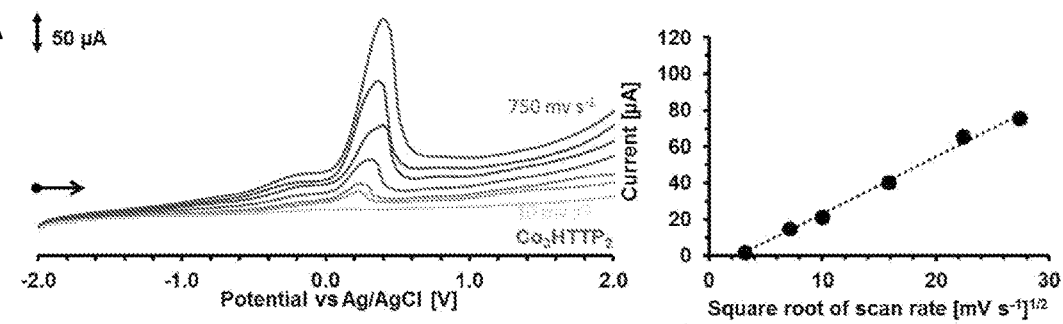
FIG. 19 shows scan rate dependence on the oxidation peaks of $Co_3HTTP_2$ (FIG. 19A), $Ni_3HTTP_2$ (FIG. 19B), and $Cu_3HTTP_2$ (FIG. 19C) MOFs in the presence of ethylene in 0.1 M $TBAPF_6$ in $CH_3CN$. Studied range: −0.01-1 V/s. 3 mm diameter glassy carbon working electrode, platinum wire and Ag/AgCl electrodes were used as the working, counter and reference electrodes, respectively. Arrows indicate scan direction.
Figure 19B:
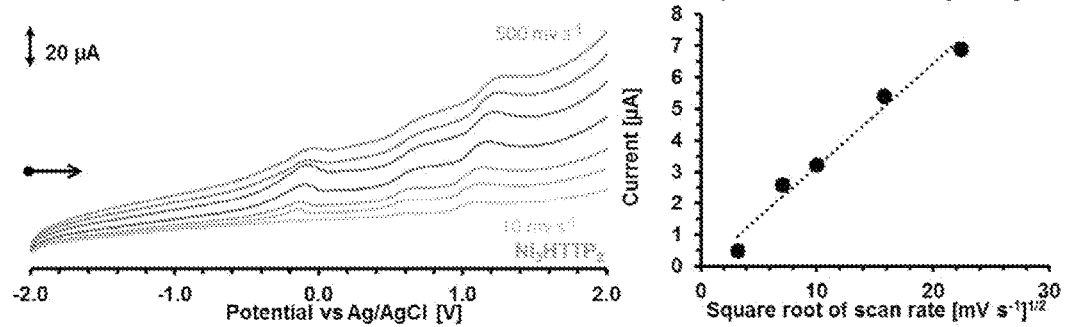
Figure 19C:
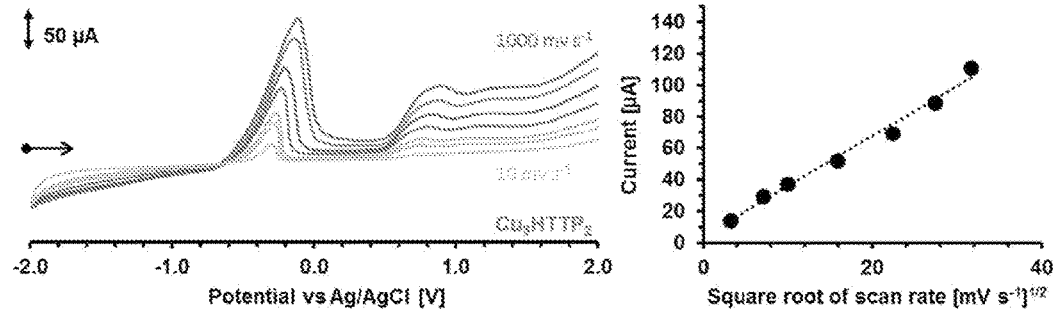

Next, Applicants proceeded to examine the interactions of PCPs with $C_2H_4$ in solution (FIG. 11B and FIG. 15-FIG. 16). Due to limited solubility of ethylene in organic and aqueous solvents (~1 mM), Applicants employed a pre-concentration step to enhance the electrochemical response (FIG. 17-FIG. 18 and FIG. 19). FIG. 11B compares the linear sweep voltammetry (LSV) responses for the $M_3HTTP_2$ materials immobilized on glassy carbon electrodes after 6 min accumulation time at −1.5 V and +1.5 V under $N_2$ and $C_2H_4$ in MeCN. In the presence of $C_2H_4$, pre-concentration at −1.5 V led to a notable increase in peak current intensity (FIG. 11B, solid black line). Reversing the potential from −1.5 V to +1.5 V during pre-concentration diminished the peak current intensity (solid red line) to a level of being indistinguishable from the results in the presence of $N_2$ (dashed lines).

While the voltammetric response in FIG. 11B suggested the presence of $C_2H_4$/$M_3HTTP_2$ interactions, Applicants employed $M_3HHTP_2$ MOFs to gain additional insight into the mechanistic details of this electrochemically-driven transformation. This control can: i) probe the possibility of ethylene capture through the formation of the π-complex with the metal center in the PCPs; and ii) examine the role of chalcogen atoms (S vs O) in the capture process. To test these possibilities, Applicants held the electrode with dropcast layer of $M_3HHTP_2$ for 120 seconds at either −1.5 V or +1.5 V in $N_2$ or $C_2H_4$ (FIG. 20). In each case, $M_3HHTP_2$ controls did not produce a change in response. Applicants, therefore, conclude that the similarities in LSV response for all HTTP-based materials reinforce that S-atoms of the metal bis(dithiolene) complex are critical to the observed electrochemical performance in the presence of $C_2H_4$.

The results from solution-based electrochemical measurements are subject to complications due to several experimental factors, including: i) effect of solvent; ii) choice of electrolyte; iii) solubility of gas; and iv) requirement for three electrode configuration, making electrochemical capture of ethylene in solution a complex process. Applicants proceeded to develop a strategy that overcomes the complexities by integrating each $M_3HTTP_2$ PCP into two types of solid-state devices (FIG. 21): i) PCP-coated conductive slides (2.5 cm×1.5 cm with 5 mg loading of $M_3HTTP_2$); and ii) the compressed pellet (6 mm diameter, 62 mg, 1.45 mm thickness). Applicants reasoned that stimulating these forms of material with applied potential would enable electrically-actuated reactivity of the PCP with $C_2H_4$.

Figure 22A:
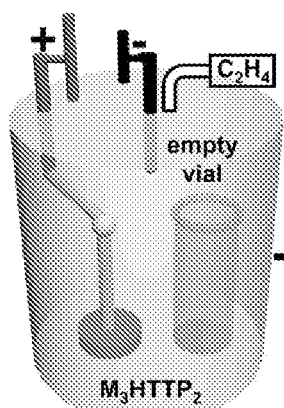
FIG. 22A shows the setup comprises the PCPs positioned under ethylene atmosphere (~1 atm) in a sealed container. Applied electrical potential (+2.0 V) to the material facilitates ethylene capture.
Figure 22B:
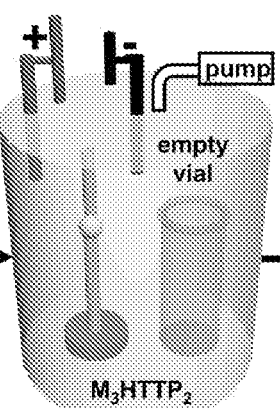
FIG. 22B shows switching off the power, and evacuating at $1.5 \times 10^{-3}$ Torr removes all unbound ethylene.
Figure 22C:
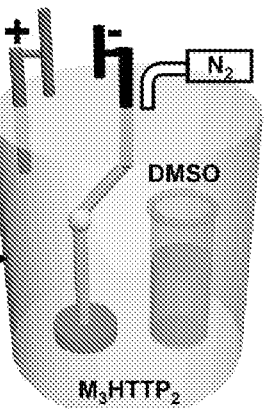
FIG. 22C shows refilling of the container with $N_2$, and addition of deuterated dimethyl sulfoxide (DMSO-$d_6$) enables monitoring of electrochemical release by NMR. Subsequent reduction at −2.0 V promotes ethylene release.
Figure 22D:
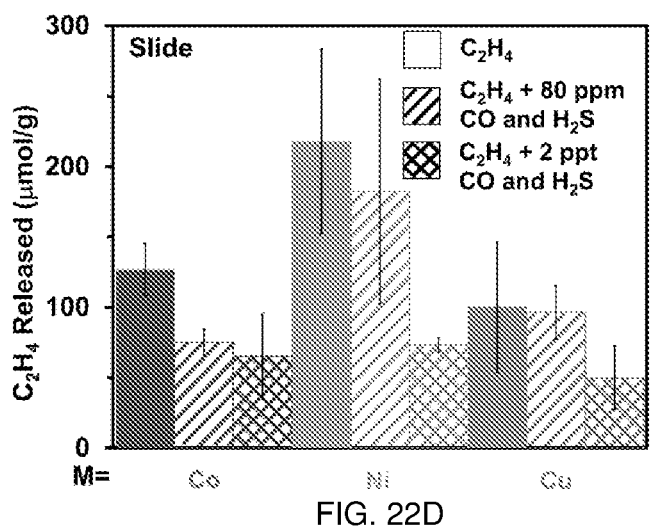
FIGS. 22D-22E show the amount of ethylene quantified in the electrochemical capture/release experiment in the absence and presence of interferents (80 ppm and 2 ppt of CO and $H_2S$) by thin films (FIG. 22D) and pellets (FIG. 22E).
Figure 22E:
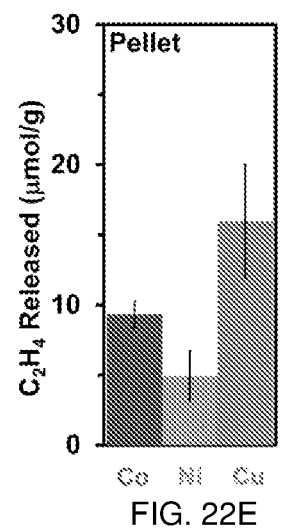
Figure 23:
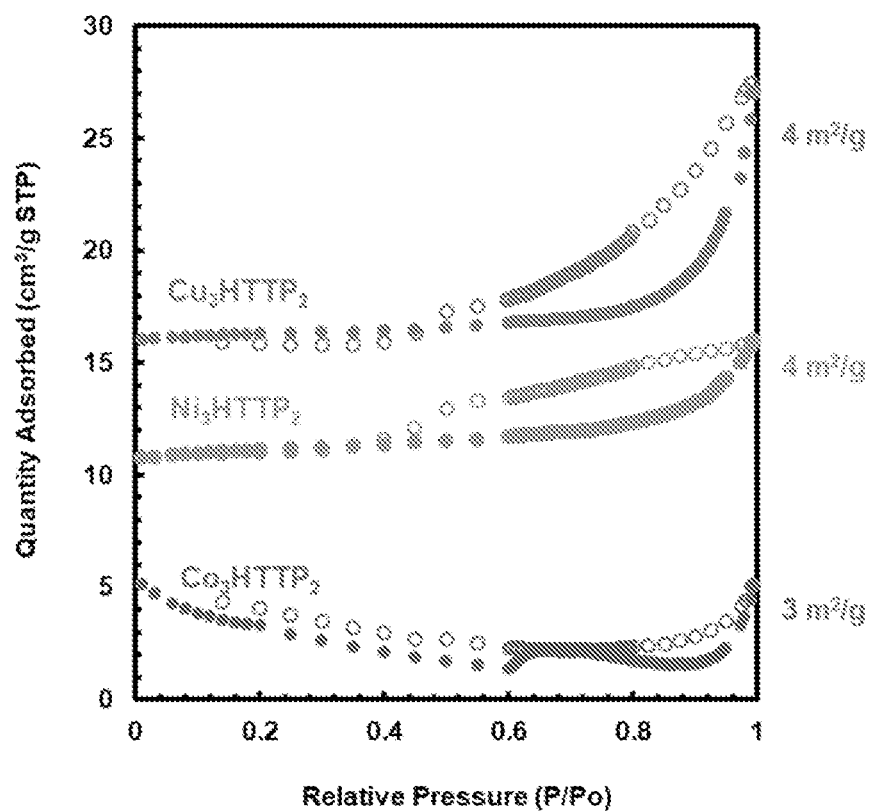
FIG. 23 shows nitrogen adsorption isotherms collected at 77 K for $Ni_3HTTP_2$, $Cu_3HTTP_2$ and $Co_3HTTP_2$ compressed pellets. All samples were degassed at 120° C. under vacuum for 24 hours prior to the surface area analysis.

Capture of ethylene was achieved by delivering electrical potential (+2.0 or −2.0 V) to the solid-state device. Applicants then used Henry's law for gas-liquid partitioning to quantify the amount of released $C_2H_4$ by NMR. Only electrochemically oxidized $M_3HTTP_2$ PCPs were capable of capturing $C_2H_4$ (FIG. 22D-E). Despite the 10-fold difference in the amounts of electrochemically-captured $C_2H_4$ in µmol/g captured by thin films (FIG. 22D) as compared to pellets (FIG. 22E), the similarity in uptake in moles (300-1100 nmol) by these two devices (Table 4-Table 5, detailed below in Example 1.45) suggested that the exposed surface area (rather than the bulk) dominated the capture process. Analysis of pellets by BET (FIG. 23) showed ~30 times reduction in porosity upon compression, and confirmed the role of surface-dominated process.

Figure 28:
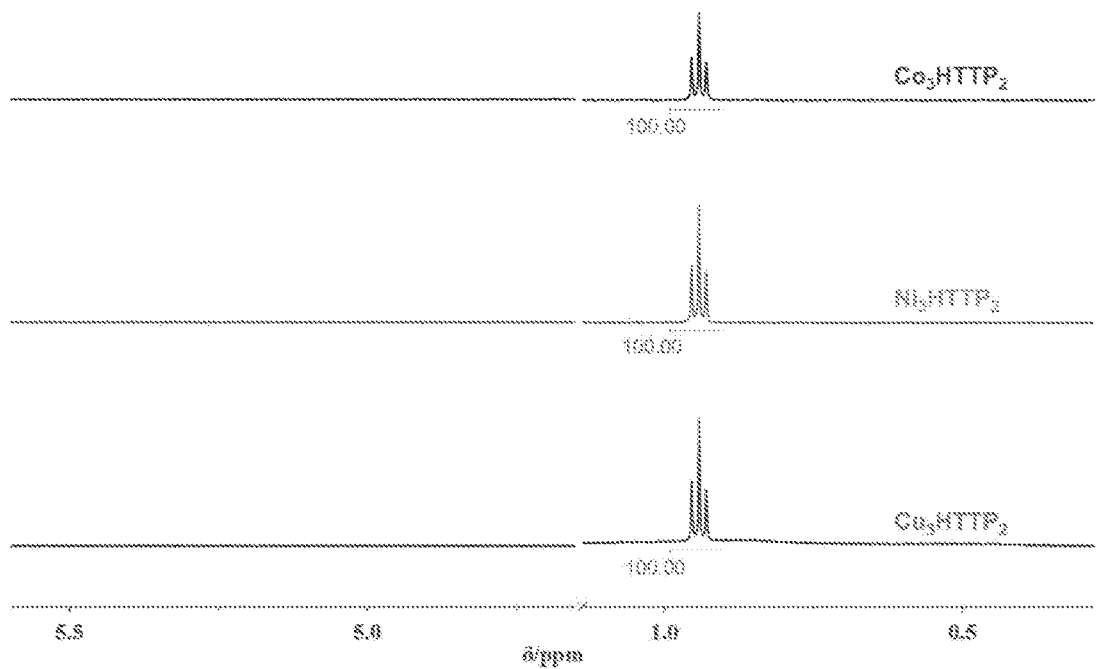
FIG. 28 shows $^1H$ NMR of DMSO-$d_6$ after solid-state ethylene capture by $Co_3HTTP_2$, $Ni_3HTTP_2$ and $Cu_3HTTP_2$ PCPs compressed pellets. Experimental conditions: 60 min exposure to ethylene without the application of potential followed by the exposure to vacuum for 120 min. Reduction step was performed for 60 min at −2.0 V to release the ethylene from the $M_3HHTP_2$ coated slides.
Figure 29:
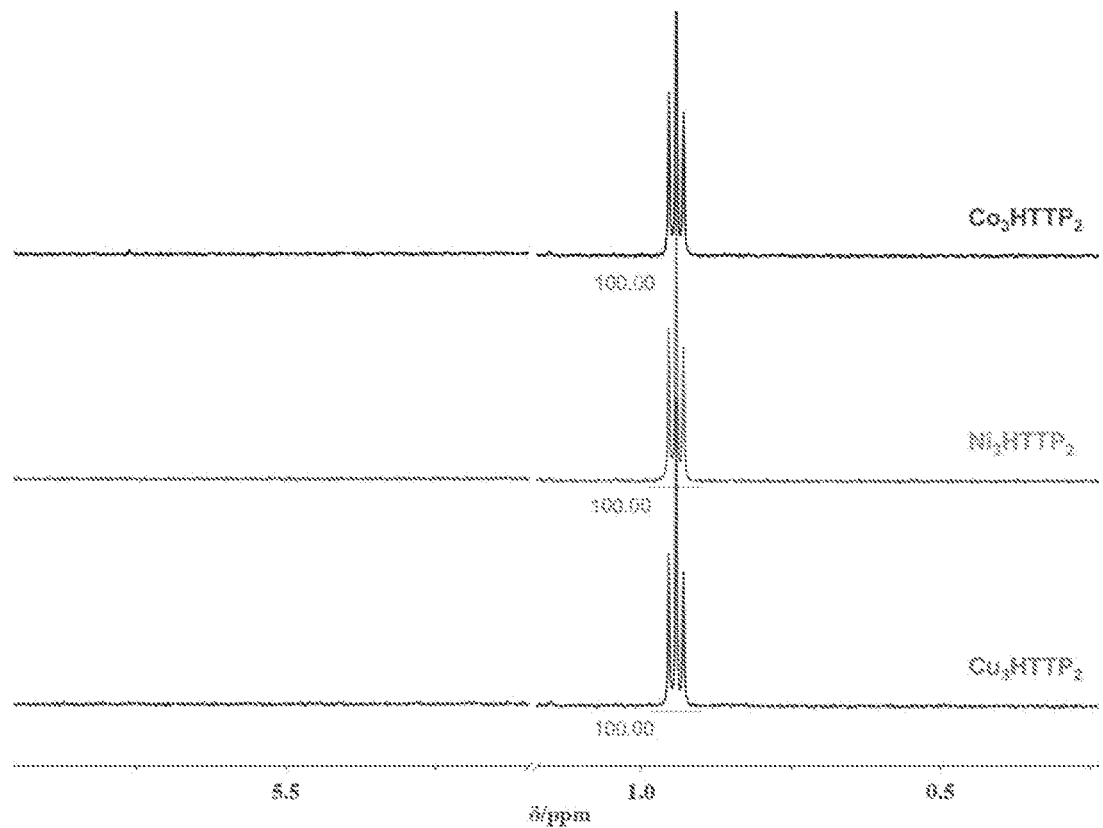
FIG. 29 shows $^1H$ NMR of DMSO-$d_6$ after solid-state ethylene capture by $Co_3HTTP_2$, $Ni_3HTTP_2$ and $Cu_3HTTP_2$ PCPs compressed pellets. Experimental conditions: 60 min exposure to ethylene without the application of potential followed by the exposure to vacuum for 120 min. During the reduction step, no electrical potential was applied to the samples prior to the NMR analysis.
Figure 30:
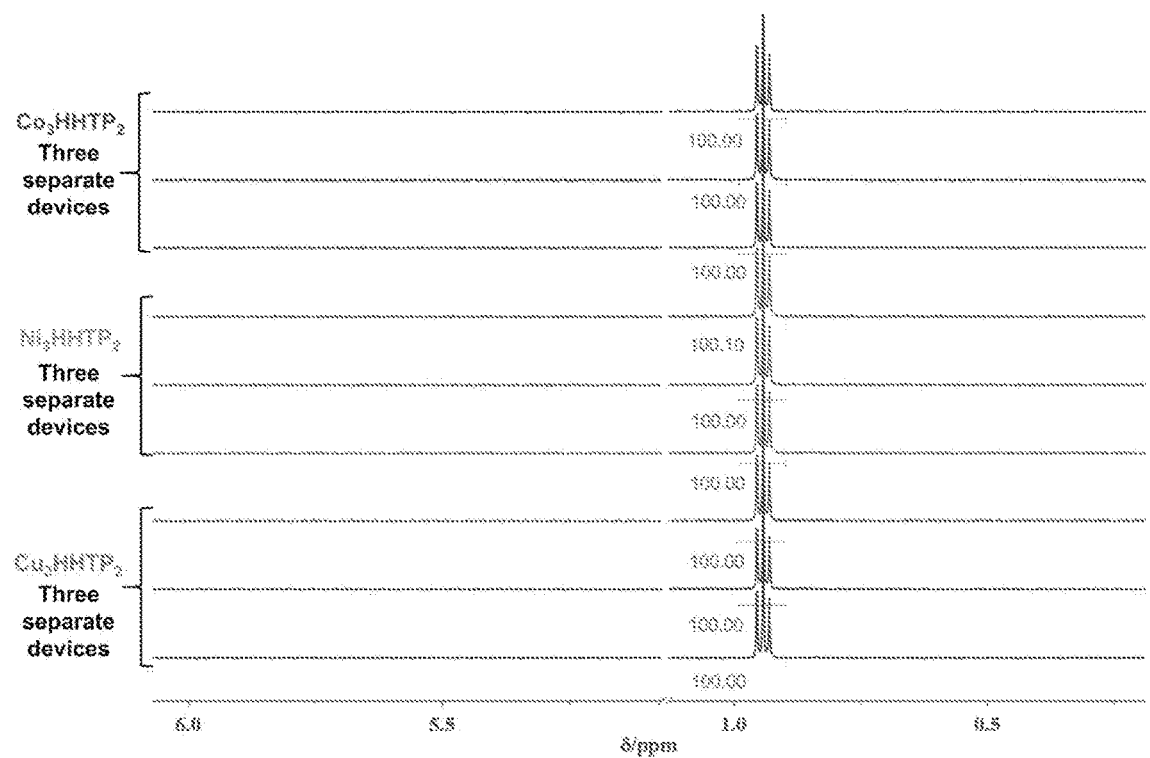
FIG. 30 shows $^1H$ NMR of DMSO-$d_6$ after solid-state ethylene capture by $Co_3HHTP_2$, $Ni_3HHTP_2$ and $Cu_3HHTP_2$ PCPs compressed pellets. Experimental conditions: 60 min oxidation at +2.0 V in the presence of ethylene, after the exposure to vacuum for 120 min and followed by the reduction for 60 min at −2.0 V to release the ethylene from the $M_3HHTP_2$ pellets. All measurements were carried out using four separate devices made of $M_3HHTP_2$ PCPs.
Figure 31:
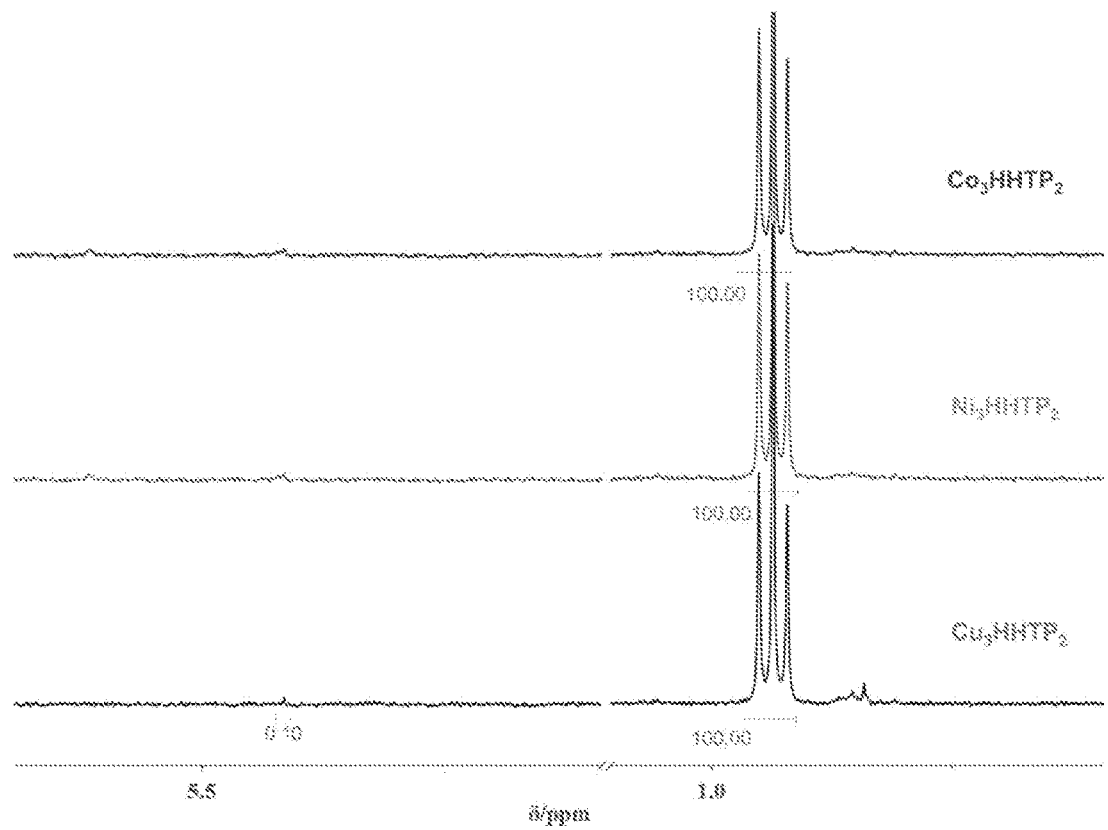
FIG. 31 shows $^1H$ NMR of DMSO-$d_6$ after solid-state ethylene capture by $Co_3HHTP_2$, $Ni_3HHTP_2$, and $Cu_3HHTP_2$ PCPs drop-casted layer. Experimental conditions: 60 min oxidation at +2.0 V in the presence of ethylene, after the exposure to vacuum for 120 min and followed by the reduction for 60 min at −2.0 V to release the ethylene from the $M_3HHTP_2$ coated slides.
Figure 32:
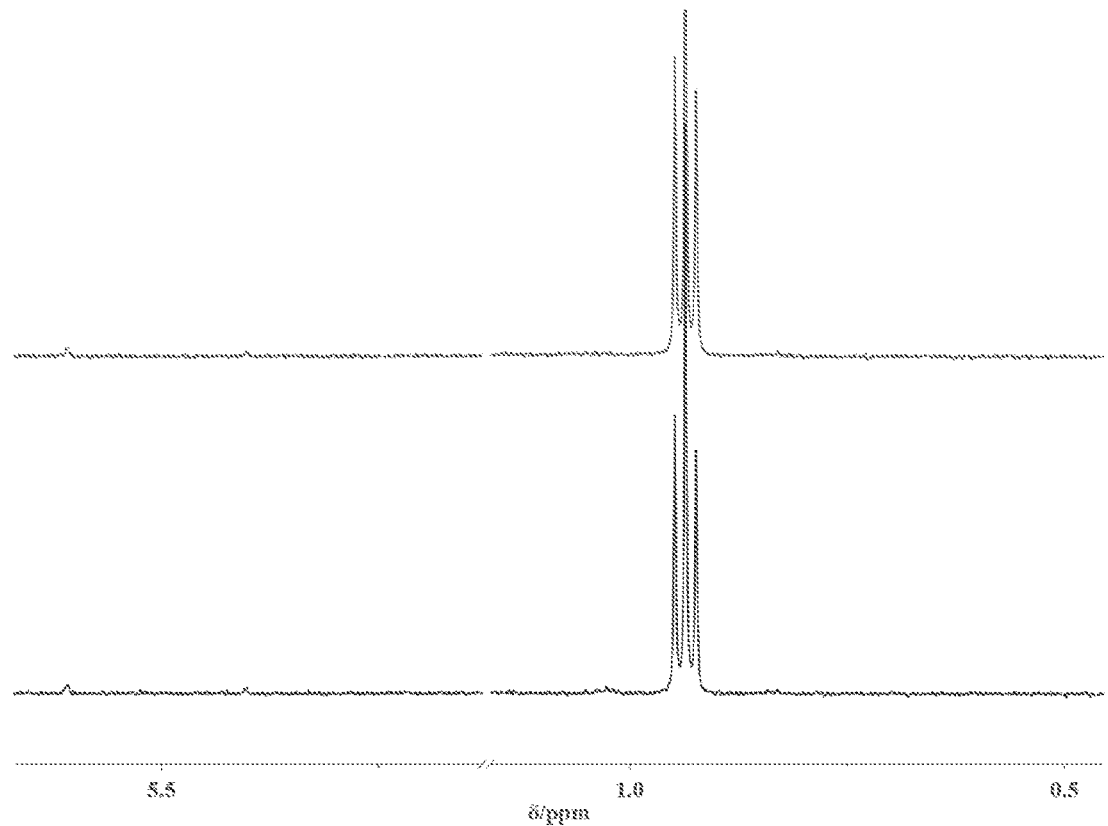
FIG. 32 shows $^1H$ NMR of DMSO-$d_6$ after solid-state ethylene capture by the compressed pellet (top) and drop-casted layer (bottom) of HTTP ligand. Experimental conditions: 60 min oxidation at +2.0 V in the presence of ethylene, after the exposure to vacuum for 120 min and followed by the reduction for 60 min at −2.0 V to release the ethylene from the HTTP ligand compressed pellet and drop-casted layer.

The application of electrical potential was essential for driving the capture process in the solid-state. No $C_2H_4$ capture was detected in the absence of applied potential (+2.0 V or/and −2.0 V), or the case of omission of the oxidation or reduction steps (FIG. 24-FIG. 29). Two control materials—$M_3HHTP_2$ MOFs or HTTP ligand—did produce observable capture (FIG. 30-FIG. 32). These findings confirm the essential role of metal bis(dithiolene) complex in the electrochemically-driven capture.

The presence of gaseous inhibitors above 10 ppm can poison metal-based catalysts in $C_2H_4$ purification. Applicants thus evaluated the solid-state performance of $M_3HTTP_2$ PCPs for $C_2H_4$ capture in the presence of interfering poisoning agents ($H_2S$ and CO). Applicants exposed each of the PCPs to a mixture of gases comprising $H_2S$, CO (80 ppm or 2 ppt), and ethylene for 60 min at +2.0 V (applied potential), and then measured the amount of ethylene recovered in the NMR solvent immediately after the release step (−2.0 V for 60 min). Remarkably, the presence of 80 ppm of gaseous poisons reduced the performance of thin films only by 40%, 15%, and 3% for $Co_3HTTP_2$, $Ni_3HTTP_2$, and $Cu_3HTTP_2$ PCPs (FIG. 22D). Even in the presence of 2 ppt of $H_2S$ and CO, the materials still maintained 35-50% of their function (FIG. 22D and Table 4-Table 5, detailed below in Example 1.45). Together, these findings indicate that the $M_3HTTP_2$ materials retain their function in a complex environment, and resist poisoning by interferents.

In conclusion, this Example describes the first experimental implementation of PCPs to achieve electrochemically-driven capture and release of ethylene in solution and at the solid-gas interface. This method has five distinct advantages for electrochemically-controlled molecular capture: i) it is compatible both with the solution-phase capture in the presence of electrolytes and with the direct solid-state capture in the absence of electrolytes; ii) it is resistant to poisoning by reactive gases, such as CO and $H_2S$; iii) it enables pre-concentration of the olefin within a PCP; iv) it employs relatively low overpotentials in the range of −2.0 V to +2.0 V; and v) it utilizes a class of modular porous materials that can be further optimized for performance through strategic design.

The observed unoptimized $C_2H_4$ uptake efficiency of $M_3HTTP_2$ PCPs drop-casted films (ranging from 0.10-0.22 mmol/g, Table 4, detailed below in Example 1.45) is approximately one order of magnitude below FeMOF-74 (6.8 mmol/g at 1 bar) and SIFSIX-1-Cu (8.5 mmol/g at 1 bar), and comparable to other microporous scaffolds. The distinguishing feature of the process presented herein is its compatibility with low pressure and ambient temperature.

Example 1.1

Chemicals and Instruments

Chemicals and solvents were purchased from Sigma Aldrich (St. Louis, Mo.), TCI (Portland, Oreg.), Fisher (Pittsburgh, Pa.), or Alfa Aesar (Tewksbury, Mass.) and used as received. Ethylene (99.99%) was bought from AirGas (Radnor, Pa.) and used as received. Scanning Electron Microscopy (SEM) and Energy Dispersive X-ray Spectroscopy (EDX) were performed using a Hitachi TM3000 SEM (Tokyo, Japan) equipped for X-ray microanalysis with a Bruker Edax light element Si(Li) detector (Billerica, Mass.). Powder X-ray diffraction (PXRD) measurements were performed with a Bruker D8 diffractometer equipped with a Ge-monochromated 2.2 kW (40 kV, 40 kA) CuKα ($\lambda$=1.54 Å) radiation source and a NaI scintillation counter detector (Billerica, Mass.). NMR spectra were recorded on a Bruker 500 or 600 MHz NMR spectrometer. EmStat MUX16 potentiostat (Palm Instruments BV, Netherlands) was used for electrochemical measurements. Attenuated Total Reflectance Infrared Spectroscopy (ATR-IR) was performed using FT/IR-6200 (Jasco). Nitrogen adsorption experiments were performed with a 3Flex Surface and Catalyst Characterization analyzer (Micromeritics, Norcross, Ga.). Electron Paramagnetic Resonance measurements were conducted using a Bruker BioSpin Gmbh spectrometer equipped with a standard mode cavity. X-ray photoelectron spectroscopy (XPS) experiments were conducted using a Physical Electronics Versaprobe II X-ray Photoelectron Spectrometer under ultrahigh vacuum (base pressure $10^{-10}$ mbar). The measurement chamber was equipped with a monochromatic Al (Kα) X-ray source. Both survey and high-resolution spectra were obtained using a beam diameter of 200 μm. The spectra were processed with CasaXPS software. Four-point probe measurements on the compressed $M_3HTTP_2$ PCPs pellets were carried out by Lucas Signatone Corporation (Gilroy, Calif.). Thermal Gravimetric Analysis (TGA) traces using a TA instruments TGA Q50 with platinum pans. Thermal Evaporator (Angstrom Engineering, Ontario, Canada) used to evaporate chromium (Chrome coated rod, Angstrom Engineering, Ontario, Canada) and gold (pellets, R.D. Mathis Company, 99.99% purity, Signal Hill, Calif.). Pellets were compressed using a 6 mm die (Across, International, Livingston, N.J.) and a desktop pellet press (Across International, Livingston, N.J.). Thin film solid-state capture utilized frosted glass slides (Electron Microscopy Science, Cat. #71867-01, Hatfield, Pa.).

Example 1.2

Synthesis of HTTP Ligand

Figure 33:
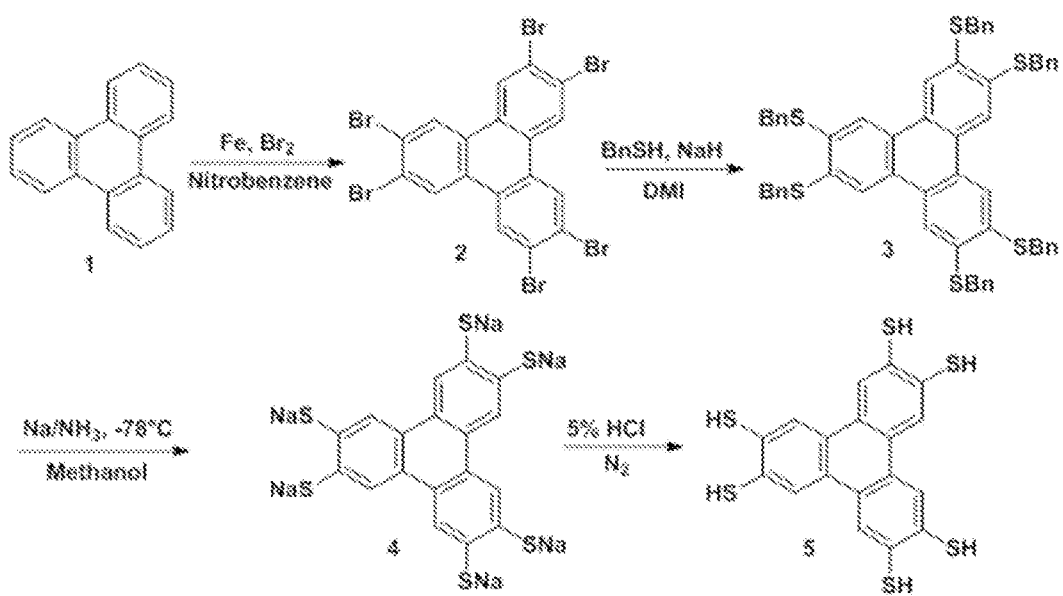
FIG. 33 shows a synthetic procedure for the preparation of 2,3,6,7,10,11-hexathioltriphenylene (HTTP).

Synthetic procedure for the preparation of 2,3,6,7,10,11-hexathioltriphenylene (HTTP) is illustrated in FIG. 33.

Example 1.3

Synthesis of 2,3,6,7,10,11-Hexabromotriphenylene (2)

To a solution of triphenylene (1, 1.07 g, 4.7 mmol) in nitrobenzene (40 mL) with iron powder (100 mg, 1.79 mmol) bromine (2.2 mL, 38.8 mmol) was slowly added over 15 minutes. The solution was then allowed to stand for 16 hours at room temperature. It was heated at 205° C. for 2 hours. The mixture was cooled to room temperature and mixed with diethyl ether (150 mL) and filtered. The crude white solid was washed by diethyl ether (3×30 mL) and acetone (3×10 mL). After drying in vacuo for 12 hours, 3.13 g of 2,3,6,7,10,11-hexabromotriphenylene (yield 95%) was collected. The product was used directly without characterization due to low solubility.

Example 1.4

Synthesis of 2,3,6,7,10,11-Hexabenzylmercaptyltriphenylene (3)

Sodium hydride (1.29 g, 53.8 mmol), which was washed with dry hexane before use, was introduced to a three-neck flask under nitrogen atmosphere. 90 mL of 1,3-dimethyl-2-imidazolidinone (DMI) was injected via a syringe. The flask was cooled to 0° C. Benzyl mercaptan (6.7 g, 54 mmol) was added slowly to avoid foaming. After stirring for 30 min at 0° C., 2,3,6,7,10,11-hexabromotriphenylene (2, 3.13 g, 4.5 mmol) was added in three portions. The reaction was stirred for another 10 mins at 0° C. and then allowed to react at room temperature for 12 hours. Toluene (300 mL) and a saturated $Na_2CO_3$ solution were then added. After discarding the aqueous phase, the organic phase was washed with saturated $Na_2CO_3$ solution (2×200 mL), and dried over $MgSO_4$. After evaporation of the solvents, the crude product was purified by column chromatography (silica gel, DCM/hexane=1/1 as eluent). The last fraction ($R_f$=0.2) was collected and then dried in vacuo. 2.10 g of white product was collected in 49% yield.

$^1$H NMR (CDCl$_3$, 600 MHz) $\delta_H$ 7.91 (s, 6H), 7.34 (m, 12H), 7.29 (m, 12H), 7.24 (m, 6H), 4.17 (s, 12H) ppm.

$^{13}$C NMR (CDCl$_3$, 600 MHz) $\delta_C$ 139.9, 139.6, 129.0, 128.7, 127.5, 127.4, 124.4, 38.7 ppm.

Figure 34:
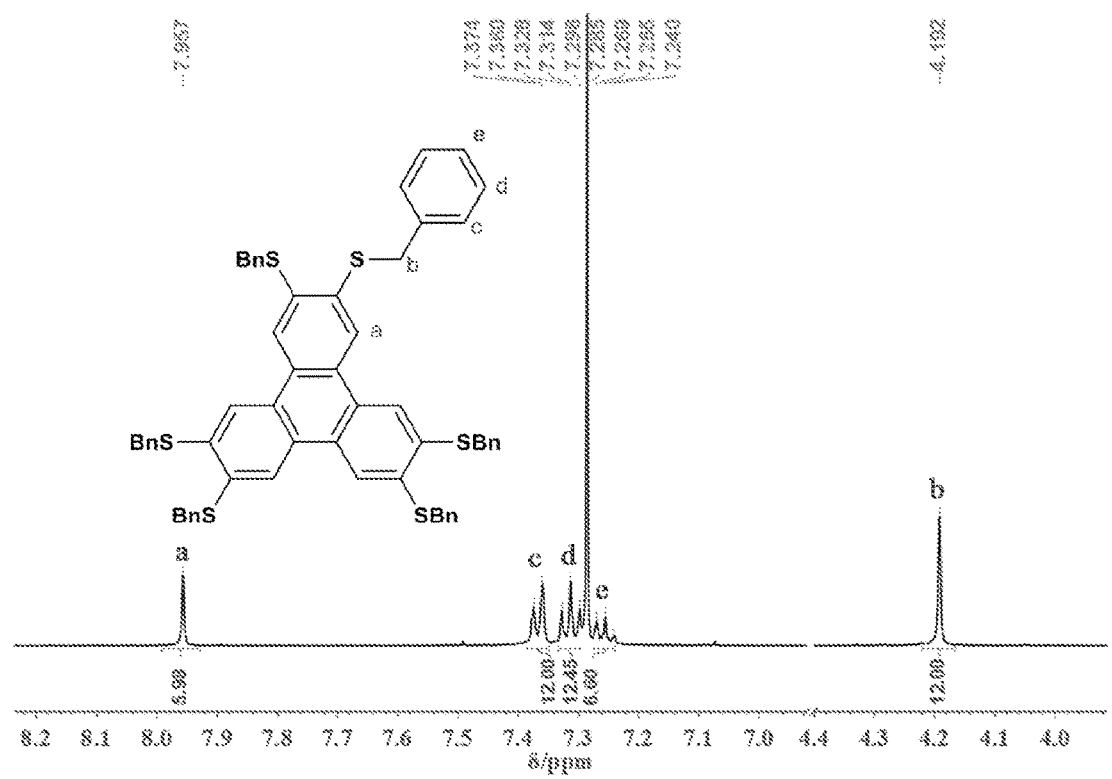
FIG. 34 shows $^1H$ NMR of 2,3,6,7,10,11-hexabenzylmercaptyltriphenylene.

FIG. 34 depicts $^1$H NMR of 2,3,6,7,10,11-hexabenzylmercaptyltriphenylene.

Example 1.5

Synthesis of Sodium Triphenylenehexathiolate (4)

To 50 mL of anhydrous liquid ammonia at −78° C., 2,3,6,7,10,11-hexabenzylmercaptyltriphenylene (3, 1.05 g, 1.90 mmol) was added under nitrogen atmosphere. Then, solid sodium (1.90 g, 83 mmol) was added in 10 portions (sodium stored in oil was rinsed by hexane and cut before use). A blue-green color appeared as the sodium dissolved. The solution was stirred for 4 hours at −78° C. Methanol (10 mL, degassed by bubbling nitrogen) was then added cautiously via a syringe to the flask until the blue color disappeared. The flask was warmed to room temperature over 2 hours. Subsequently, 100 mL of deionized water (degassed by bubbling nitrogen) was added and the aqueous layer was extracted with diethyl ether (3×100 mL). The aqueous layer was evaporated to about 50 mL (yellow color clear solution which was used in the following step immediately).

Example 1.6

Synthesis of 2,3,6,7,10,11-Hexathiotriphenylene (HTTP, 5)

The yellow solution (50 mL, from the previous step) was degassed by bubbling $N_2$ for 20 min. 10 mL of HCl (5%, degassed by $N_2$) was then added dropwise until yellow precipitate formed. The mixture was centrifuged at 8000 rpm/min for 10 min and the liquid was then decanted. The yellow solid was then washed by water (degassed with nitrogen, 3×100 mL) and acetone (degassed by nitrogen, 3×100 mL). The yellow precipitate was then dried under vacuum for 24 hours. 577 mg (1.37 mmol) of yellow product was collected in: 72% yield. The product was stored under vacuum.

$^1$H NMR (DMSO-$d_6$, 600 MHz): $\delta_H$ 8.70 (s, 6H), 5.87 (br, 6H, SH) ppm.

MALDI-TOF MS: found 419.2, calculated: 419.02.

IR: 2520 cm$^{-1}$ for S—H stretching.

Elemental analysis calculated for HTTP: C, 51.40; H, 2.88; S, 45.46. Found: C, 51.37; H, 2.90; S, 45.46.

Figure 35:
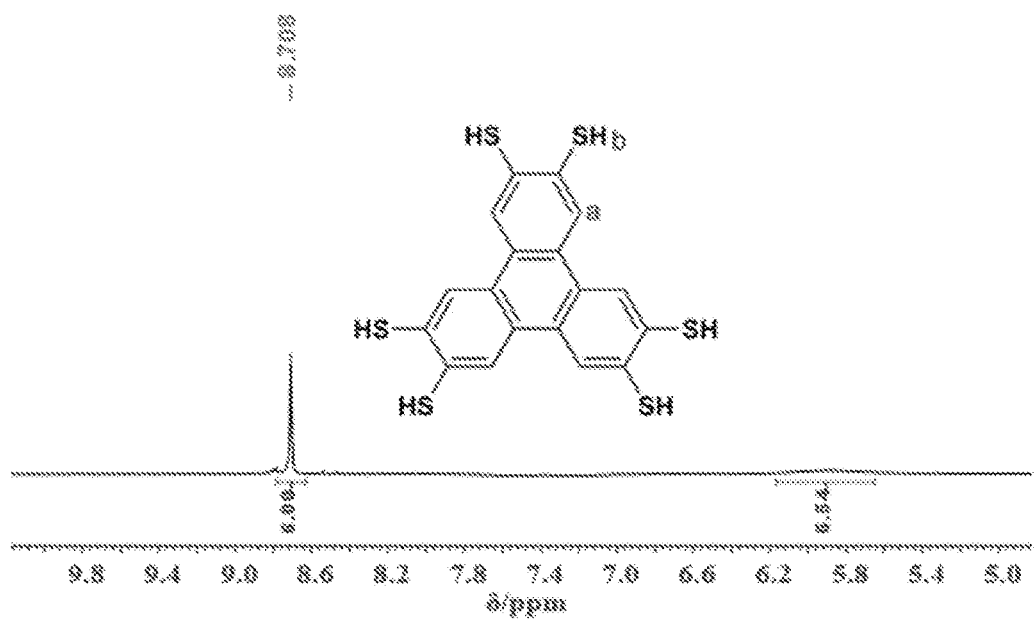
FIG. 35 shows $^1H$ NMR of 2,3,6,7,10,11-hexathiotriphenylene.

FIG. 35 depicts $^1$H NMR of 2,3,6,7,10,11-hexathiotriphenylene.

Example 1.7

Synthesis of $M_3HTTP_2$ Porous Coordination Polymers

Synthesis of $Co_3HTTP_2$: A solution of cobalt(II) acetate tetrahydrate (239 mg, 0.96 mmol) in 15 mL of degassed deionized water (degassed with $N_2$) was added to a solution of HTTP (200 mg, 0.48 mmol) in 15 mL of water (degassed by nitrogen and adjusted to pH 10 by 300 μL of 28% ammonium hydroxide). The mixture was stirred at 65° C. for 24 hours under $N_2$. After the reaction was cooled to room temperature, the black precipitate was filtered and washed with water (3×100 mL) and acetone (3×100 mL). It was then dried in vacuo at 40° C. for 24 hours. 166 mg of product was collected and stored under vacuum. Yield: 62%.

Synthesis of $Ni_3HTTP_2$: A solution of nickel(II) acetate tetrahydrate (239 mg, 0.96 mmol) in 15 mL of degassed deionized water (degassed with $N_2$) was added to a solution of HTTP (200 mg, 0.48 mmol) in 15 mL of water (degassed by nitrogen and adjusted to pH 10 by 300 μL of 28% ammonium hydroxide). The mixture was stirred at 65° C. for 24 hours under $N_2$. After the reaction was cooled to room temperature, the black precipitate was filtered and washed with water (3×100 mL) and acetone (3×100 mL). The product was stored under vacuum. 175 mg of product was collected and stored under vacuum. Yield: 66%.

Synthesis of $Cu_3HTTP_2$: A solution of copper(II) trifluoroacetylacetonate (355 mg, 0.96 mmol) in 15 mL of degassed deionized water (degassed with $N_2$) was added to a solution of HTTP (200 mg g, 0.48 mmol) in 15 mL of water (degassed by nitrogen and adjusted to pH 10 by 300 μL of 28% ammonium hydroxide). The mixture was stirred at 65° C. for 24 hours under $N_2$. After the reaction was cooled to room temperature, the black precipitate was filtered and washed with water (3×100 mL) and acetone (3×100 mL). 195 mg of product was collected and stored under vacuum. Yield: 72%.

Example 1.8

Synthesis of $M_3HHTP_2$ MOFs

The synthesis of metal-organic frameworks using organic linker 2,3,6,7,10,11-hexahydroxytriphenylene was adapted from Yaghi et al. (Chem. Mater. 2012, 24, 3511).

Synthesis of $Co_3HHTP_2$: To a 100 mL round bottom flask HHTP (200 mg, 0.617 mmol) and cobalt(II) acetate tetrahydrate (456 mg, 1.831 mmol) was added. 28 mL of deionized water was added to the round bottom flask. The solution was sonicated for 10 minutes. The reaction mixture was placed in a hot oil bath at 85° C. and stirred for 24 hours. The flask was allowed to cool for 2 hours and the product was filtered with a ceramic funnel and filter paper. The product was then washed with deionized water (3×50 mL) and acetone (3×50 mL). The solid product on the filter paper was then transferred to a vial and dried overnight under vacuum (20 mTorr) at 85° C. Mass of product: 341 mg.

Synthesis of $Ni_3HHTP_2$: To a 100 mL round bottom flask HHTP (200 mg, 0.617 mmol) and nickel(II) acetate tetrahydrate (456 mg, 1.831 mmol) was added. 28 mL of deionized water was added to the round bottom flask. The solution was sonicated for 10 minutes. The reaction mixture was placed in a hot oil bath at 85° C. and stirred for 24 hours. The flask was allowed to cool for 2 hours then the product was filtered with a ceramic funnel and filter paper. The product was washed with deionized water (3×50 mL) and acetone (3×50 mL). The solid product on the filter paper was then transferred to a vial and dried overnight under vacuum (20 mTorr) at 85° C. Mass of product: 338 mg.

Synthesis of $Cu_3HHTP_2$: To a 100 mL round bottom flask HHTP (200 mg, 0.617 mmol) and copper(II) trifluoroacetylacetonate (875 mg, 1.831 mmol) was added. 28 mL of deionized water was added to the round bottom flask. The solution was sonicated for 10 minutes. The reaction mixture was placed in a hot oil bath at 85° C. and stirred for 24 hours. The flask was allowed to cool for 2 hours then the product was then filtered with a ceramic funnel and filter paper. The product was washed with deionized water (3×50 mL) and with acetone (3×50 mL). The solid product on the filter paper was then transferred to a vial and dried overnight under vacuum (20 mTorr) at 85° C. Mass of product: 324 mg Example 1.9

Characterization of $M_3HTTP_2$ Porous Coordination Polymers

The simulated slipped parallel and staggered are two different packing modes that describe how the adjacent two layers of the porous coordination polymer stack together. In the slipped parallel packing, the atoms of each layer are displaced in the a and/or b directions from those of the adjacent layers but are aligned with the second-nearest-neighbor layers. In the staggered packing, the connections joints in one layer locate to the centers of a hexagonal lattice in the other layer but are aligned with the second-nearest-neighbor layers.

Example 1.10

Characterization of $M_3HHTP_2$ MOFs

Figure 36A:
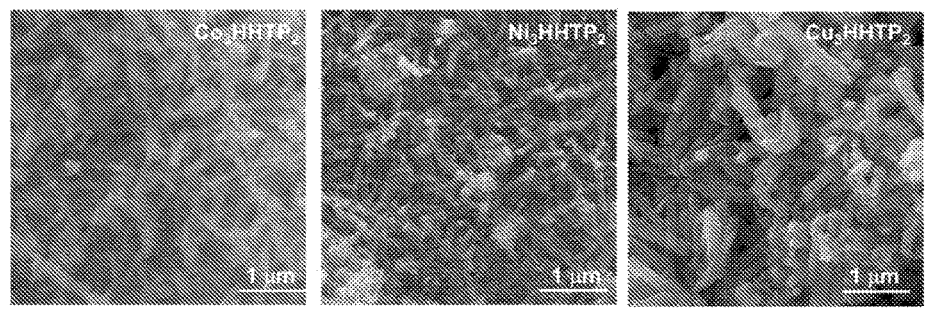
FIG. 36A shows scanning electron micrographs showing nanoscale morphology of MOFs.
Figure 36B:
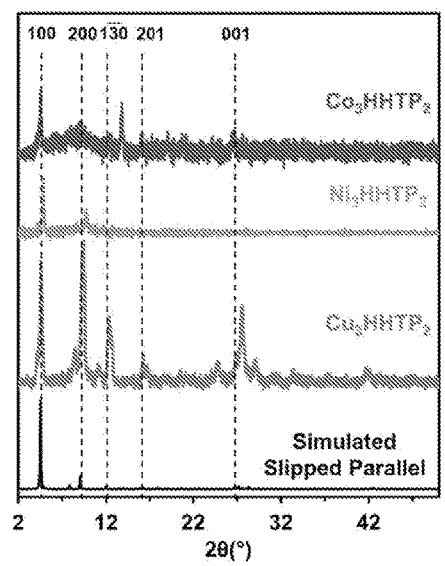
FIG. 36B shows experimental (colored) and simulated 'AAAA' stacking structure without the presence of interpolated layer (black) powder X-Ray Diffraction patterns.
Figure 36C:
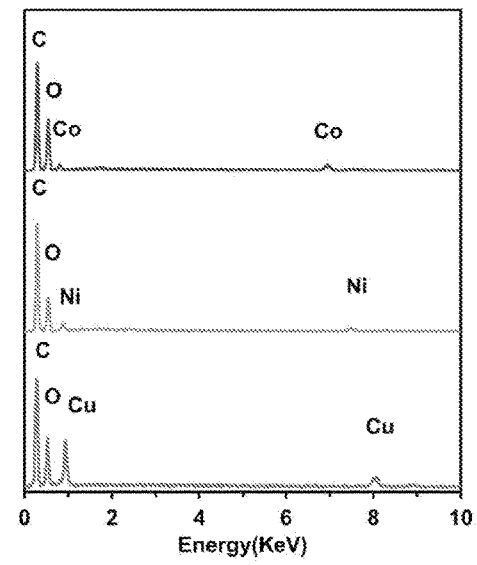
FIG. 36C shows Energy-Dispersive X-Ray Spectroscopy of $M_3HHTP_2$ MOFs showing the elemental composition of solid-state materials.

Example characterization of $M_3HHTP_2$ MOFs is illustrated in FIG. 36.

Example 1.11

Brunauer-Emmett-Teller (BET) Analysis

Prior to the porosity analysis, all samples were degassed under vacuum at 120° C. for 24 h. For Brunauer-Emmett-Teller (BET) calculations, a fitting range of 0 to 0.3 $P/P_o$ was used.

Example 1.12

X-ray Photoelectron Spectroscopy (XPS) of $M_3HTTP_2$ Porous Coordination Polymers The XPS spectra revealed the presence of S and N along with the respective metals (Co, Cu and Ni) used in the preparation of each $M_3HTTP_2$ PCP. High-resolution scans of the N 1s region in all $M_3HTTP_2$ PCPs suggest the presence of two distinct chemical environments with the peak found at ~401 eV corresponding to $NH_4^+$ anion that balances the overall negative charge of the framework and a band at ~400 eV which may indicate the presence of either coordinated or adsorbed neutral ammonia to the PCPs.

Applicants observed two sets of peaks in the Co 2p3 region, with binding energies of ~780 and ~795 eV, which describe the 2p3/2 and 2p1/2 levels in the theoretically expected 2:1 ratio. Further deconvolution of these signals gave rise to four distinct bands: the peaks at 779.2 and 796.1 eV were ascribed to $Co^{III}$, while the peaks found at 785.7 and 802.2 eV were assigned to $Co^{II}$ (FIG. 3). These results indicate mixed valency within the $Co_3HTTP_2$ PCPs and are in good agreement with the theoretical and experimental studies on the cobalt bis(dithiolene) complexes. Deconvoluted high-resolution spectrum of $Cu_3HTTP_2$ PCPs revealed the presence of two peaks at 932.6 and 934.9 eV, which can be assigned to $Cu^I$ and $Cu^{II}$ centers, respectively, and are strongly indicative of mixed valency within the framework (FIG. 5). The peak located at 951.3 eV results from the spin-orbit coupling and is ascribed to Cu 2p1/2. The high-resolution scan of the Ni 2p photoemission regions revealed the presence of two peaks with binding energies of ~852 and ~870 eV, which are attributed to the 2p3/2 and 2p1/2 levels, respectively (FIG. 4). These results are consistent with the experimental data reported in previous literature and thus demonstrate that only one type of Ni is present within the $Ni_3HTTP_2$ framework. Even though, the obtained XPS data for all $M_3HTTP_2$ PCPs may suggest the co-deposition of elemental metals and their respective oxides (e.g., Cu, CuO, NiO or CoO), the lack of observable features for the metal/oxides species on the pXRD spectrum (FIGS. 6A-6F) is in support of the occurrence of mixed valency within $M_3HTTP_2$ PCPs.

Moreover, Applicants observed the presence of three distinct peaks at ~163.0, ~166.0, ~168.0 eV, with varying intensities, on the XPS spectrum of S 2p region collected for all $M_3HTTP_2$ PCPs (FIG. 3-FIG. 5). Peak deconvolution of S 2p region generated four sets of doublets (doublets with an intensity ratio of 1:2 result from the spin-orbit coupling, and are strongly characteristic of the S 2p3/2 and 2p1/2 orbitals). The high intensity doublets found at ~163.6 and ~164.9 eV were assigned to M-S units within the $M_3HTTP_2$ frameworks while the XPS peaks located at binding energies >165.0 eV were attributed to the S—$O_3$ and S—$O_4$ oxidation states of sulfur. The low intensity doublets located at <163.0 eV are indicative of partially uncoordinated S—H thiols in the framework. Based on these observations, Applicants have estimated that defect density within all $M_3HTTP_2$ frameworks could be estimated as 40±5 atom % for all $M_3HTTP_2$ PCPs. Nonetheless, the XPS, EDS, IR and elemental analysis taken together are strongly indicative of efficient complexation of metallic nodes with bis(dithiolene) based ligands to form highly porous, conductive two-dimensional porous coordination polymers.

Example 1.13

Elemental Analysis

Elemental analysis revealed the presence of nitrogen within the bulk of $M_3HTTP_2$ PCPs accompanied by increased hydrogen content for the $M_3HTTP_2$ molecular formula (Table 1-Table 3). Together, these results suggest the ionic form of the synthesized $M_3HTTP_2$ porous coordination polymer, where $NH_4^+$ counter-ions associated with each $[M_3HTTP_2]^-$ subunit to balance for the overall negative charge of the complex. These observations are consistent with the experimental data from XPS analysis (FIG. 3-FIG. 5), as well as the work carried out by Marinescu and coworkers (2015).

The observed discrepancies in the calculated and determined elemental content (Table 1-Table 3) could be due to: i) the counter ions associated with each porous coordination polymer (e.g. $NH_4^+$ and $Na^+$); ii) coordinated water molecules; iii) presence of organic solvents coordinated to the framework/metal centers; iv) impurities in the form of metal oxides or elemental metals formed during the synthetic conditions; and v) organic and inorganic impurities from the precursors used for porous coordination polymers synthesis, thus creating a dilution effect in elemental analysis of $M_3HTTP_2$ materials.

Table 1, shown below, illustrates elemental and ICP-MS analysis of $Co_3HTTP_2$ coordination networks. Predicted elemental % calculated for porous coordination polymers based on the $M_3HTTP_2$ or $M_3HTTP_2 \cdot 6H_2O$ molecular formula.

TABLE 1

| Element | $Co_3HTTP_2$ (calculated) % | $Co_3HTTP_2 \cdot 6H_2O$ (calculated) % | Found (%) |
|---|---|---|---|
| Co | 17.57 | 15.87 | 12.21 |
| C | 42.98 | 38.81 | 34.57 |
| H | 1.20 | 2.17 | 2.86 |
| S | 38.25 | 34.53 | 23.07 |
| O | — | 8.62 | — |
| N | — | — | 2.08 |

Table 2, shown below, illustrates elemental and ICP-MS analysis of $Ni_3HTTP_2$ coordination networks. Predicted elemental % calculated for porous coordination polymers based on the $M_3HTTP_2$ or $M_3HTTP_2 \cdot 6H_2O$ molecular formula.

TABLE 2

| Element | Ni$_3$HTTP$_2$ (calculated) % | Ni$_3$HTTP$_2$•6H$_2$O (calculated) % | Found (%) |
|---|---|---|---|
| Ni | 17.51 | 15.81 | 15.66 |
| C | 43.01 | 38.84 | 33.76 |
| H | 1.20 | 2.17 | 2.97 |
| S | 38.27 | 34.55 | 26.52 |
| O | — | 8.62 | — |
| N | — | — | 1.69 |

Table 3, shown below, illustrates elemental and ICP-MS analysis of Cu$_3$HTTP$_2$ coordination networks. Predicted elemental % calculated for porous coordination polymers based on the M$_3$HTTP$_2$ or M$_3$HTTP$_2$.6H$_2$O molecular formula.

TABLE 3

| Element | Cu$_3$HTTP$_2$ (calculated) % | Cu$_3$HTTP$_2$•6H$_2$O (calculated) % | Found (%) |
|---|---|---|---|
| Cu | 18.69 | 16.90 | 20.30 |
| C | 42.39 | 38.34 | 35.09 |
| H | 1.19 | 2.14 | 2.53 |
| S | 37.73 | 34.11 | 26.46 |
| O | — | 8.51 | — |
| N | — | — | 2.19 |

Example 1.14

Electron Paramagnetic Resonance (EPR) Spectroscopy

For all EPR experiments, ~2 mg of each M$_3$HTTP$_2$ PCPs was transferred to an EPR tube set in liquid nitrogen.

Example 1.15

Attenuated Total Reflectance Infrared Spectroscopy of M$_3$HTTP$_2$ Porous Coordination Polymers Infrared spectra were recorded with an attenuated total reflectance (ATR) unit equipped with Zn—Se crystal (under air) by placing the pure powder of each M$_3$HTTP$_2$ PCP directly on the top of a crystal. The pressure arm was then lowered down and locked in position to ensure good contact between the sample and a crystal. ATR-IR (FIG. 10) featured a distinctive signal at ~2530 cm$^{-1}$ that can be attributed to the S—H stretching vibration. However, the same peak disappeared completely in the final product of the M$_3$HTTP$_2$ PCPs. This observation indicates that no detectable unreacted ligand is present within the PCPs.

Example 1.16

Thermal Gravimetric Analysis (TGA)

Thermal gravimetric analysis was performed using a TA Instruments TGA Q150 with a 20° C./min ramp from room temperature to 900° C.

Example 1.17

Deposition of Metal Organic Frameworks (MOFs) onto Electrodes 1 mg of either M$_3$HTTP$_2$ porous coordination polymer or M$_3$HHTP$_2$ MOF was suspended in 500 µL of deionized water or acetonitrile (degassed with nitrogen) and sonicated for 1 hour. 10 µL of the resulting suspension was transferred onto the working electrode and dried under nitrogen stream. 10 µL of Nafion solution (D-521 dispersion 5% w/w in water and 1-propanol from Alfa Aesar) was then added to cover the material which was dried under nitrogen before the use for all CVs in aqueous solutions. For those CVs done in organic solutions, no Nafion was applied.

Example 1.18

Cyclic Voltammetry in Aqueous Solution

The cyclic voltammetry study was carried out using a three-electrode system including a 3 mm glassy carbon working electrode, a reference electrode: Ag/AgCl (in saturated KCl solution) electrode, and a platinum wire counter electrode. The supporting electrolyte was 0.1 M KCl. Nanopure water (18.2 MΩ) was used to make all solutions. Before all experiments, the solutions were degassed by bubbling nitrogen gas for 30 min.

Example 1.19

Cyclic Voltammetry in Organic Solution

The cyclic voltammetry was carried out using a three-electrode system including a 3 mm glassy carbon working electrode, a reference electrode: Ag/Ag$^+$ (0.01 M) electrode, and a platinum wire counter electrode. The supporting electrolyte was 0.1 M tetrabutylammonium hexaflurophosphate (TBAPF$_6$) in acetonitrile. TBAPF$_6$ was recrystallized from ethanol twice and dried before use. Before all experiments, the solutions were degassed by bubbling nitrogen gas for 30 min.

Example 1.20

Linear Sweep Voltammetry Methods

Linear sweep voltammetry study was performed using a three-electrode system including a 3 mm glassy carbon working electrode, a reference electrode: Ag/Ag$^+$ (0.01 M) electrode, and a platinum wire counter electrode. The supporting electrolyte was 0.1 M tetrabutylammonium hexaflurophosphate (TBAPF$_6$) in acetonitrile. TBAPF$_6$ was recrystallized from ethanol twice and dried before use. The sweep range was −2.0 V to +2.0 V. The MOF material on the electrode was pre-oxidized/reduced at the optimized potential varying from −0.2 V to −1.8 V (see Example 1.26 below, illustrating optimization of pre-oxidation voltage in LSV) for the optimized time period ranging from 0 to 360 sec (see Example 1.25 below, illustrating optimization of pre-oxidation time in LSV) while gas (ethylene or nitrogen) was bubbled at 10 mL/min into the solution for 15 min to maintain a gas saturated solution.

Example 1.21

Cyclic Voltammetry of HHTP and HTTP Ligands

Example cyclic voltammetry of HHTP and HTTP ligands is illustrated in FIG. 13.

Example 1.22

Cyclic Voltammetry of $M_3HHTP_2$ in Organic Solutions

Example cyclic voltammetry of $M_3HHTP_2$ in organic solutions is illustrated in FIG. 12.

Example 1.23

Cyclic Voltammetry of $M_3HHTP_2$ and $M_3HTTP_2$ in Aqueous Solutions

Ortho-quinone compounds are known to undergo reversible redox conversion between catechol, semiquinone and quinone forms. The cyclic voltammogram of the HHTP ligand, performed in MeCN, revealed that hexahydroxytriphenylene redox activity is similar to what has been previously reported (FIG. 13). There were three anodic peaks corresponding to the transition from CatCatCat to CatCatSq to CatSqSq to SqSqSq. These anodic peaks were observed within the +1.0 V and +1.6 V range. One big cathodic peak which is about three times the size of each anodic peak was observed at +0.97 V indicating that the oxidation of HHTP takes place in 3 steps while the reduction of HHTP occurs in only one step. Other low intensity peaks are probably associated with the byproducts from the reaction of water/supporting electrolyte and electrochemical intermediates. To the best of Applicants' knowledge, this is the first report concerning electrochemical characterization of HTTP ligand. The cyclic voltammogram of HTTP revealed the presence of 2 anodic peaks and 3 cathodic peaks. The anodic peak at +1.37 V is twice as large as the anodic peak at +0.81 V indicating that the second and third oxidation of HTTP occur at similar potentials. Correspondingly, the first and second reduction peak (+1.11 V and +0.70 V) are close to each other but the third reduction peak (−0.63 V) is distinct. Comparing to HHTP, HTTP is oxidized easier and the reduction from SqSqSq form to CatSqSq form is also easier. It is probably due to the more electronegative characteristic of oxygen in comparison to sulfur.

The absence of reversible redox peaks in the CV of $M_3HTTP_2$ and $M_3HHTP_2$ materials may indicate that the electron transfer is irreversible or it is followed by the chemical reactions giving rise to new non-active redox species. Even though, Applicants cannot exclude specific background electrolyte-coordination network interactions, Applicants hypothesize that the kinetics of the electron transfer may be relatively slow in comparison to the selected scan rate, thus masking the presence of reductive redox waves. Since these prepared coordination polymers exhibit a large degree of porosity (BET data—FIG. 7), Applicants anticipate that the observed electron transfer kinetics may be directly related to the morphology of $M_3HTTP_2$ and $M_3HHTP_2$ materials rather than intrinsic electrochemical kinetics of the studied coordination polymers. For instance, shifts in peak potential and intensity may be associated with ohmic drops within the thick layer of the PCPs (distributed resistance) as shown in previous literature. Together, these factors introduce large complexity in the interpretation of redox process occurring during the voltammetric measurements.

Example 1.24

Figure 37:
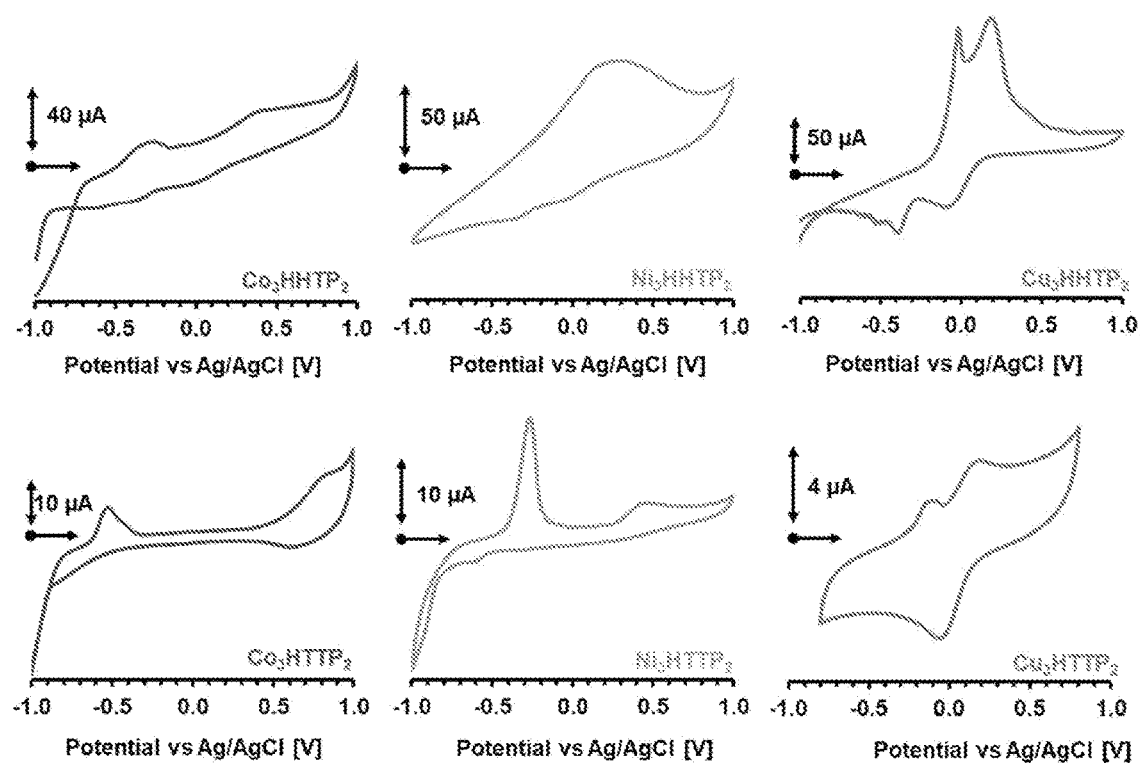
FIG. 37 shows CVs of $M_3HTTP_2$ MOF in aqueous solution. Nafion was used for attaching MOF to working electrode. Scan rate: 50 mV/s, 0.1 mM $TBAPF_6$ in $CH_3CN$. 3 mm glassy carbon working electrode, platinum wire and Ag/AgCl electrodes were used as the working, counter and reference electrodes, respectively. Arrows indicate scan direction.

Solvent Effect on the Voltammetric Response of $M_3HHTP_2$ and $M_3HTTP_2$ Porous Coordination Polymer Applicants observed a dramatic solvent effect on the reduction and oxidation potentials of $M_3HTTP_2$ and $M_3HHTP_2$ porous coordination polymers in aqueous solutions vs. organic solvents (FIG. 12 and FIG. 37). In aqueous environment, the two oxidative waves observed above +0.70 V in MeCN are transformed into a single redox band in aqueous solution, indicating that both observed redox processes take place at nearly the same anodic potentials. These observations are consistent with literature findings on electrochemistry of quinone/catechol systems where quinones often undergo a one-step two-electron reduction in aqueous buffered solutions, while two-step one-electron reduction is observed in non-aqueous background electrolyte. Since both solvents have different dielectric constants (80.1 for $H_2O$ and 36.6 for MeCN), the observed changes in the voltammetric response may be directly related to the polarity of each solvent used for the measurements rather than caused by interactions between the solvent and coordinating polymer.

Example 1.25

Studies of Ethylene Capture by $Cu_3HTTP_2$ Using Cyclic Voltammetry

As shown in FIG. 15, the position of the first anodic wave (+0.21 V) in $Cu_3HTTP_2$ PCPs under inert atmosphere (Ar or $N_2$) shifted reversibly to more negative potential (+0.07 V) upon cycling with ethylene. Interestingly, in both the absence and presence of ethylene in MeCN, Applicants did not observe any changes in the position and intensity of recorded peaks (FIG. 16). In aqueous solution measurements, however, Applicants used Nafion (a sulfonated tetrafluoroethylene based fluoropolymer-copolymer) to improve mechanical stability of the drop-cast layer of $M_3HTTP_2$ coordination polymers. Therefore, the observed shift in the position of the anodic wave could be caused by: i) specific Nafion-ethylene interactions; or ii) that the Nafion-membrane creates a different ionic environment in the presence of ethylene, thus shifting the effective potential at the electrode surface to more negative values. Taken together, these results suggest that further voltammetric studies of $M_3HTTP_2$ and $M_3HHTP_2$ PCPs should be performed in non-aqueous medium (e.g., MeCN) due to: i) higher stability of the drop-cast $M_3HTTP_2$ and $M_3HHTP_2$ layers in organic solvents compared to aqueous solvents; and ii) minimization of changes to the local environment (at the electrode surface) induced by the presence of Nafion.

Example 1.26

Optimization of Pre-Oxidation Time in LSV

Example optimization of pre-oxidation time in LSV is illustrated in FIG. 17.

Example 1.27

Optimization of Pre-Oxidation Voltage in LSV

Example optimization of pre-oxidation voltage in LSV is illustrated in FIG. 18.

Example 1.28

Figure 38:
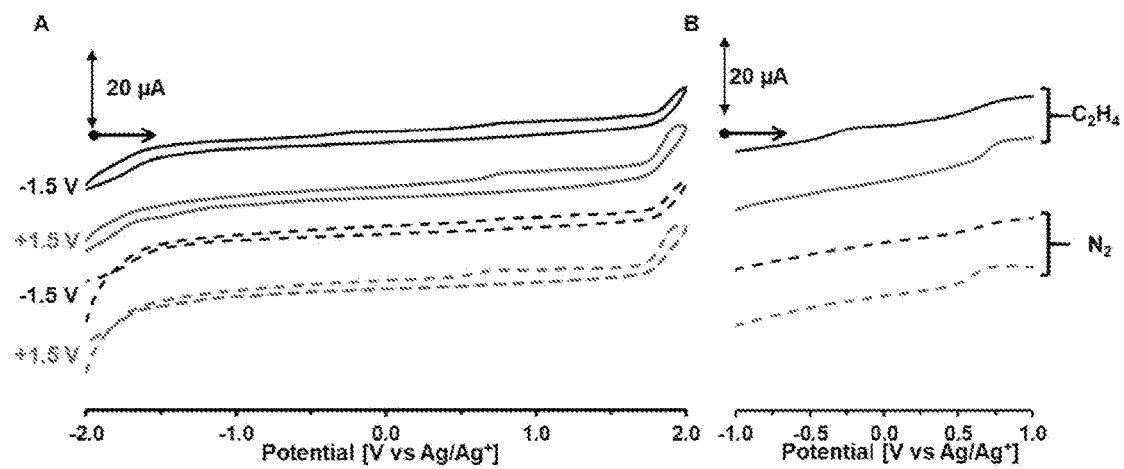
FIG. 38 shows cyclic voltammetry of $Ni_3HHTP_2$ in dichloromethane (DCM) solution. The MOF materials are pre-oxidized or pre-reduced at +1.5 V or −1.5 V for 120 sec as shown. Scan rate: 50 mV/s, 0.1 mM $TBAPF_6$ in DCM. 3 mm glassy carbon working electrode, platinum wire and $Ag/Ag^+$ electrodes were used as the working, counter and reference electrodes, respectively. Arrows indicate scan direction.

Cyclic Voltammetry of $Ni_3HTTP_2$ MOF with Ethylene and Nitrogen in Dichloromethane Example cyclic voltammetry of $Ni_3HTTP_2$ MOF with ethylene and nitrogen in dichloromethane is illustrated in FIG. 38.

Example 1.29

Diffusion Controlled Process Determined by Scan Rate Effect in LSV

Example diffusion controlled process determined by scan rate effect in LSV is illustrated in FIG. 19.

Example 1.30

LSV of $M_3HHTP_2$ MOFs with Ethylene and Nitrogen

Example LSV of $M_3HHTP_2$ MOFs with ethylene and nitrogen is illustrated in FIG. 20.

Example 1.31

LSV of $M_3HTTP_2$ Porous Coordination Polymers in Ethylene and Nitrogen—Discussion As observed in FIG. 11, the LSV responses of oxidized form of $M_3HTTP_2$ in $N_2$ and ethylene were indistinguishable. In principle, the intensity of the first anodic wave in $N_2$ should be comparable to the reduced form of the $M_3HTTP_2$ PCPs in ethylene, as in both instances the unbound form (ethylene free) of the $M_3HTTP_2$ material is present. Applicants anticipate that some non-specific solvent-$M_3HTTP_2$ interactions may occur ($TBA^+$ and $PF_6^-$ associated counterions) that results in 'blocking' the active sites of the $M_3HTTP_2$ PCPs, thus giving similar peak intensity in $N_2$ as for the oxidized $M_3HTTP_2$-ethylene adduct. Due to high affinity of the coordination polymer to ethylene (during oxidation at +1.5 V), the charge compensation may occur through the $M_3HTTP_2$-ethylene adduct formation, subsequently resulting in the expulsion of the associated counterions from the pores of the PCPs. However, in both instances ($N_2$ and ethylene) similar number of active sites in $M_3HTTP_2$ would be occupied, thus producing comparable voltammetric peak intensities. Reduction of the material at −1.5 V may expel ethylene from the pores of the $M_3HTTP_2$, leading to the observations where the peak intensity represents the 'fully' unbound form of the coordination network. The diffusion of ethylene, accompanied by a counterflux of ions (bulky $TBA^+$) to the redox active sites in the pores of $M_3HTTP_2$, would thus compensate for the induced negative charge in the material. Taken together, these observations may indicate that the changes in redox peak intensity observed for the $M_3HTTP_2$ porous coordination polymers are driven by ethylene-porous framework interactions regardless of the metal center used in their synthesis

Example 1.32

Preparation of Solid-State Devices: Drop-Casted Thin Films

Figure 21A:
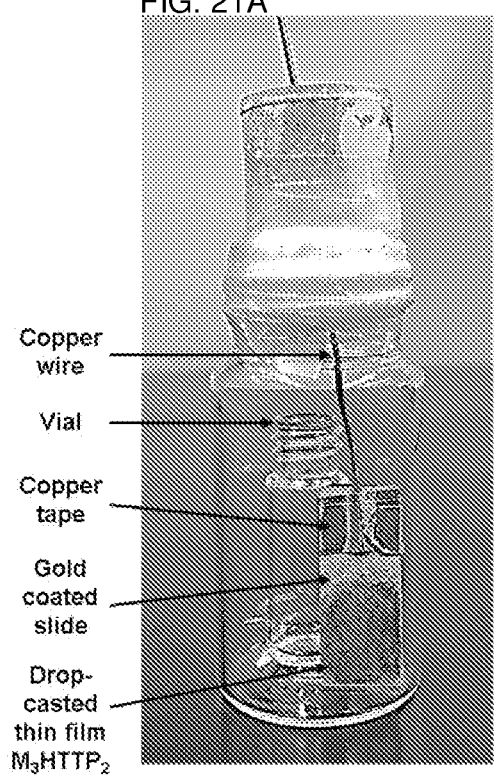
FIG. 21 shows experimental designs for solid-state electrochemical capture and release of ethylene by conductive glass slides coated with a thin film of $M_3HTTP_2$ (FIG. 21A), and a compressed pellet of $M_3HTTP_2$ (FIG. 21B).
Figure 21B:
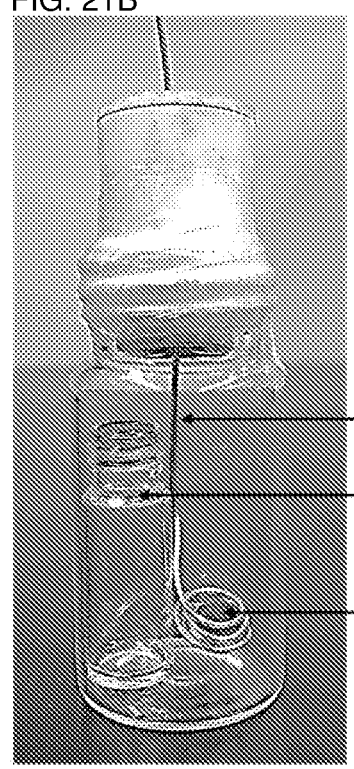

The $M_3HTTP_2$ coated slides for ethylene capture were prepared by evaporating a thin layer of chromium (10 nm) first, then gold (100 nm) sequentially using thermal evaporator (Covap, Angstrom Engineering, 1 Å/s evaporation rate) onto a frosted glass slide (2.5 cm×1.5 cm×0.1 cm, 4±1 µm surface roughness) and then drop-casting multiple aliquots of PCP solution (50 mg of $M_3HTTP_2$ sonicated in 10 mL of MeCN for 1 h) until 5 mg loading per each slide was obtained. Subsequently, a copper wire (9 cm and 0.64 mm in diameter, Fisher Scientific) was taped to the slide using a conductive copper tape, with an adhesive backing, (3 cm and 0.64 cm in diameter, Electron Microscopy Sciences) to establish an electrical contact with the potentiostat (FIG. 21A).

Example 1.33

Preparation of Solid-State Devices: Compressed Pellets

The compressed pellets were prepared by adding the powdered $M_3HTTP_2$ and $M_3HHTP_2$ analogs into a pellet die with a diameter of 6 mm (Across International, Livingston, N.J.) and by applying a constant pressure of 6.9 MPa for 5 min using a Desktop Pellet Press (Across International, Livingston, N.J.). Applicants then integrated compressed pellets of each $M_3HTTP_2$ porous coordination polymer (62 mg, 6 mm diameter and 1.45 mm thickness) into a solid-state device shown in FIG. 21B. Copper wire wrapped around the pellet (total length of the copper wire including the wrapped portion around the pellet, 30 cm and 0.64 mm in diameter, Fisher Scientific) established an electrical contact between the coordination network and the power supply.

Example 1.34

Solid-State Electrochemically-Driven Capture of Ethylene

In all solid-state ethylene capture measurements, the applied potentials ranging from −2.0 V to +2.0 V were delivered by a potentiostat to facilitate oxidation and reduction of the $M_3HTTP_2$ PCPs, respectively. Delivery of +2.0 V to the device in the presence of ethylene (balloon filled with ~600 mL of ethylene, placed above the vial) promoted electrochemically-driven gas capture. Subsequent exposure to vacuum for 120 min at $1.5 \times 10^{-3}$ Torr using a vacuum pump (Edwards), removed any unbound gas.

Example 1.35

Detection of Electrochemically-Driven Release

Figure 39:
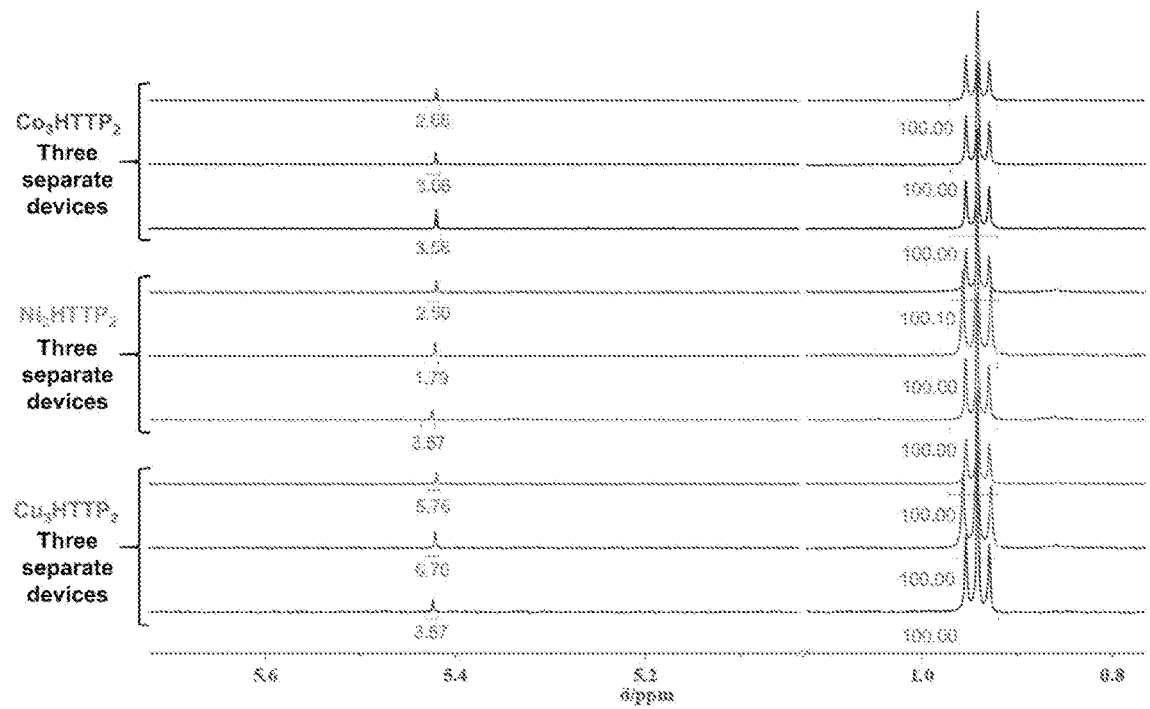
FIG. 39 shows $^1H$ NMR of DMSO-$d_6$ after solid-state ethylene capture by $Co_3HTTP_2$, $Ni_3HTTP_2$ and $Cu_3HTTP_2$ PCPs drop-casted onto the conductive substrate. Experimental conditions: 60 min oxidation at +2.0 V in the presence of ethylene, after the exposure to vacuum for 120 min and followed by the reduction for 60 min at −2.0 V to release the ethylene from the $M_3HTTP_2$ coated slides. All measurements were carried out using three separate devices made of $M_3HTTP_2$ PCPs.
Figure 40:
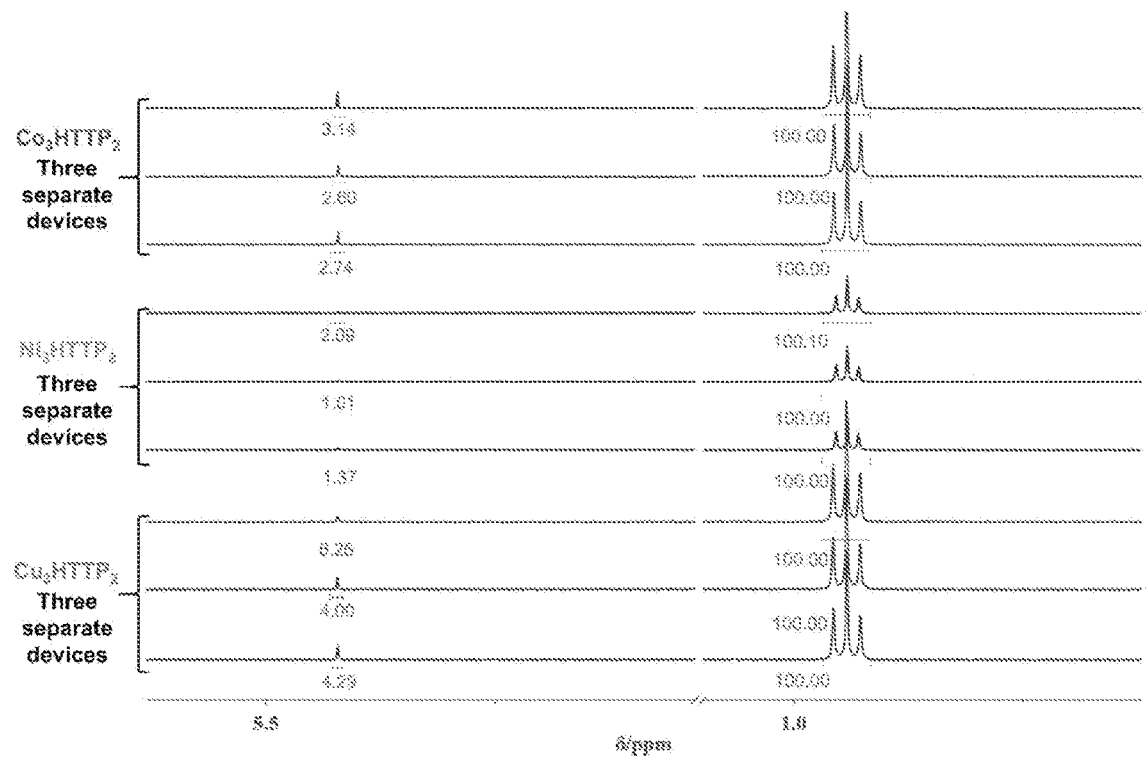
FIG. 40 shows $^1H$ NMR of DMSO-$d_6$ after solid-state ethylene capture by $Co_3HTTP_2$, $Ni_3HTTP_2$ and $Cu_3HTTP_2$ PCPs compressed pellets. Experimental conditions: 60 min oxidation at +2.0 V in the presence of ethylene, after the exposure to vacuum for 120 min and followed by the reduction for 60 min at −2.0 V to release the ethylene from the $M_3HTTP_2$ pellets. All measurements were carried out using three separate devices made of $M_3HTTP_2$ PCPs.

The vial was then refilled with house $N_2$ for 60 seconds and the NMR solvent (DMSO-$d_6$) with internal standard ($3.42 \times 10^{-4}$ M, total volume of 760 µL) was injected into a vial (1 mL). The internal standard was prepared by dissolving 10 mg of $TBAPF_6$ in 1 mL of DMSO-$d_6$. For the NMR measurements, 10 µL of internal standard was transferred into the NMR tube filled with 750 µL of DMSO-$d_6$ and the resulting solution was then vortexed for 15 seconds to ensure homogenization. Charging the compressed pellet at −2.0 V stimulated the release of ethylene. Partitioning of ethylene from the gas phase into the NMR solvent was quantified by NMR spectroscopy (FIG. 39 and FIG. 40). The timing of capture, release, and partitioning steps was unoptimized. The use of $TBAPF_6$ organic salt as internal standard enabled quantification of electrochemically captured/released ethylene. The concentration of ethylene in the headspace of the container was estimated using Henry's law for gas-liquid partitioning.

Example 1.36

Figure 41:
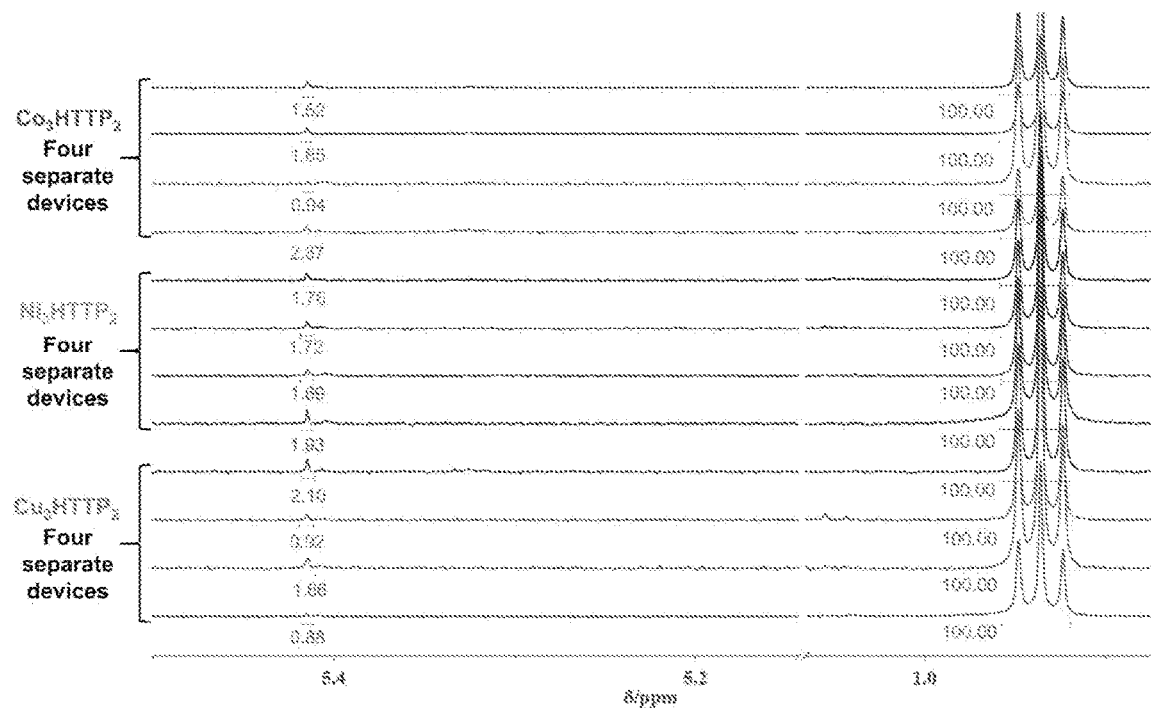
FIG. 41 shows $^1H$ NMR of DMSO-$d_6$ after solid-state ethylene capture by $Co_3HTTP_2$, $Ni_3HTTP_2$ and $Cu_3HTTP_2$ PCPs drop-casted onto the conductive substrate. Experimental conditions: 60 min oxidation at +2.0 V in the presence of ethylene and 2 ppt of CO and $H_2S$, after the exposure to vacuum for 120 min and followed by the reduction for 60 min at −2.0 V to release the ethylene from the $M_3HTTP_2$ coated slides. All measurements were carried out using four separate devices made of $M_3HTTP_2$ PCPs.
Figure 42:
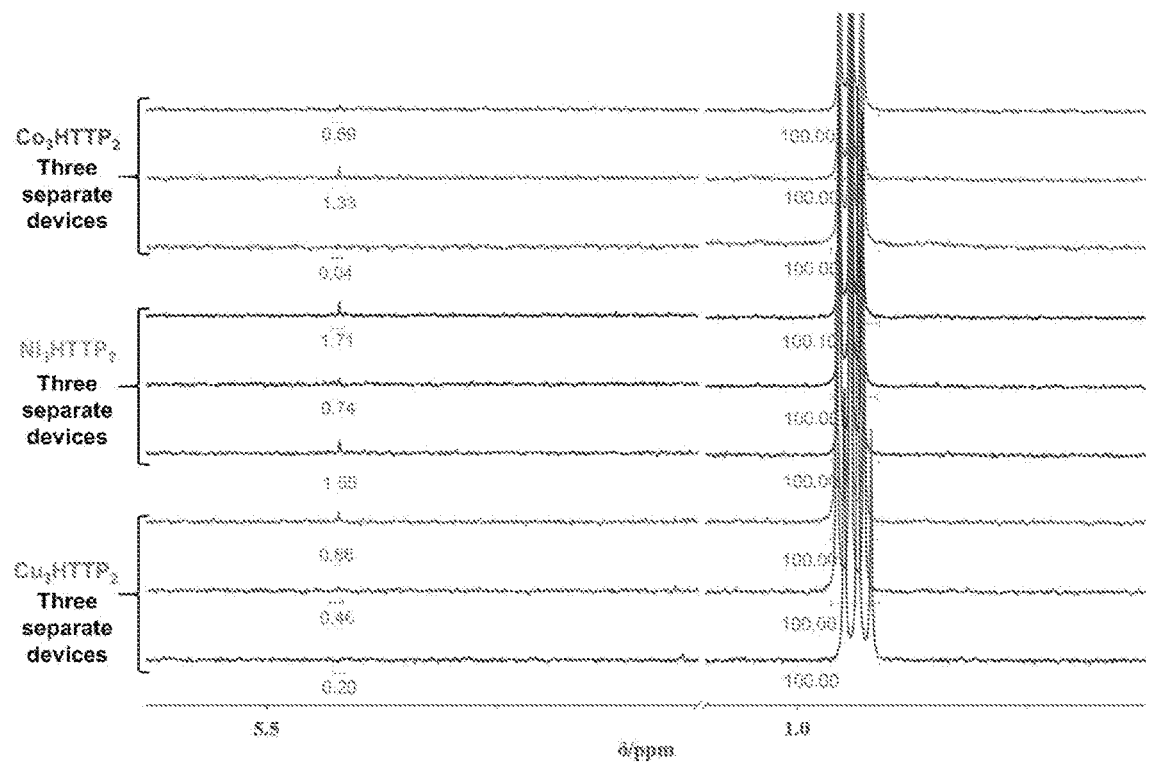
FIG. 42 shows $^1H$ NMR of DMSO-$d_6$ after solid-state ethylene capture by $Co_3HTTP_2$, $Ni_3HTTP_2$ and $Cu_3HTTP_2$ PCPs compressed pellets. Experimental conditions: 60 min oxidation at +2.0 V in the presence of ethylene and 2 ppt of CO and $H_2S$, after the exposure to vacuum for 120 min and followed by the reduction for 60 min at −2.0 V to release the ethylene from the $M_3HTTP_2$ coated slides. All measurements were carried out using three separate devices made of $M_3HTTP_2$ PCPs.

Solid-State Electrochemically-Driven Capture/Release of Ethylene in the Presence of Poisoning Interferents (CO and $H_2S$) at 2 ppt During the poisoning experiments, the drop-casted layer/compressed pellets of each $M_3HTTP_2$ PCP were exposed to the mixture of gases: ethylene, $H_2S$ and CO (one balloon filled with ~600 mL of ethylene, and two separate balloons containing ~600 mL of either $H_2S$ or CO at 10,000 ppm, placed above the vial) for 60 min while applying +2.0 V electrical potential. This step was followed by the subsequent exposure to vacuum for 120 min to remove any unbound gas. The vial was then refilled with house $N_2$ for 60 seconds and the NMR solvent (DMSO-$d_6$) with internal standard (3.42×10$^{-4}$ M, total volume of 760 μL) was injected into a vial (1 mL). The $M_3HTTP_2$ PCPs were further left for 60 min at -2.0 V to ensure partitioning of released $C_2H_4$ in DMSO-$d_6$. (FIG. 41 and FIG. 42).

Example 1.37

Figure 43:
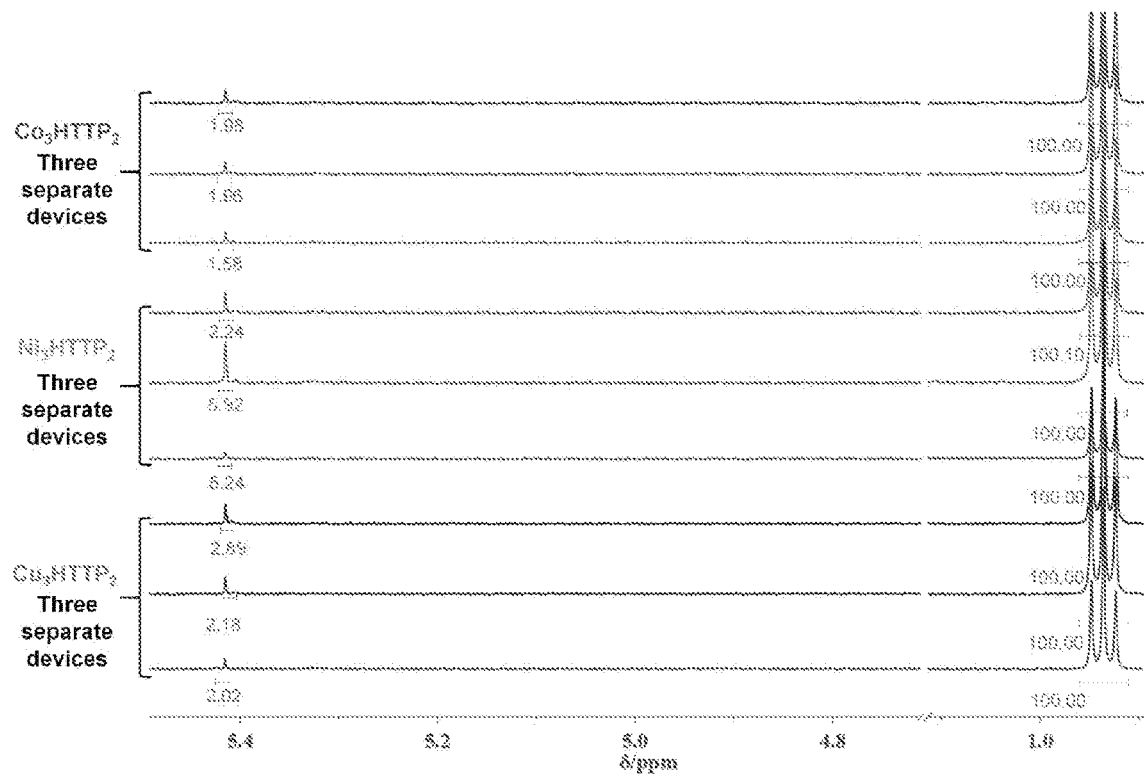
FIG. 43 shows $^1H$ NMR of DMSO-$d_6$ after solid-state ethylene capture by $Co_3HTTP_2$, $Ni_3HTTP_2$ and $Cu_3HTTP_2$ PCPs drop-casted films. Experimental conditions: 60 min oxidation at +2.0 V in the presence of ethylene and 80 ppm of CO and $H_2S$, after the exposure to vacuum for 120 min and followed by the reduction for 60 min at −2.0 V to release the ethylene from the $M_3HTTP_2$ coated slides. All measurements were carried out using three separate devices made of $M_3HTTP_2$ PCPs.

Solid-State Electrochemically-Driven Capture/Release of Ethylene in the Presence of Poisoning Interferents (CO and $H_2S$) at 80 ppm During the poisoning experiments, the drop-casted layer/compressed pellets of each $M_3HTTP_2$ PCP were exposed to the mixture of gases: ethylene, $H_2S$ and CO (one balloon filled with ~600 mL of ethylene, and two separate balloons containing ~600 mL of either $H_2S$ or CO diluted to 80 ppm with $N_2$, placed above the vial) for 60 min while applying +2.0 V electrical potential. This step was followed by the subsequent exposure to vacuum for 120 min to remove any unbound gas. The vial was then refilled with house $N_2$ for 60 seconds and the NMR solvent (DMSO-$d_6$) with internal standard (3.42×10$^{-4}$ M, total volume of 760 μL) was injected into a vial (1 mL). The $M_3HTTP_2$ PCPs were further left for 60 min at -2.0 V before the NMR spectra were collected (FIG. 43).

Example 1.38

Attempted Electrochemical Capture/Release with $M_3HHTP_2$ Controls

Like the HTTP-based porous coordination polymers, the $M_3HHTP_2$ analogs were oxidized at +2.0 V under ethylene for 60 min (balloon filled with ~600 mL of ethylene, placed above the vial) after which the compressed pellets/drop-casted films were placed under vacuum for 120 min to remove any retained ethylene from the pores of the material. The vial was then refilled with house $N_2$ for 60 seconds and the NMR solvent (DMSO-$d_6$) with internal standard (3.42×10$^{-4}$ M, total volume of 760 μL) was injected into a vial (1 mL). This step was followed by electrochemical release of ethylene for 60 min at -2.0 V. The detection of released ethylene was carried out using NMR spectroscopy (FIG. 30-FIG. 31).

Example 1.39

Figure 24:
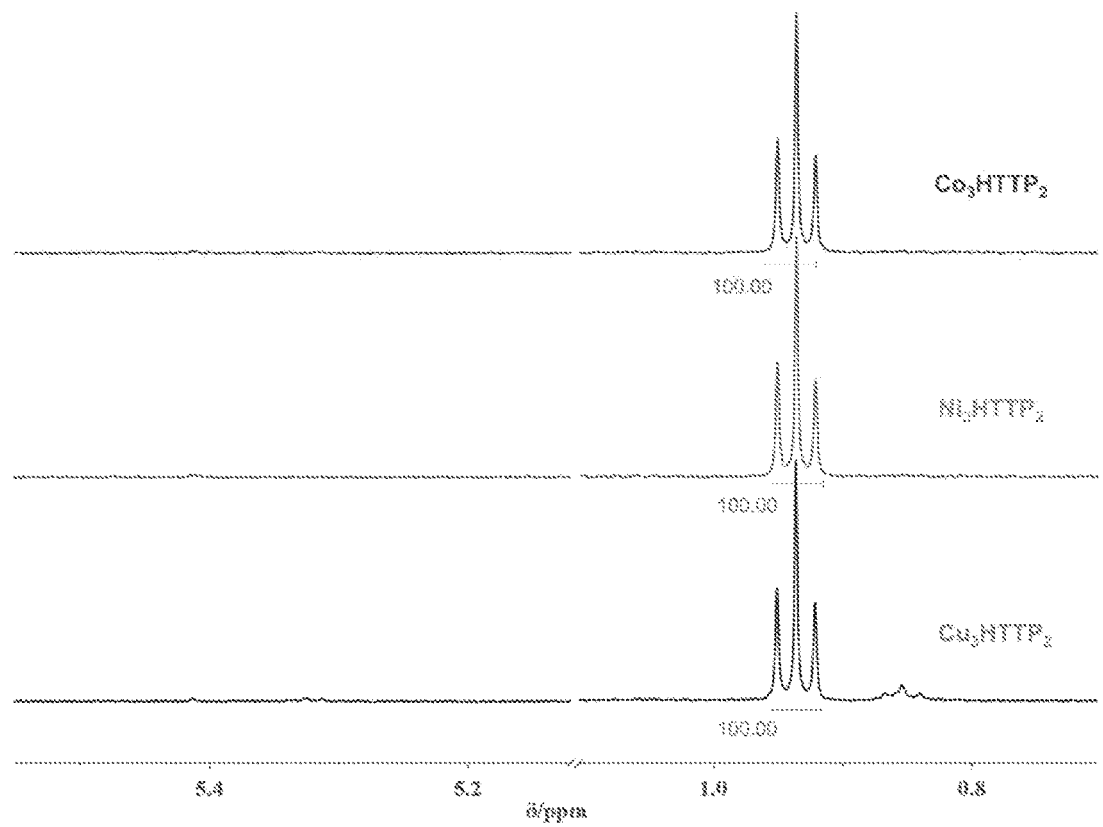
FIG. 24 shows $^1H$ NMR of DMSO-$d_6$ after solid-state ethylene capture by $Co_3HTTP_2$, $Ni_3HTTP_2$ and $Cu_3HTTP_2$ PCPs drop-casted layers. Experimental conditions: 60 min capture by oxidation at +2.0 V in the presence of ethylene, followed by the exposure to vacuum for 120 min to remove excess ethylene. During the release step, no electrical potential was applied to the samples prior to the NMR analysis.
Figure 27:
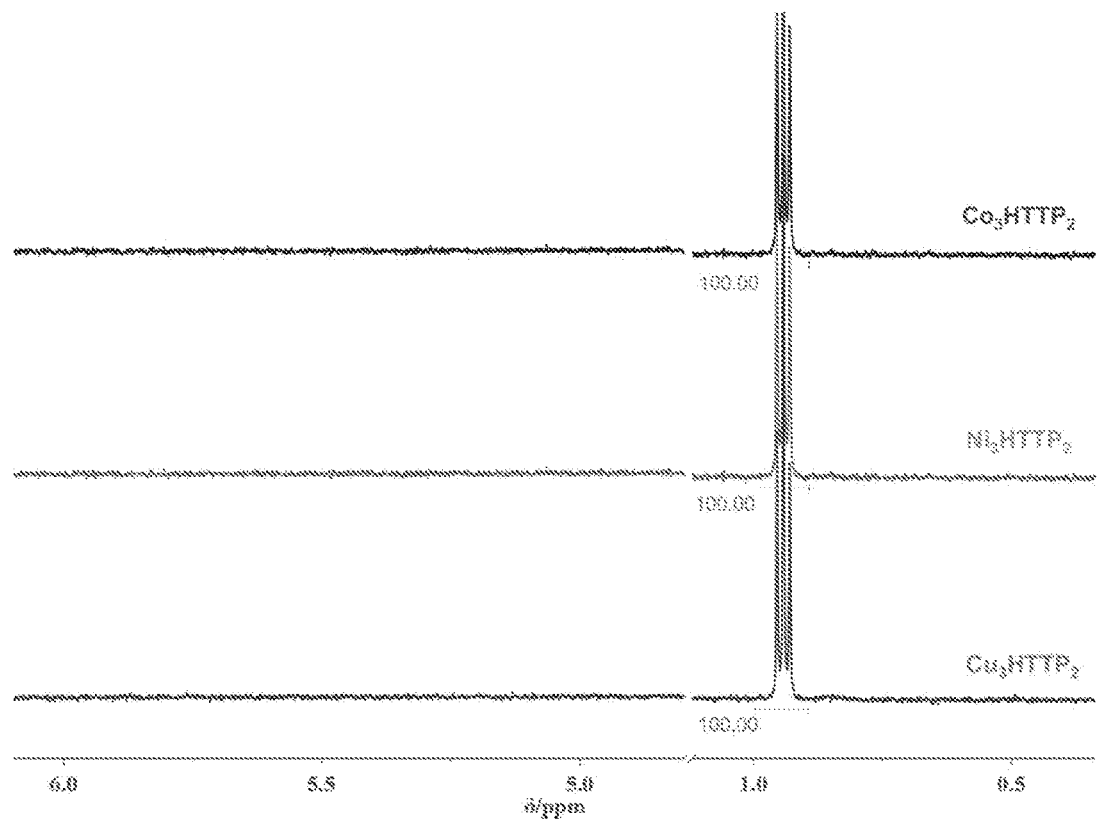
FIG. 27 shows $^1H$ NMR of DMSO-$d_6$ after solid-state ethylene capture by $Co_3HTTP_2$, $Ni_3HTTP_2$ and $Cu_3HTTP_2$ PCPs compressed pellets. Experimental conditions: 60 min oxidation at +2.0 V in the presence of ethylene followed by the exposure to vacuum for 120 min. During the reduction step, no electrical potential was applied to the samples prior to the NMR analysis.

Attempted Electrochemical Capture/Release with $M_3HTTP_2$ Controls Without the Reduction Step Applicants also carried out experiments in which the compressed pellets/drop-casted film were placed under ethylene for 60 min (balloon filled with ~600 mL of ethylene, placed above the vial) at +2.0 V and then they were subsequently exposed to vacuum for 120 min to evacuate unbound ethylene. The vial was then refilled with house $N_2$ for 60 seconds and the NMR solvent (DMSO-$d_6$) with internal standard (3.42×10$^{-4}$ M, total volume of 760 μL) was injected into a vial (1 mL). The $M_3HTTP_2$ PCPs were then left for 60 min without the application of negative potential before the NMR spectra were collected (FIG. 24 and FIG. 27).

Example 1.40

Figure 25:
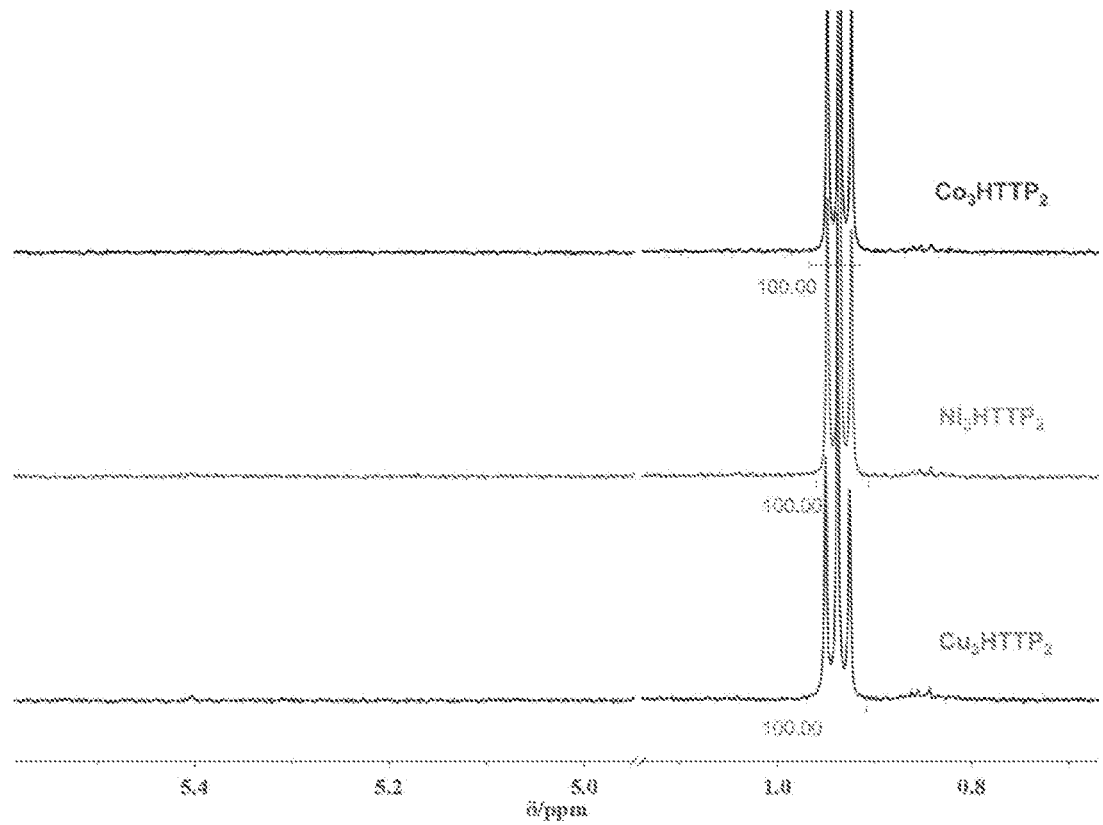
FIG. 25 shows $^1H$ NMR of DMSO-$d_6$ after solid-state ethylene capture by $Co_3HTTP_2$, $Ni_3HTTP_2$ and $Cu_3HTTP_2$ PCPs drop-casted layers. Experimental conditions: 60 min exposure to ethylene without the application of potential, followed by the exposure to vacuum for 120 min. Reduction step was performed for 60 min at −2.0 V to release the ethylene from the $M_3HTTP_2$ coated slides.

Attempted Electrochemical Capture/Release with $M_3HTTP_2$ Controls Without the Oxidation Step Applicants have also performed additional control experiment in which the oxidation step was omitted prior to the NMR analysis. This control experiment was achieved by exposing the compressed pellet or the drop-casted film of each $M_3HTTP_2$ PCP to ethylene for 60 min (balloon filled with ~600 mL of ethylene, placed above the vial) without the application of positive potential. Applicants have then placed the pellet/film under the vacuum for 120 min to remove any retained/adsorbed ethylene from the PCPs. The vial was then refilled with house $N_2$ for 60 seconds and the NMR solvent (DMSO-$d_6$) with internal standard (3.42×10$^{-4}$ M, total volume of 760 μL) was injected into a vial (1 mL). This step was further followed by electrochemical reduction at -2.0 V for 60 min prior to the NMR analysis (FIG. 25 and FIG. 28).

Example 1.41

Figure 26:
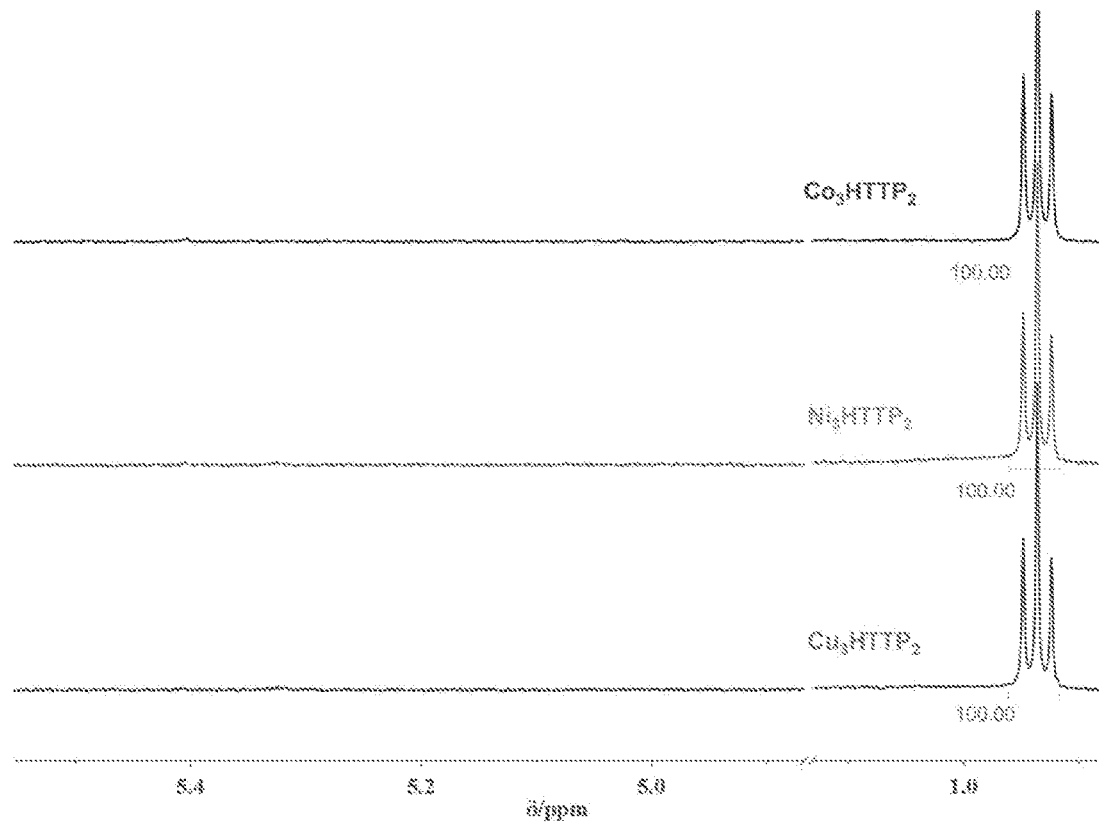
FIG. 26 shows $^1H$ NMR of DMSO-$d_6$ after solid-state ethylene capture by $Co_3HTTP_2$, $Ni_3HTTP_2$ and $Cu_3HTTP_2$ PCPs compressed pellets. Experimental conditions: 60 min exposure to ethylene without the application of potential followed by the exposure to vacuum for 120 min. During the reduction step, no electrical potential was applied to the samples prior to the NMR analysis.

Attempted Electrochemical Capture/Release with $M_3HTTP_2$ Controls without the Oxidation and Reduction Steps Applicants have also performed analogous control experiments during which the investigated PCPs were neither oxidized nor reduced. This control experiment was achieved by exposing the compressed pellet or the drop-casted film of each $M_3HTTP_2$ PCP to ethylene for 60 min (balloon filled with ~600 mL of ethylene, placed above the vial) without the application of positive potential. Applicants have then placed the pellet/film under the vacuum for 120 min to remove any retained/adsorbed ethylene from the PCPs. The vial was then refilled with house $N_2$ for 60 seconds and the NMR solvent (DMSO-$d_6$) with internal standard (3.42×10$^{-4}$ M, total volume of 760 μL) was injected into a vial (1 mL). The $M_3HTTP_2$ PCPs were then left for 60 min without the application of negative potential before the NMR spectra were collected (FIG. 26 and FIG. 29).

Example 1.42

Attempted Electrochemical Capture/Release with HTTP Ligand Controls

The compressed pellet/drop-casted layer of HTTP ligand were oxidized at +2.0 V under ethylene for 60 min (balloon filled with ~600 mL of ethylene, placed above the vial) after which the pellet/drop-casted film were placed under vacuum for 120 min to remove any retained ethylene from the pores of the material. The vial was then refilled with house $N_2$ for 60 seconds and the NMR solvent (DMSO-$d_6$) with internal standard (3.42×10$^{-4}$ M, total volume of 760 μL) was injected into a vial (1 mL). This step was followed by electrochemical release of ethylene for 60 min at -2.0 V. The detection of released ethylene was carried out using NMR spectroscopy (FIG. 32).

Example 1.43

Figure 44:
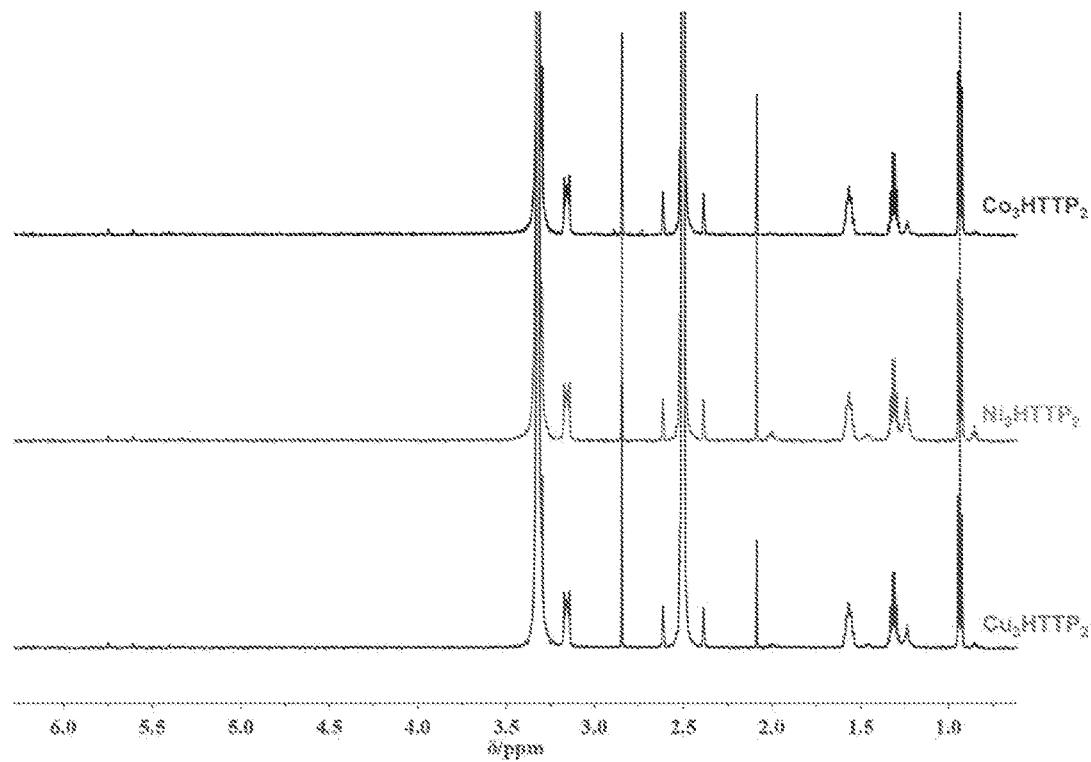
FIG. 44 shows $^1H$ NMR of DMSO-$d_6$ after solid-state ethylene capture by the drop-casted layer of $M_3HTTP_2$ PCPs. Experimental conditions: 60 min oxidation at +2.0 V in the presence of acetylene, after the exposure to vacuum for 120 min and followed by the reduction for 60 min at −2.0 V to release the acetylene from the $M_3HTTP_2$ PCPs drop-casted layer.

Attempted Electrochemical Capture/Release of Acetylene with $M_3HTTP_2$ Controls Applicants have also performed control experiments in which the drop-casted layer of each $M_3HTTP_2$ PCP was exposed to acetylene for 60 min (balloon filled with ~600 mL of acetylene, placed above the vial) while applying +2.0 V electrical potential. This step was followed by the subsequent exposure to vacuum for 120 min to remove any unbound gas. The vial was then refilled with house $N_2$ for 60 seconds and the NMR solvent (DMSO-$d_6$) with internal standard ($3.42 \times 10^{-4}$ M, total volume of 760 µL) was injected into a vial (1 mL). The $M_3HTTP_2$ PCPs were further left for 60 min at −2.0 V before the NMR spectra were collected (FIG. 44).

Example 1.44

Calculations of Ethylene Concentration in the Vial Headspace

Applicants calculated the concentration of ethylene in the headspace of the 20 mL glass vial using following steps:

1) The number of moles of ethylene in the GC vial was calculated using NMR. An internal standard (tetrabutylammonium hexafluorophosphate) was used as a reference. The triplet at 0.9 ppm, which corresponds to the —$CH_3$ group on the butyl chain, was integrated and set to a reference point of 100. The singlet at 5.4 ppm, which corresponds to ethylene, was integrated to find the peak area ratio. Using Equation 1, shown below, the number of moles of ethylene was calculated by dividing the peak area of ethylene by the number of protons of ethylene (4 protons) all over the peak area of the internal standard divided by the number of protons (12 protons). This number is multiplied by the number of moles of internal standard ($2.6 \times 10^{-7}$) to get the number of moles of ethylene in the GC vial.

$$\frac{n_{ethylene}}{n_{is}} = \frac{\frac{\text{peak } area_{ethylene}}{\text{number of } protons_{ethylene}}}{\frac{\text{peak } area_{is}}{\text{number of } protons_{is}}} \quad \text{Equation 1}$$

In Equation 1, above, $n_{ethylene}$ and $n_{is}$ represent number of moles of ethylene and internal standard ($TBAPF_6$) in DMSO, respectively. Peak area determination was performed using TopSpin NMR software (Bruker).

2) Applicants then calculated the partial pressure of ethylene above the NMR solvent using Henry's Law:

$$K_H^{px} = \frac{p_{ethylene}}{x} \quad \text{Equation 2}$$

Where $K_H^{px}$ refers to Henry's constant of ethylene in DMSO (312 atm),[25] $p_{ethylene}$ is the partial pressure (atm) and x represents the mole fraction of ethylene in the DMSO. Mole fraction (x) is equal to the moles of ethylene present in the DMSO divided by the total number of moles in the mixture (DMSO+ethylene) (Equation 2). Volume of DMSO used for all NMR measurements was 750 µL. To calculate the number of moles of DMSO in the mixture, Applicants used the density of DMSO (1.19 g/mL) and molecular weight 84.17 g/mol ($M_{DMSO}$).

3) Volume of ethylene released into the vial was calculated from Boyle's law:

$$V_{occupied} = \frac{V_{vial} * p_{ethylene}}{P_{STD}} \quad \text{Equation 3}$$

Where $V_{released}$ represents the volume of ethylene in the 20 mL glass vial ($V_{vial}$), $p_{ethylene}$ is partial pressure of ethylene (atm) and $P_{STD}$ is standard pressure (1 atm).

4) As one mole of ethylene occupies 22.4 L of volume under standard conditions (1 atm, 273 K), Applicants could calculate the number of moles ($n_{released}$) of ethylene based on the volume ($V_{released}$) calculated from Equation 3.

Example 1.45

Quantification of Solid-State Ethylene Capture by Drop-Casted Films and Compressed Pellets of $M_3HTTP_2$ PCPs Table 4, shown below, illustrates solid-state ethylene uptake by drop-casted layer of $M_3HTTP_2$ PCPs on the conductive slide (exposed surface area of the conductive slide was 3 $cm^2$).

TABLE 4

| Evaluation | $Cu_3HTTP_2$ | $Ni_3HTTP_2$ | $Co_3HTTP_2$ |
|---|---|---|---|
| mg/g of ethylene captured by the drop-casted layer | 3.56 | 6.11 | 2.81 |
| µmol/g of ethylene captured by the drop-casted layer | 100.20 | 218.20 | 126.8 |
| nmol of ethylene captured by the drop-casted film | 501 | 1091 | 634 |
| nmol of ethylene captured in the presence of 2 ppt of $H_2S$ and CO | 250 | 367 | 325 |
| nmol of ethylene captured in the presence of 80 ppm of $H_2S$ and CO | 483 | 912 | 376 |

Table 5, below, illustrates Solid-state ethylene uptake by the compressed pellets of $M_3HTTP_2$ PCPs (exposed surface area of the pellet was 0.84 $cm^2$).

TABLE 5

| Evaluation | $Cu_3HTTP_2$ | $Ni_3HTTP_2$ | $Co_3HTTP_2$ |
|---|---|---|---|
| mg/g of ethylene captured by the compressed pellet | 0.45 | 0.14 | 0.26 |
| µmol/g of ethylene captured by the compressed pellet | 15.97 | 4.90 | 9.31 |
| nmol of ethylene captured by the compressed pellet | 990 | 304 | 577 |
| nmol of ethylene captured in the presence of 2 ppt of $H_2S$ and CO | 105 | 324 | 135 |

Example 1.46

NMRs of Drop-Casted Films of $M_3HTTP_2$ Porous Coordination Polymers Obtained from the Solid-State Capture of Ethylene Example NMRs of drop-casted films of $M_3HTTP_2$ porous coordination polymers obtained from the solid-state capture of ethylene are illustrated in FIG. 39, FIG. 41, and FIG. 43.

Example 1.47

NMRs of Compressed Pellets of $M_3HTTP_2$ Porous Coordination Polymers Obtained from the Solid-State Capture of Ethylene Example NMRs of compressed pellets of $M_3HTTP_2$ porous coordination polymers obtained from the solid-state capture of ethylene are illustrated in FIG. 40 and FIG. 42.

Example 1.48

Control NMRs of Pellet of $M_3HHTP_2$ MOFs Obtained from the Solid-State Capture of Ethylene Example control NMRs of pellet of $M_3HHTP_2$ MOFs obtained from the solid-state capture of ethylene is illustrated in FIG. 30.

Example 1.49

Control NMR Experiments of Drop-Casted Layer of $M_3HHTP_2$ PCPs Obtained from the Solid-State Capture of Ethylene Example control NMR experiments of drop-casted layer of $M_3HHTP_2$ PCPs obtained from the solid-state capture of ethylene are illustrated in FIG. 31.

Example 1.50

Control NMR Experiments of Drop-Casted Layer of $M_3HTTP_2$ PCPs Obtained from the Solid-State Capture of Ethylene Example control NMR experiments of drop-casted layer of $M_3HTTP_2$ PCPs obtained from the solid-state capture of ethylene are illustrated in FIG. 24-FIG. 26.

Example 1.51

Control NMR Experiments of Compressed Pellet of $M_3HTTP_2$ PCPs Obtained from the Solid-State Capture of Ethylene Example control NMR experiments of compressed pellet of $M_3HTTP_2$ PCPs obtained from the solid-state capture of ethylene are illustrated in FIG. 27-FIG. 29.

Example 1.52

Control NMR Experiments of Drop-Casted Layer and Compressed Pellet of HTTP Ligand Obtained from the Solid-State Capture of Ethylene Example control NMR experiments of drop-casted layer and compressed pellet of HTTP ligand obtained from the solid-state capture of ethylene is illustrated in FIG. 32.

Example 1.53

NMR Experiments of Drop-Casted Layer of $M_3HTTP_2$ PCPs Obtained from the Solid-State Capture of Acetylene Example NMR experiments of drop-casted layer of $M_3HTTP_2$ PCPs obtained from the solid-state capture of acetylene is illustrated in FIG. 44.

Without further elaboration, it is believed that one skilled in the art can, using the description herein, utilize the present disclosure to its fullest extent. The embodiments described herein are to be construed as illustrative and not as constraining the remainder of the disclosure in any way whatsoever. While the embodiments have been shown and described, many variations and modifications thereof can be made by one skilled in the art without departing from the spirit and teachings of the invention. Accordingly, the scope of protection is not limited by the description set out above, but is only limited by the claims, including all equivalents of the subject matter of the claims. The disclosures of all patents, patent applications and publications cited herein are hereby incorporated herein by reference, to the extent that they provide procedural or other details consistent with and supplementary to those set forth herein.

What is claimed is:

1. A method for reversibly capturing alkenes, said method comprising:
    associating the alkenes with metal-organic frameworks,
        wherein the metal-organic frameworks comprise one or more metals and one or more ligands coordinated with the one or more metals,
        wherein the coordinated metals and ligands comprise a plurality of metal bis(dithiolene) units,
        wherein the metal-organic frameworks are conductive, and
        wherein the metal-organic frameworks have a two-dimensional structure;
    oxidizing the metal-organic frameworks,
        wherein the oxidizing results in a capturing of the alkenes by the oxidized metal-organic frameworks; and
    reducing the oxidized metal-organic frameworks,
        wherein the reducing results in a releasing of the captured alkenes from the reduced metal-organic frameworks.

2. The method of claim 1,
    wherein the one or more ligands comprise thiol-containing ligands selected from the group consisting of 2,3, 6,7,10,11-hexathiotriphenylene (HTTP), tridentate thiol-containing ligand, bis(dithiolene), and combinations thereof;
    wherein the one or more metals are selected from the group consisting of divalent metals, transition metals, nickel, copper, zinc, manganese, cobalt, chromium, iron, magnesium, tin, palladium, and combinations thereof; and
    wherein the associating comprises flowing or incubating the alkenes through the metal-organic frameworks.

3. The method of claim 1, wherein the metal-organic frameworks are selected from the group consisting of $Co_3HTTP_2$, $Ni_3HTTP_2$, $Cu_3HTTP_2$, and combinations thereof.

4. The method of claim 1, wherein the metal-organic frameworks are associated with a conductive surface, wherein the conductive surface is a conductive slide coated with the metal-organic frameworks or a conductive pellet comprising the metal-organic frameworks, wherein the conductive pellet comprises a plurality of powdered metal-organic frameworks.

5. The method of claim 1, wherein the metal-organic frameworks comprise stacked layers that form a layered structure, wherein the layered structure is in at least one of a slipped parallel configuration and a staggered configuration, and wherein the layered structure has an interlayer distance ranging from about 0.1 nm to about 2 nm.

6. The method of claim 1, wherein the alkenes are selected from the group consisting of ethylene, propylene, butylene, and combinations thereof, and wherein the alkenes are in a gaseous state, a liquid state, or combinations thereof.

7. The method of claim 1, wherein the alkenes are derived from a heterogeneous alkene feed, wherein the heterogeneous alkene feed further comprises at least one of CO, $H_2S$, $H_2$, $C_2H_2$, or mixtures thereof.

8. The method of claim 1, wherein the oxidizing also results in filtration and pre-concentration of the alkenes by the metal-organic frameworks, and wherein the oxidizing occurs by a method selected from the group consisting of thermal-induced oxidation, chemical-induced oxidation, light-induced oxidation, voltage-induced oxidation, and combinations thereof.

9. The method of claim 1, wherein the oxidizing occurs by voltage-induced oxidation, wherein the voltage-induced oxidation comprises applying positive potential to the metal-organic frameworks.

10. The method of claim 1, wherein the capturing of the alkenes comprises solid-state capturing or solution-phase capturing of the alkenes.

11. The method of claim 1, wherein the capturing of the alkenes occurs selectively at a solid-gas interface, wherein the alkenes are in a gaseous state, and wherein the metal-organic frameworks are in a solid-state; and wherein the capturing of the alkenes also results in pre-concentration of the alkenes by the metal-organic frameworks.

12. The method of claim 1, wherein the capturing of the alkenes also results in a catalytic transformation of the alkenes by the metal-organic frameworks, a sensing of the alkenes by the metal-organic frameworks, or combinations thereof.

13. The method of claim 1, wherein the reducing occurs by a method selected from the group consisting of thermal-induced reduction, chemical-induced reduction, light-induced reduction, voltage-induced reduction, and combinations thereof.

14. The method of claim 1, wherein the reducing occurs by voltage-induced reduction, and wherein the voltage-induced reduction comprises applying negative potential to the metal-organic frameworks.

15. The method of claim 1, further comprising a step of reusing the metal-organic frameworks after the releasing step for capture of additional alkenes.

* * * * *